(12) United States Patent
Yasuma et al.

(10) Patent No.: US 8,349,886 B2
(45) Date of Patent: *Jan. 8, 2013

(54) NITROGENATED 5-MEMBERED HETEROCYCLIC COMPOUND

(75) Inventors: Tsuneo Yasuma, Osaka (JP); Osamu Ujikawa, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/937,820

(22) PCT Filed: Apr. 15, 2009

(86) PCT No.: PCT/JP2009/057607
§ 371 (c)(1),
(2), (4) Date: Oct. 14, 2010

(87) PCT Pub. No.: WO2009/128481
PCT Pub. Date: Oct. 22, 2009

(65) Prior Publication Data
US 2011/0190335 A1    Aug. 4, 2011

(30) Foreign Application Priority Data

Apr. 16, 2008  (JP) ................................. 2008-107181
Oct. 27, 2008  (JP) ................................. 2008-275892

(51) Int. Cl.
*A61K 31/426*   (2006.01)
*C07D 401/04*   (2006.01)

(52) U.S. Cl. ...................... 514/415; 548/452
(58) Field of Classification Search ................. 514/415; 548/452
See application file for complete search history.

(56) References Cited

U.S. PATENT DOCUMENTS

| | | | |
|---|---|---|---|
| 2006/0111353 A1 | 5/2006 | Weichert et al. | |
| 2007/0072908 A1 | 3/2007 | Yamamoto et al. | |
| 2007/0197532 A1 | 8/2007 | Cao et al. | |
| 2007/0213349 A1 | 9/2007 | Cheruvallath et al. | |
| 2007/0244169 A1 | 10/2007 | Feng et al. | |
| 2008/0096877 A1 | 4/2008 | Yasuma et al. | |
| 2009/0118304 A1 | 5/2009 | Takahashi et al. | |
| 2009/0247746 A1 | 10/2009 | Yasuma et al. | |
| 2009/0286975 A1 | 11/2009 | Yasuma et al. | |
| 2010/0069431 A1 | 3/2010 | Iwata et al. | |
| 2010/0130446 A1* | 5/2010 | Yasuma et al. ................. | 514/63 |
| 2010/0137610 A1 | 6/2010 | Yasuma et al. | |
| 2010/0144702 A1 | 6/2010 | Yasuma et al. | |

FOREIGN PATENT DOCUMENTS

| | | |
|---|---|---|
| EP | 1 935 890 A1 | 6/2008 |
| EP | 2 149 550 A1 | 2/2010 |
| JP | 2006-515858 | 6/2006 |
| WO | 2004/063179 | 7/2004 |
| WO | 2006/132436 | 12/2006 |
| WO | 2007/037534 | 4/2007 |
| WO | 2007/061923 | 5/2007 |
| WO | 2007/075847 | 7/2007 |
| WO | 2007/104034 | 9/2007 |
| WO | 2008/050821 | 5/2008 |
| WO | 2008/136428 | 11/2008 |

OTHER PUBLICATIONS

Sessler, et al., JACS, 2003, 125, 13646-13647.*
Corriu, et al., Tetrahedron, 48(30), 6231-6244.*
Supplementary European Search Report issued Oct. 18, 2011 in corresponding European Application No. 09 73 2181.4.
Robert J.P. Corriu et al.,"Silylamines in Organic Synthesis, Facile Synthetic Routes to Unsaturated Protected Primary Amines", Tetrahedron, vol. 48, No. 30, Jan. 1, 1992, pp. 6231-6244.
Chun Hua Zhang et al., "Synthesis of New Chiral $C_2$-Symmetrical Bis(oxazoline) Compounds", Chinese Chemical Letters, vol. 14, No. 2, 2003, pp. 125-126.
Jonathan L. Sessler et al., "Pyrazine Analogues of Dipyrrolylquinoxalines", Organic Letters, vol. 5, No. 22, Jan. 10, 2003, pp. 4141-4144.
Jonathan L. Sessler et al., "Synthesis and characterization of a hexaphyrin(1.0.1.0.0.0) bearing both meso- and β-substituent", Journal of Porphyrins and Phthalocyanines, vol. 11, Apr. 20, 2007, pp. 287-293.
J.H. Atkinson et al., "Some Reactions of 2-2'-Pyrrolyl-1-pyrrolines", Journal of the Chemical Society, 1965, pp. 2614-2621.
Kevin R. Guertin et al., "Small Molecule Glucokinase Activators as Glucose Lowering Agents: A New Paradigm for Diabetes Therapy", Current Medicinal Chemistry, vol. 13, No. 15, Jan. 1, 2006, pp. 1839-1843.
International Search Report issued May 19, 2009 in International (PCT) Application No. PCT/JP2009/057607.
J. L. Sessler et al., "Calix[2]bipyrrole[2]furan and Calix[2]bipyrrole[2]thiophene: New Pyrrolic Receptors Exhibiting a Preference for Carboxylate Anions", Journal of the American Chemical Society, vol. 125, No. 45, pp. 13646-13647, 2003.
R. J. P. Corriu et al., "Silylamines in Organic Synthesis. Facile Synthetic Routes to Unsaturated Protected Primary Amines", Tetrahedron, vol. 48, No. 30, pp. 6231-6244, 1992.

* cited by examiner

*Primary Examiner* — Susannah Chung
(74) *Attorney, Agent, or Firm* — Wenderoth, Lind & Ponack, L.L.P.

(57) ABSTRACT

The purpose of the present invention is to provide a glucokinase activator which is useful as a pharmaceutical agent such as agents for the prophylaxis or treatment of diabetes, obesity and the like, and the like.
The present invention is a compound represented by the formula (I):

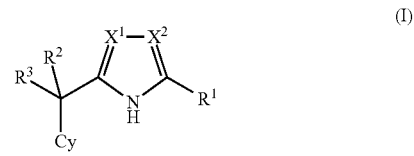

(I)

wherein each symbol is as defined in the specification, or a salt thereof.

12 Claims, No Drawings

SEQUENCE LISTING

<160> NUMBER OF SEQ ID NOS: 4

<210> SEQ ID NO 1
<211> LENGTH: 27
<212> TYPE: DNA
<213> ORGANISM: Artificial sequence
<220> FEATURE:
<223> OTHER INFORMATION: Synthetic construct; primer for cloning
      glucokinase

<400> SEQUENCE: 1
cagctctcca tccaagcagc cgttgct                                         27

<210> SEQ ID NO 2
<211> LENGTH: 21
<212> TYPE: DNA
<213> ORGANISM: Artificial sequence
<220> FEATURE:
<223> OTHER INFORMATION: Synthetic construct; primer for cloning
      glucokinase

<400> SEQUENCE: 2
ggcggcctgg gtcctgacaa g                                               21

<210> SEQ ID NO 3
<211> LENGTH: 69
<212> TYPE: DNA
<213> ORGANISM: Artificial sequence
<220> FEATURE:
<223> OTHER INFORMATION: Synthetic construct; primer for cloning
      glucokinase

<400> SEQUENCE: 3
ggatccatgc ccagaccaag atcccaactc ccacaaccca actcccaggt agagcagatc     60
ctggcagag                                                             69

<210> SEQ ID NO 4
<211> LENGTH: 24
<212> TYPE: DNA
<213> ORGANISM: Artificial sequence
<220> FEATURE:
<223> OTHER INFORMATION: Synthetic construct; primer for cloning
      glucokinase

<400> SEQUENCE: 4
gaattcctgg cccagcatac aggc                                            24

NITROGENATED 5-MEMBERED HETEROCYCLIC COMPOUND

This application is a U.S. national stage of International Application No. PCT/JP2009/057607 filed Apr. 15, 2009.

TECHNICAL FIELD

The present invention relates to nitrogen-containing 5-membered heterocyclic compound having a glucokinase activating action and useful as a therapeutic agent for diabetes and the like.

BACKGROUND OF THE INVENTION

Glucokinase (sometimes to be abbreviated to as GK in the present specification) (EC2.7.1.1) is one of the four kinds of hexokinases found in mammals, and is also called hexokinase IV. GK is an enzyme that catalyzes the conversion of glucose to glucose-6-phosphate, which is the first step of glycolysis. GK is mainly present in the pancreatic β cell and the liver, and acts in the pancreatic β cell as a sensor of extracellular glucose concentration that defines the glucose-stimulated insulin secretion. In the liver, the enzyme reaction of GK becomes a rate determining factor and regulates glycogen synthesis and glycolysis. The three hexokinases (I, II, III) other than GK reach the maximum enzyme activity at a glucose concentration of 1 mM or below. In contrast, GK shows low affinity for glucose and has a Km value of 8-15 mM which is close to a physiological blood glucose level. Accordingly, GK-mediated promotion of intracellular glucose metabolism occurs, which corresponds to blood glucose changes from normal blood glucose (5 mM) to postprandial hyperglycemia (10-15 mM).

The hypothesis proposed by Matschinsky et al. in 1984 that GK acts as a glucose sensor in the pancreatic β cell and hepatocytes has been demonstrated by the analysis of glucokinase transgenic mouse in recent years (see The Journal of Biological Chemistry (J. Biol. Chem.), 1995, vol. 270, page 30253-30256; The Journal of Biological Chemistry (J. Biol. Chem.), 1997, vol. 272, page 22564-22569; The Journal of Biological Chemistry (J. Biol. Chem.), 1997, vol. 272, page 22570-22575; NIHONRINSHO, 2002, vol. 60, page 523-534; and Cell, 1995, vol. 83, page 69-78 (non-patent references 1-5)). That is, GK heterozygous deficient mouse showed a hyperglycemic condition, and further, a disordered glucose-stimulated insulin secretion response. GK homozygous deficient mouse dies shortly after birth with manifestations of marked hyperglycemia and urinary sugar. On the other hand, GK overexpressed mouse (hetero type) showed decreased blood glucose level, increased blood glucose clearance rate, increased liver glycogen content and the like. From these findings, it has been clarified that GK plays an important role in the systemic glucose homeostasis. In other words, decreased GK activity causes insulin secretion failure and lower liver glucose metabolism, which develops impaired glucose tolerance and diabetes. Conversely, GK activation or increased GK activity due to overexpression causes promoted insulin secretion and promoted liver glucose metabolism, which in turn increases the systemic use of glucose to improve glucose tolerance.

In addition, it has been clarified from the analysis of a report on GK gene abnormality mainly in the family of MODY2 (Maturity Onset Diabetes of the Young) that GK also acts as a glucose sensor in human, and plays a key role in glucose homeostasis (see Nature, 1992, vol. 356, page 721-722 (non-patent reference 6)). In GK gene abnormality, due to the decreased affinity of GK for glucose (increased Km value) and decreased Vmax, the blood glucose threshold value of insulin secretion increases and the insulin secretory capacity decreases. In the liver, due to the decreased GK activity, decreased glucose uptake, promoted gluconeogenesis, decreased glycogen synthesis and liver insulin resistance are observed. On the other hand, a family with a mutation increasing the GK activity has also been found. In such family, fasting hypoglycemia associated with increased plasma insulin concentration is observed (see New England Journal Medicine, 1998, vol. 338, page 226-230 (non-patent reference 7)).

As mentioned above, GK acts as a glucose sensor in mammals including human, and plays an important role in blood glucose regulation. On the other hand, control of blood glucose utilizing the glucose sensor system of GK is considered to open a new way to treat diabetes in many type 2 diabetes patients. Particularly, since a GK activating substance is expected to show insulin secretagogue action in the pancreatic β cell and glucose uptake promotion and glucose release suppressive action in the liver, it will be useful as a prophylactic or therapeutic drug for type 2 diabetes.

In recent years, it has been clarified that pancreatic β cell type glucokinase expresses locally in the feeding center (Ventromedial Hypothalamus: VMH) of rat brain. A subset of nerve cell present in VMH is called glucose responsive neuron, and plays an important role in the body weight control. From electrophysiological experiments, the neuron is activated in response to physiological changes in the glucose concentration (5-20 mM). However, since the glucose concentration sensor system of VHM is assumed to have a mechanism mediated by glucokinase as in the case of insulin secretion in the pancreatic β cell, different from pancreatic β cell and the liver, a pharmaceutical agent capable of activating glucokinase of VHM has a possibility of providing not only a blood glucose corrective effect but also improvement of obesity.

As mentioned above, a pharmaceutical agent capable of activating GK is useful as a prophylactic or therapeutic drug for diabetes, diabetic complications, and obesity.

On the other hand, as a nitrogen-containing 5-membered heterocyclic compound, the following compound has been reported. However, the document does not report that the compound has a glucokinase activating action.

Tetrahedron (1992), 48(30), 6231-44 (non-patent document 8) discloses

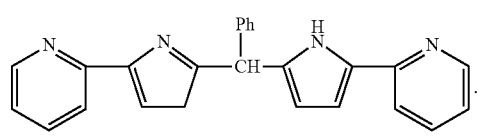 [SMILES: C1=C(c2ccccn2)N=C(C(c2ccccc2)c2ccc(-c3ccccn3)[nH]2)C1]

Prior Art

Non-Patent Documents

Non-Patent Document 1: J. Biol. Chem., 1995, 270 vol., pages 30253-30256

Non-Patent Document 2: J. Biol. Chem., 1997, 272 vol., pages 22564-22569

Non-Patent Document 3: J. Biol. Chem., 1997, 272 vol., pages 22570-22575

Non-Patent Document 4: Japan clinical, 2002, 60 vol., pages 523-534

Non-Patent Document 5: Cell, 1995, 83 vol., pages 69-78

Non-Patent Document 6: Nature, 1992, 356 vol., 7 pages 21-72 non-Patent document 7: New England Journal Medicine, 1998, 338 vol., pages 226-230

Non-Patent Document 8: Tetrahedron (1992), 48(30), 6231-44

SUMMARY OF THE INVENTION

The purpose of the present invention is to provide a glucokinase activator which is useful as a pharmaceutical agent such as an agent for the prophylaxis or treatment of diabetes, obesity and the like, and, the like.

The present inventors have conducted intensive studies and found that a compound represented by the following formula (I):

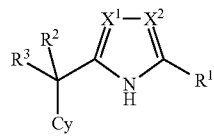

wherein
$R^1$ is a 5- or 6-membered nitrogen-containing heterocyclic group represented by the formula:

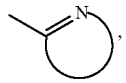

which is optionally substituted;
$R^2$ is an optionally substituted alkyl group, an optionally substituted 4- to 7-membered cyclic group, —$OR^6$ wherein $R^6$ is an optionally substituted alkyl group or an optionally substituted 4- to 7-membered cyclic group, or an optionally substituted amino group;
$R^3$ is a hydrogen atom or an optionally substituted alkyl group, or
$R^2$ and $R^3$
(i) form, together with the carbon atom they are bonded to, cyclopropane substituted by an optionally substituted 4- to 7-membered cyclic group, or
(ii) in combination form =N—$OR^7$ or =CH—$R^7$ wherein $R^7$ is an optionally substituted alkyl group or an optionally substituted 4- to 7-membered cyclic group;
Cy is an optionally substituted 5-membered cyclic group, which is optionally condensed with an optionally substituted 5- to 7-membered ring; and
$X^1$ and $X^2$ are each independently an optionally substituted carbon atom, or a nitrogen atom, or a salt thereof (in the present specification, sometimes to be abbreviated as "compound (I)") unexpectedly has a superior glucokinase activating action as well as superior properties as a pharmaceutical product such as stability, and the like, and can be a safe and useful as a pharmaceutical agent, which resulted in the completion of the present invention.

Accordingly, the present invention relates to
[1] a compound represented by the formula (I) provided that Cy is not 1H-pyrrol-2-yl, or a salt thereof;
[2] the compound of the above-mentioned [1], wherein Cy is pyrazolyl, pyrazolopyridyl, imidazolyl, triazolyl, tetrazolyl, thienyl, furyl, thiazolyl, thiadiazolyl, oxazolyl, oxadiazolyl, isoxazolyl, isothiazolyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl or benzisothiazolyl, each of which is optionally substituted;
[3] the compound of the above-mentioned [1], wherein $R^1$ is a 5- or 6-membered nitrogen-containing aromatic heterocyclic group represented by the formula:

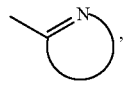

which is optionally substituted;
[4] the compound of the above-mentioned [1], wherein $R^2$ is an optionally substituted $C_{1-6}$ alkyl group;
[5] the compound of the above-mentioned [1], wherein $R^3$ is a hydrogen atom;
[6] the compound of the abovementioned [1], wherein $X^1$ and $X^2$ are both optionally substituted carbon atoms;
[7] the compound of the above-mentioned [1], wherein Cy is pyrazolyl, pyrazolopyridyl, triazolyl, tetrazolyl, thienyl, furyl, thiazolyl, thiadiazolyl, oxazolyl, oxadiazolyl, isoxazolyl, isothiazolyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl or benzisothiazolyl, each of which is optionally substituted, $R^1$ is a 5- or 6-membered nitrogen-containing aromatic heterocyclic group represented by the formula:

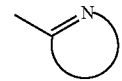

which is optionally substituted,
$R^2$ is an optionally substituted $C_{1-6}$ alkyl group,
$R^3$ is a hydrogen atom, and
$X^1$ and $X^2$ are both optionally substituted carbon atoms;
[8] [2-(5-{1-[1-methyl-5-(methylsulfanyl)-1H-pyrazol-3-yl]-2-(tetrahydro-2H-pyran-4-yl)ethyl}-1H-pyrrol-2-yl)-1,3-thiazol-5-yl]methanol or a salt thereof;
[9] [2-(5-{1-[1-methyl-5-(methylsulfonyl)-1H-pyrazol-3-yl]-2-(tetrahydro-2H-pyran-4-yl)ethyl}-1H-pyrrol-2-yl)-1,3-thiazol-5-yl]methanol or a salt thereof;
[10] 1-(6-{5-[1-(4-methoxy-1H-pyrazolo[3,4-b]pyridin-1-yl)-2-(tetrahydro-2H-pyran-4-yl)ethyl]-1H-pyrrol-2-yl}pyridin-3-yl)-2-methylpropane-1,2-diol or a salt thereof;
[11] 1-[6-(5-{1-[4-(cyclopropylsulfonyl)-1H-indazol-1-yl]-2-(tetrahydro-2H-pyran-4-yl)ethyl}-1H-pyrrol-2-yl)pyridin-3-yl]-2-methylpropane-1,2-diol or a salt thereof;
[12] 1-[6-(5-{1-[4-(cyclopropylsulfonyl)-5-methoxy-1H-indazol-1-yl]-2-(tetrahydro-2H-pyran-4-yl)ethyl}-1H-pyrrol-2-yl)pyridin-3-yl]-2-methylpropane-1,2-diol or a salt thereof;
[13] a prodrug comprising the compound of the above-mentioned [1];
[14] a pharmaceutical agent comprising a compound represented by the formula (I) or a salt thereof, or a prodrug thereof;
[15] the pharmaceutical agent of the above-mentioned [14], which is an glucokinase activator;
[16] the pharmaceutical agent of the above-mentioned [14], which is used for the prophylaxis or treatment of diabetes or obesity;
and the like.

EFFECT OF THE INVENTION

The glucokinase activator of the present invention has a superior activity, and therefore the activator is useful as a pharmaceutical agent such as an agent for the prophylaxis or treatment of diabetes, obesity and the like, and the like.

DETAILED DESCRIPTION OF THE INVENTION

Unless otherwise specified, examples of the "halogen atom" in the present specification include a fluorine atom, a chlorine atom, a bromine atom and an iodine atom.

Unless otherwise specified, examples of the "optionally substituted hydrocarbon group" in the present specification include an "optionally substituted $C_{1-6}$ alkyl group", "optionally substituted $C_{2-6}$ alkenyl group", "optionally substituted $C_{2-6}$ alkynyl group", "optionally substituted $C_{3-7}$ cycloalkyl group", "optionally substituted $C_{6-14}$ aryl group", "optionally substituted $C_{7-16}$ aralkyl group" and the like.

Unless otherwise specified, examples of the "$C_{1-6}$ alkyl group" in the present specification include methyl, ethyl, propyl, isopropyl, butyl, isobutyl, sec-butyl, tert-butyl, pentyl, isopentyl, neopentyl, hexyl and the like.

Unless otherwise specified, examples of the "$C_{2-6}$ alkenyl group" in the present specification include vinyl, propenyl, isopropenyl, 2-buten-1-yl, 2-methyl-1-propenyl, 4-penten-1-yl, 5-hexen-1-yl and the like.

Unless otherwise specified, examples of the "$C_{2-6}$ alkynyl group" in the present specification include 2-butyn-1-yl, 4-pentyn-1-yl, 5-hexyn-1-yl and the like.

Unless otherwise specified, examples of the "$C_{3-7}$ cycloalkyl group" in the present specification include cyclopropyl, cyclobutyl, cyclopentyl, cyclohexyl, cycloheptyl and the like.

Unless otherwise specified, examples of the "$C_{6-14}$ aryl group" in the present specification include phenyl, 1-naphthyl, 2-naphthyl, 2-biphenylyl, 3-biphenylyl, 4-biphenylyl, 2-anthryl and the like.

Unless otherwise specified, examples of the "$C_{7-16}$ aralkyl group" in the present specification include benzyl, 2-phenylethyl, 1-phenylethyl, diphenylmethyl, 1-naphthylmethyl, 2-naphthylmethyl, 2,2-diphenylethyl, 3-phenylpropyl, 3,3-diphenylpropyl, 4-phenylbutyl, 5-phenylpentyl, 2-biphenylylmethyl, 3-biphenylylmethyl, 4-biphenylylmethyl and the like.

Unless otherwise specified, examples of the "$C_{1-6}$ alkoxy group" in the present specification include methoxy, ethoxy, propoxy, isopropoxy, butoxy, isobutoxy, tert-butoxy, pentyloxy, hexyloxy and the like.

Examples of the "$C_{1-10}$ alkoxy group" in the present specification include, besides the above-mentioned $C_{1-6}$ alkoxy group, heptyloxy, octyloxy, nonyloxy, decyloxy and the like.

Examples of the "heterocyclyloxy group" in the present specification include a hydroxy group substituted by the below-mentioned "heterocyclic group". Preferable examples of the heterocyclyloxy group include tetrahydropyranyloxy, thiazolyloxy, pyridyloxy, pyrazolyloxy, oxazolyloxy, thienyloxy, furyloxy, tetrahydrothiopyranyloxy, 1,1-dioxidotetrahydrothiopyranyloxy and the like.

Unless otherwise specified, examples of the "$C_{6-14}$ aryloxy group" in the present specification include phenoxy, 1-naphthyloxy, 2-naphthyloxy and the like.

Unless otherwise specified, examples of the "$C_{7-16}$ aralkyloxy group" in the present specification include benzyloxy, 2-phenylethyloxy, 1-phenylethyloxy and the like.

Unless otherwise specified, examples of the "tri-$C_{1-6}$ alkylsilyloxy group" in the present specification include trimethylsilyloxy, tert-butyl(dimethyl)silyloxy and the like.

Unless otherwise specified, examples of the "$C_{1-6}$ alkylsulfonyloxy group" in the present specification include methylsulfonyloxy, ethylsulfonyloxy and the like.

Examples of the "heterocyclylsulfonyloxy group" in the present specification include a sulfonyloxy group substituted by the below-mentioned "heterocyclic group". Preferable examples of the heterocyclylsulfonyloxy group include, thienylsulfonyloxy, furylsulfonyloxy and the like.

Unless otherwise specified, examples of the "$C_{1-6}$ alkylthio group" Unless otherwise specified, examples of the "methylthio, ethylthio, propylthio, isopropylthio, butylthio, sec-butylthio, tert-butylthio and the like.

Examples of the $C_{1-10}$ alkylthio group" in the present specification include, besides the above-mentioned $C_{1-6}$ alkylthio group, heptylthio, octylthio, nonylthio, decylthio and the like.

Examples of the heterocyclylthio group" in the present specification include a mercapto group substituted by the below-mentioned "heterocyclic group". Preferable examples of the heterocyclylthio group include tetrahydropyranylthio, thiazolylthio, pyridylthio, pyrazolylthio, oxazolylthio, thienylthio, furylthio, tetrahydrothiopyranylthio, 1,1-dioxidotetrahydrothiopyranylthio and the like.

Unless otherwise specified, examples of the "$C_{6-14}$ arylthio group" in the present specification include phenylthio, 1-naphthylthio, 2-naphthylthio and the like.

Unless otherwise specified, examples of the "heterocyclic group" in the present specification include a 5- to 14-membered (monocyclic, bicyclic or tricyclic) heterocyclic group containing, as a ring-constituting atom besides carbon atoms, 1 to 4 hetero atoms selected from a nitrogen atom, a sulfur atom (the sulfur atom is optionally oxidized) and an oxygen atom, preferably (i) a 5- to 14-membered (preferably 5- to 10-membered) aromatic heterocyclic group, (ii) a 4- to 10-membered (preferably 4- to 7-membered) non-aromatic heterocyclic group and the like.

Specific examples thereof include aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), oxadiazolyl (e.g., 2-oxadiazolyl), quinolyl (e.g., 2-quinolyl, 3-quinolyl, 4-quinolyl, 5-quinolyl, 6-quinolyl, 8-quinolyl), isoquinolyl (e.g., 1-isoquinolyl, 3-isoquinolyl, 4-isoquinolyl, 5-isoquinolyl), pyrazinyl (e.g., 1-pyrazinyl, 2-pyrazinyl), pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), triazolyl (e.g., 1,2,4-triazol-1-yl, 1,2,4-triazol-3-yl, 1,2,3-triazol-2-yl, 1,2,3-triazol-4-yl), tetrazolyl (e.g., tetrazol-1-yl, tetrazol-5-yl), indolyl (e.g., 1-indolyl, 2-indolyl, 3-indolyl), indazolyl (e.g., 1-indazolyl, 3-indazolyl, 5-indazolyl), benzofuranyl (e.g., 2-benzofuranyl, 3-benzofuranyl), benzothiophenyl (e.g., 2-benzothiophenyl, 3-benzothiophenyl), benzothiazolyl (e.g., 2-benzothiazolyl), benzoxazolyl (e.g., 2-benzoxazolyl), benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl), benzotriazolyl (e.g., 1-benzotriazolyl, 5-benzotriazolyl), imidazo[1,2-a]pyridyl (e.g., 2-imidazo[1,2-a]pyridyl, imidazo[1,2-a]pyridyl, 6-imidazo[1,2-a]pyridyl), imidazo[1, 2-a]pyrimidinyl (e.g., 2-imidazo[1,2-a]pyrimidinyl, imidazo[1,2-a]pyrimidinyl, 5-imidazo[1,2-a]pyrimidinyl), pyrrolo[2,3-b]pyridyl (e.g., 2-1H-pyrrolo[2,3-b]pyridyl, 3-1H-pyrrolo[2,3-b]pyridyl, 4-1H-pyrrolo[2,3-b]pyridyl), [1,2,4]triazolo[1,5-a]pyridyl (e.g., 2-[1,2,4]triazolo[1,5-a]pyridyl, 6-[1,2,4]triazolo[1,5-a]pyridyl, 7-[1,2,4]triazolo[1,5-a]pyridyl), pyrazolopyridyl (e.g., 1-1H-pyrazolo[3,4-b]pyridyl) and the like;

non-aromatic heterocyclic groups such as azetidinyl (e.g., 1-azetidinyl, 2-azetidinyl, 3-azetidinyl), pyrrolidinyl (e.g., 1-pyrrolidinyl, 2-pyrrolidinyl, 3-pyrrolidinyl), oxazolidinyl (e.g., 2-oxazolidinyl), dihydrooxadiazolyl (e.g., 2-dihydrooxadiazolyl), imidazolinyl (e.g., 1-imidazolinyl, 2-imidazolinyl, 4-imidazolinyl), imidazolidinyl (e.g., 3-imidazolidinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), 1-oxidothiomorpholinyl (e.g., 1-oxidothiomorpholino), 1,1-dioxidothiomorpholinyl (e.g., 1,1-dioxidothiomorpholino), tetrahydropyranyl (e.g., 2-tetrahydropyranyl, 3-tetrahydropyranyl, 4-tetrahydropyranyl), tetrahydrofuranyl (e.g., 2-tetrahydrofuranyl, 3-tetrahydrofuranyl), dioxolanyl, oxetanyl (e.g., 2-oxetanyl, 3-oxetanyl), oxopyrrolidinyl (e.g., 2-oxopyrrolidin-1-yl, 2-oxopyrrolidin-3-yl, 2-oxopyrrolidin-4-yl, 2-oxopyrrolidin-5-yl, 3-oxopyrrolidin-1-yl), dioxopyrrolidinyl (e.g., 2,5-dioxopyrrolidin-1-yl, 2,5-dioxopyrrolidin-3-yl), tetrahydrothiopyranyl (e.g., 2-tetrahydrothiopyranyl, 3-tetrahydrothiopyranyl, 4-tetrahydrothiopyranyl), 1,1-dioxidotetrahydrothiopyranyl (e.g., 1,1-dioxidotetrahydrothiopyran-2-yl, 1,1-dioxidotetrahydrothiopyran-3-yl, 1,1-dioxidotetrahydrothiopyran-4-yl), dihydrobenzofuranyl (e.g., 2,3-dihydro-1-benzofuran-4-yl, 2,3-dihydro-1-benzofuran-5-yl, 2,3-dihydro-1-benzofuran-6-yl, 2,3-dihydro-1-benzofuran-7-yl), benzodioxolyl (e.g., benzodioxol-5-yl), tetrahydrobenzo[c]azepinyl (e.g., 1,3,4,5-tetrahydrobenzo[c]azepin-2-yl), tetrahydroisoquinolinyl (e.g., 1,2,3,4-tetrahydroisoquinolin-2-yl) and the like, and the like.

In addition, the above-mentioned non-aromatic heterocyclic group may be a cross-linked non-aromatic heterocyclic group. Examples of the cross-linked non-aromatic heterocyclic group include diazabicyclo[2.2.1]heptan-2-yl (e.g., 2,5-diazabicyclo[2.2.1]heptan-2-yl), azabicyclo[2.2.2]octan-3-yl (e.g., 1-azabicyclo[2.2.2]octan-3-yl) and the like.

Unless otherwise specified, examples of the "$C_{1-6}$ alkylsulfonyl group" in the present specification include methylsulfonyl, ethylsulfonyl and the like.

Unless otherwise specified, examples of the "$C_{3-7}$ cycloalkylsulfonyl group" in the present specification include cyclopropylsulfonyl, cyclobutylsulfonyl, cyclopentylsulfonyl and the like.

Unless otherwise specified, examples of the "$C_{6-14}$ arylsulfonyl group" in the present specification include phenylsulfonyl, 1-naphthylsulfonyl, 2-naphthylsulfonyl and the like.

Unless otherwise specified, examples of the "$C_{1-6}$ alkylsulfinyl group" in the present specification include methylsulfinyl, ethylsulfinyl and the like.

Unless otherwise specified, examples of the "$C_{6-14}$ arylsulfinyl group" in the present specification include phenylsulfinyl, 1-naphthylsulfinyl, 2-naphthylsulfinyl and the like.

Unless otherwise specified, examples of the "$C_{1-6}$ alkylcarbonyl group" in the present specification include acetyl, isobutanoyl, isopentanoyl and the like.

Unless otherwise specified, examples of the "$C_{6-14}$ arylcarbonyl group" in the present specification include benzoyl, 1-naphthylcarbonyl, 2-naphthylcarbonyl and the like.

Unless otherwise specified, examples of the "$C_{1-6}$ alkoxy-carbonyl group" in the present specification include methoxycarbonyl, ethoxycarbonyl, propoxycarbonyl, tert-butoxycarbonyl and the like.

Unless otherwise specified, examples of the "heterocyclylcarbonyl group" in the present specification include a carbonyl group substituted by the aforementioned "heterocyclic group". Specific examples thereof include azetidinylcarbonyl, pyrrolidinylcarbonyl, piperidinocarbonyl, piperazinylcarbonyl, morpholinocarbonyl, thiomorpholinocarbonyl, thienylcarbonyl, tetrahydrobenzo[c]azepinylcarbonyl, tetrahydroisoquinolinylcarbonyl and the like.

Unless otherwise specified, examples of the "optionally esterified carboxy group" in the present specification include a carboxy group, a $C_{1-6}$ alkoxy-carbonyl group (e.g., methoxycarbonyl, ethoxycarbonyl, propoxycarbonyl, tert-butoxycarbonyl etc.), a $C_{6-14}$ aryloxy-carbonyl group (e.g., phenoxycarbonyl etc.), a $C_{7-16}$ aralkyloxy-carbonyl group (e.g., benzyloxycarbonyl, 2-phenylethyloxycarbonyl etc.) and the like.

Unless otherwise specified, examples of the "optionally halogenated $C_{1-6}$ alkyl group" in the present specification include the above-mentioned "$C_{1-6}$ alkyl group" optionally having 1 to 5 "halogen atoms" mentioned above. Specific examples thereof include methyl, ethyl, propyl, isopropyl, butyl, tert butyl, isobutyl, trifluoromethyl and the like.

Unless otherwise specified, examples of the "optionally halogenated $C_{1-6}$ alkoxy group" in the present specification include the above-mentioned "$C_{1-6}$ alkoxy group" optionally having 1 to 5 "halogen atoms" mentioned above. Specific examples thereof include methoxy, ethoxy, isopropoxy, tert-butoxy, trifluoromethoxy and the like.

Unless otherwise specified, examples of the "mono- or di-$C_{1-6}$ alkyl-amino group" in the present specification include an amino group mono- or di-substituted by the above-mentioned "$C_{1-6}$ alkyl group". Specific examples thereof include methylamino, ethylamino, propylamino, dimethylamino, diethylamino and the like.

Unless otherwise specified, examples of the "mono- or di-$C_{3-7}$ cycloalkyl-amino group" in the present specification include an amino group mono- or di-substituted by the above-mentioned "$C_{3-7}$ cycloalkyl group". Specific examples thereof include cyclopropylamino and the like.

Unless otherwise specified, examples of the "mono- or di-$C_{6-14}$ aryl-amino group" in the present specification include an amino group mono- or di-substituted by the above-mentioned "$C_{6-14}$ aryl group". Specific examples thereof include phenylamino, diphenylamino, 1-naphthylamino, 2-naphthylamino and the like.

Unless otherwise specified, examples of the "mono- or di-$C_{7-16}$ aralkyl-amino group" in the present specification include an amino group mono- or di-substituted by the above-mentioned "$C_{7-16}$ aralkyl group". Specific examples thereof include benzylamino, 2-phenylethylamino and the like.

Unless otherwise specified, examples of the "N—$C_{1-6}$ alkyl-N—$C_{6-14}$ aryl-amino group" in the present specification include an amino group substituted by the above-mentioned "$C_{1-6}$ alkyl group" and the above-mentioned "$C_{6-14}$ aryl group". Specific examples thereof include N-methyl-N-phenylamino, N-ethyl-N-phenylamino and the like.

Unless otherwise specified, examples of the "N—$C_{1-6}$ alkyl-N—$C_{7-16}$ aralkyl-amino group" in the present specification include an amino group substituted by the above-mentioned "$C_{1-6}$ alkyl group" and the above-mentioned "$C_{7-16}$ aralkyl group". Specific examples thereof include N-methyl-N-benzylamino, N-ethyl-N-benzylamino and the like.

Unless otherwise specified, examples of the "mono- or di-($C_{1-6}$ alkyl-carbonyl)-amino group" in the present specification include an amino group mono- or di-substituted by the above-mentioned "$C_{1-6}$ alkyl-carbonyl group". Specific examples thereof include acetylamino and the like.

Unless otherwise specified, examples of the "mono- or di-($C_{1-6}$ alkoxy-carbonyl)-amino group" in the present specification include an amino group mono- or di-substituted by the above-mentioned "$C_{1-6}$ alkoxy-carbonyl group". Specific examples thereof include methoxycarbonylamino, ethoxycarbonylamino, propoxycarbonylamino, tert-butoxycarbonylamino and the like.

Unless otherwise specified, examples of the "N—$C_{1-6}$ alkyl-N—($C_{1-6}$ alkyl-carbonyl)-amino group" in the present specification include an amino group substituted by the above-mentioned "$C_{1-6}$ alkyl group" and the above-mentioned "$C_{1-6}$ alkyl-carbonyl group". Specific examples thereof include N-acetyl-N-methylamino, N-acetyl-N-ethylamino and the like.

Unless otherwise specified, examples of the "mono- or di-$C_{1-6}$ alkyl-carbamoyl group" in the present specification include a carbamoyl group mono- or di-substituted by the above-mentioned "$C_{1-6}$ alkyl group". Specific examples thereof include methylcarbamoyl, ethylcarbamoyl, dimethylcarbamoyl, diethylcarbamoyl, ethylmethylcarbamoyl and the like.

Unless otherwise specified, examples of the "mono- or di-$C_{6-14}$ aryl-carbamoyl group" in the present specification include a carbamoyl group mono- or di-substituted by the above-mentioned "$C_{6-14}$ aryl group". Specific examples thereof include phenylcarbamoyl, 1-naphthylcarbamoyl, 2-naphthylcarbamoyl and the like.

Unless otherwise specified, examples of the "mono- or di-$C_{3-7}$ cycloalkyl-carbamoyl group" in the present specification include a carbamoyl group mono- or di-substituted by the above-mentioned "$C_{3-7}$ cycloalkyl group". Specific examples thereof include cyclopropylcarbamoyl, cyclopentylcarbamoyl, cydlohexylcarbamoyl and the like.

Unless otherwise specified, examples of the "mono- or di-5- to 7-membered heterocyclylcarbamoyl group" in the present specification include a carbamoyl group mono- or di-substituted by the above-mentioned 5- to 7-membered heterocyclic group. Examples of the 5- to 7-membered heterocyclic group include a 5- to 7-membered heterocyclic group from among the above-mentioned "heterocyclic groups". Preferable examples of the "mono- or di-5- to 7-membered heterocyclylcarbamoyl group" include 2-pyridylcarbamoyl, 3-pyridylcarbamoyl, 4-pyridylcarbamoyl, 2-thienylcarbamoyl, 3-thienylcarbamoyl and the like.

Unless otherwise specified, examples of the "N—$C_{1-6}$ alkyl-N—$C_{1-6}$ alkoxy-carbamoyl group" in the present specification include a carbamoyl group substituted by the above-mentioned "$C_{1-6}$ alkyl group" and the above-mentioned "$C_{1-6}$ alkoxy group". Specific examples thereof include N-methyl-N-methoxycarbamoyl and the like.

Unless otherwise specified, examples of the "mono- or di-$C_{1-6}$ alkyl-sulfamoyl group" in the present specification include a sulfamoyl group mono- or di-substituted by the above-mentioned "$C_{1-6}$ alkyl group". Specific examples thereof include methylsulfamoyl, ethylsulfamoyl, dimethylsulfamoyl, diethylsulfamoyl and the like.

Unless otherwise specified, examples of the "mono- or di-$C_{6-14}$ aryl-sulfamoyl group" in the present specification include a sulfamoyl group mono- or di-substituted by the above-mentioned "$C_{6-44}$ aryl group". Specific examples thereof include phenylsulfamoyl, diphenylsulfamoyl, 1-naphthylsulfamoyl, 2-naphthylsulfamoyl and the like.

Unless otherwise specified, examples of the "$C_{1-6}$ alkoxy-$C_{1-6}$ alkoxy group" in the present specification include the above-mentioned "$C_{1-6}$ alkoxy group" having 1 to 5 "$C_{1-6}$ alkoxy groups" mentioned above. Specific examples thereof include methoxymethoxy, ethoxymethoxy, isopropoxymethoxy, tert-butoxy methoxy, methoxyethoxy, ethoxyethoxy, isopropoxyethoxy, tert-butoxy ethoxy and the like.

Unless otherwise specified, examples of the "nitrogen-containing heterocyclic group" in the present specification include a heterocyclic group containing at least one nitrogen atom from among the above-mentioned "heterocyclic groups". Specific examples thereof include nitrogen-containing aromatic heterocyclic groups such as pyridyl, thiazolyl, oxazolyl, oxadiazolyl, quinolyl, isoquinolyl, pyrazinyl, pyrimidinyl, pyrrolyl, imidazolyl, pyrazolyl, pyridazinyl, isothiazolyl, isoxazolyl, triazolyl, thiadiazolyl, tetrazolyl, indolyl, indazolyl, benzothiazolyl, benzoxazolyl, benzimidazolyl, benzotriazolyl, imidazopyridyl, imidazopyrimidinyl, thiazolopyridyl, pyrazolopyridyl, pyrrolopyridyl, triazolopyridyl and the like;

nitrogen-containing non-aromatic heterocyclic groups such as azetidinyl, pyrrolidinyl, oxazolidinyl, dihydrooxadiazolyl, imidazolinyl, imidazolidinyl, piperidinyl, piperazinyl, morpholinyl, thiomorpholinyl, 1-oxidothiomorpholinyl, 1,1-dioxidothiomorpholinyl, tetrahydroquinolinyl, tetrahydroisoquinolinyl and the like and the like.

Unless otherwise specified, examples of the "nitrogen-containing heterocyclylsulfonyl group" in the present specification include a sulfonyl group having the above-mentioned "nitrogen-containing heterocyclic group". Preferable specific examples include pyridylsulfonyl, thiazolylsulfonyl, oxazolylsulfonyl, oxadiazolylsulfonyl, quinolylsulfonyl, isoquinolylsulfonyl, pyrazinylsulfonyl, pyrimidinylsulfonyl, pyrrolylsulfonyl, imidazolylsulfonyl, pyrazolylsulfonyl, pyridazinylsulfonyl, isothiazolylsulfonyl, isoxazolylsulfonyl, triazolylsulfonyl, tetrazolylsulfonyl, indolylsulfonyl, indazolylsulfonyl, benzothiazolylsulfonyl, benzoxazolylsulfonyl, benzimidazolylsulfonyl, benzotriazolylsulfonyl, imidazopyridylsulfonyl, imidazopyrimidinylsulfonyl, pyrazolopyridylsulfonyl, pyrrolopyridylsulfonyl, triazolopyridylsulfonyl, azetidinylsulfonyl, pyrrolidinylsulfonyl, oxazolidinylsulfonyl, dihydrooxadiazolylsulfonyl, imidazolinylsulfonyl, imidazolidinylsulfonyl, piperidinylsulfonyl, piperazinylsulfonyl, morpholinylsulfonyl, thiomorpholinylsulfonyl, 1-oxidothiomorpholinylsulfonyl, 1,1-dioxidothiomorpholinylsulfonyl, tetrahydroquinolinylsulfonyl, tetrahydroisoquinolinylsulfonyl and the like.

Unless otherwise specified, examples of the "nitrogen-containing heterocyclylamino group" in the present specification include an amino group mono- or di-substituted by the above-mentioned "nitrogen-containing heterocyclic group". Preferable specific examples include pyridylamino, thiazolylamino, oxazolylamino, oxadiazolylamino, quinolylamino, isoquinolylamino, pyrazinylamino, pyrimidinylamino, pyrrolylamino, imidazolylamino, pyrazolylamino, pyridazinylamino, isothiazolylamino, isoxazolylamino, triazolylamino, tetrazolylamino, indolylamino, indazolylamino, benzothiazolylamino, benzoxazolylamino, benzimidazolylamino, benzotriazolylamino, imidazopyridylamino, imidazopyrimidinylamino, pyrazolopyridylamino, pyrrolopyridylamino, triazolopyridylamino, azetidinylamino, pyrrolidinylamino, oxazolidinylamino, dihydrooxadiazolylamino, imidazolinylamino, imidazolidinylamino, piperidinylamino, piperazinylamino, morpholinylamino, thiomorpholinylamino, 1-oxidothiomorpholinylamino, 1,1-dioxidothiomorpholinylamino, tetrahydroquinolinylamino, tetrahydroisoquinolinylamino, azabicyclo[2.2.2]octan-3-ylamino and the like.

Unless otherwise specified, examples of the "$C_{1-6}$ alkyl-carbonyloxy group" in the present specification include acetyloxy, propanoyloxy, butanoyloxy, isobutanoyloxy, pentanoyloxy, isopentanoyloxy and the like.

Unless otherwise specified, examples of the "$C_{1-4}$ alkylenedioxy group" in the present specification include methylenedioxy, ethylenedioxy and the like.

Examples of the "optionally substituted $C_{1-6}$ alkyl group", "optionally substituted $C_{2-6}$ alkenyl group", "optionally substituted $C_{2-6}$ alkynyl group", "optionally substituted $C_{1-10}$ alkoxy group (including optionally substituted $C_{1-6}$ alkoxy group)", "optionally substituted $C_{1-6}$ alkylsulfonyloxy group", and "optionally substituted $C_{1-10}$ alkylthio group" in the present specification include a "$C_{1-6}$ alkyl group", "$C_{2-6}$ alkenyl group", "$C_{2-6}$ alkynyl group", "$C_{1-10}$ alkoxy group (including $C_{1-6}$ alkoxy group)", "$C_{1-6}$ alkylsulfonyloxy group" and "$C_{1-10}$ alkylthio group", each of which optionally has, at substitutable positions, 1 to 5 substituents selected from (1) a halogen atom;
(2) a hydroxy group;
(3) an amino group;
(4) a nitro group;
(5) a cyano group;
(6) a heterocyclic group optionally substituted by 1 to 3 substituents selected from
  (a) a halogen atom,
  (b) a hydroxy group,
  (c) an amino group,
  (d) a nitro group,
  (e) a cyano group,
  (f) a $C_{1-6}$ alkyl group (the $C_{1-6}$ alkyl group is optionally substituted by 1 to 3 substituents selected from a halogen atom, a cyano group, a $C_{3-7}$ cycloalkyl group and a $C_{6-14}$ aryl group),
  (g) a $C_{2-6}$ alkenyl group (the $C_{2-6}$ alkenyl group is optionally substituted by a $C_{6-14}$ aryl group optionally having 1 to 3 halogen atoms),
  (h) a mono- or di-$C_{1-6}$ alkyl-amino group,
  (i) a $C_{6-14}$ aryl group (the $C_{6-14}$ aryl group optionally has 1 to 3 $C_{1-6}$ alkoxy groups),
  (j) a mono- or di-$C_{6-14}$ aryl-amino group,
  (k) a $C_{3-7}$ cycloalkyl group,
  (l) a $C_{1-6}$ alkoxy group,
  (m) a $C_{7-16}$ aralkyloxy group,
  (n) a $C_{1-6}$ alkoxy-$C_{1-6}$ alkoxy group,
  (o) a $C_{1-6}$ alkylthio group,
  (p) a $C_{1-6}$ alkylsulfinyl group,
  (q) a $C_{1-6}$ alkylsulfonyl group,
  (r) an optionally esterified carboxy group,
  (s) a carbamoyl group,
  (t) a thiocarbamoyl group,
  (u) a mono- or di-$C_{1-6}$ alkyl-carbamoyl group,
  (v) a mono- or di-$C_{6-14}$ aryl-carbamoyl group,
  (w) a sulfamoyl group,
  (x) a mono- or di-$C_{1-6}$ alkyl-sulfamoyl group,
  (y) a mono- or di-$C_{6-14}$ aryl-sulfamoyl group,
  (z) a heterocyclic group, and
  (aa) a $C_{1-6}$ alkyl-carbonyl group;
(7) a mono- or di-$C_{1-6}$ alkyl-amino group (the $C_{1-6}$ alkyl is optionally substituted by 1 to 3 substituents selected from a hydroxy group, a $C_{1-6}$ alkylthio group and a $C_{1-6}$ alkyl-sulfonyl group);
(8) a mono- or di-$C_{3-7}$ cycloalkyl-amino group;
(9) a mono- or di-$C_{6-14}$ aryl-amino group (the $C_{6-14}$ aryl is optionally substituted by 1 to 3 halogen atoms);
(10) a mono- or di-$C_{7-16}$ aralkyl-amino group;
(11) an N—$C_{1-6}$ alkyl-N—$C_{6-14}$ aryl-amino group;
(12) an N—$C_{1-6}$ alkyl-N—$C_{7-16}$ aralkyl-amino group;
(13) $C_{3-7}$ cycloalkyl group optionally having 1 to 3 $C_{1-6}$ alkyl groups;
(14) a $C_{1-6}$ alkoxy group optionally substituted by 1 to 3 substituents selected from
  (a) a halogen atom, and
  (b) a $C_{1-6}$ alkoxy group;
(15) a $C_{1-6}$ alkylthio group optionally having 1 to 3 substituents selected from
  (a) a hydroxy group, and
  (b) a $C_{1-6}$ alkoxy group;
(16) a $C_{1-6}$ alkylsulfinyl group optionally having 1 to 3 $C_{1-6}$ alkoxy groups;
(17) a $C_{1-6}$ alkylsulfonyl group optionally substituted by 1 to 3 substituents selected from
  (a) a hydroxy group, and
  (b) a $C_{1-6}$ alkoxy group;
(18) a $C_{3-7}$ cycloalkylsulfonyl group;
(19) an optionally esterified carboxy group;
(20) a carbamoyl group;
(21) a thiocarbamoyl group;
(22) a mono- or di-$C_{1-6}$ alkyl-carbamoyl group;
(23) a mono- or di-$C_{6-14}$ aryl-carbamoyl group;
(24) a mono- or di-5- to 7-membered heterocyclylcarbamoyl group;
(25) an N—$C_{1-6}$ alkyl-N—$C_{1-6}$ alkoxy-carbamoyl group;
(26) a mono- or di-($C_{1-6}$ alkyl-carbonyl (the $C_{1-6}$ alkyl optionally has 1 to 3 carboxy groups))-amino group;
(27) a $C_{6-14}$ aryloxy group optionally substituted by 1 to 3 substituents selected from
  (a) a halogen atom,
  (b) a hydroxy group,
  (c) an amino group,
  (d) a nitro group,
  (e) a cyano group,
  (f) an optionally halogenated $C_{1-6}$ alkyl group,
  (g) a mono- or di-$C_{1-6}$ alkyl-amino group,
  (h) a $C_{6-14}$ aryl group,
  (i) a mono- or di-$C_{6-14}$ aryl-amino group,
  (j) a $C_{3-7}$ cycloalkyl group,
  (k) a $C_{1-6}$ alkoxy group,
  (l) a $C_{1-6}$ alkoxy-$C_{1-6}$ alkoxy group,
  (m) a $C_{1-6}$ alkoxy-carbonyl group,
  (n) a $C_{1-6}$ alkylthio group,
  (o) a $C_{1-6}$ alkylsulfinyl group,
  (p) a $C_{1-6}$ alkylsulfonyl group,
  (q) an optionally esterified carboxy group,
  (r) a carbamoyl group,
  (s) a thiocarbamoyl group,
  (t) a mono- or di-$C_{1-6}$ alkyl-carbamoyl group,
  (u) a mono- or di-$C_{6-14}$ aryl-carbamoyl group,
  (v) a sulfamoyl group,
  (w) a mono- or di-$C_{1-6}$ alkyl-sulfamoyl group, and
  (x) a mono- or di-$C_{6-14}$ aryl-sulfamoyl group;
(28) a $C_{6-14}$ aryl group optionally substituted by 1 to 3 substituents selected from
  (a) a halogen atom,
  (b) a hydroxy group, (c) an amino group,
(d) a nitro group,
(e) a cyano group,
(f) a $C_{1-6}$ alkyl group (the $C_{1-6}$ alkyl group is optionally substituted by 1 to 3 substituents selected from a halogen atom and a hydroxy group),
(g) a mono- or di-$C_{1-6}$ alkyl-amino group,
(h) a $C_{6-14}$ aryl group,
(i) a mono- or di-$C_{6-14}$ aryl-amino group,
(j) a mono- or di-($C_{1-6}$ alkyl-carbonyl)-amino group,
(k) a $C_{3-7}$ cycloalkyl group,
(l) a $C_{1-6}$ alkoxy group (the $C_{1-6}$ alkoxy group is optionally substituted by 1 to 3 halogen atoms),
(m) a $C_{1-6}$ alkoxy-$C_{1-6}$ alkoxy group,
(n) a $C_{1-6}$ alkylthio group,
(o) a $C_{1-6}$ alkylsulfinyl group,
(p) a $C_{1-6}$ alkylsulfonyl group,
(q) an optionally esterified carboxy group,
(r) a carbamoyl group,
(s) a thiocarbamoyl group,
(t) a mono- or di-$C_{1-6}$ alkyl-carbamoyl group,
(u) a mono- or di-$C_{6-14}$ aryl-carbamoyl group,
(v) a sulfamoyl group,
(w) a mono- or di-$C_{1-6}$ alkyl-sulfamoyl group,
(x) a mono- or di-$C_{6-14}$ aryl-sulfamoyl group,
(y) a $C_{1-6}$ alkyl-carbonyl group,
(z) a heterocyclic group, and
(aa) a heterocyclylcarbonyl group;
(29) a heterocyclyloxy group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(30) a sulfamoyl group;
(31) a mono- or di-$C_{1-6}$ alkyl-sulfamoyl group;
(32) a mono- or di-$C_{6-14}$ aryl-sulfamoyl group;
(33) a $C_{7-16}$ aralkyloxy group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(34) a $C_{1-6}$ alkylsulfonyloxy group;
(35) a tri-$C_{1-6}$ alkyl-silyloxy group;
(36) a heterocyclylcarbonyl group;
(37) a $C_{6-14}$ aryl-carbonyl group;
(38) a $C_{6-14}$ arylthio group optionally substituted by 1 to 3 substituents selected from a halogen atom and a cyano group;
(39) a $C_{6-14}$ arylsulfinyl group optionally having 1 to 3 halogen atoms;
(40) a $C_{6-14}$ arylsulfonyl group optionally having 1 to 3 halogen atoms;
(41) a nitrogen-containing heterocyclylsulfonyl group;
(42) a heterocyclylthio group;
(43) a nitrogen-containing heterocyclylamino group optionally substituted by 1 to 3 substituents selected from a cyano group and a nitro group;
(44) a tert-butyl-diphenylsilyloxy group;
(45) a tert-butyl-dimethylsilyloxy group;
(46) a $C_{1-6}$ alkyl-carbonyloxy group optionally substituted by 1 to 3 substituents selected from an amino group optionally mono- or di-substituted by $C_{1-6}$ alkoxy-carbonyl group(s); and the like.

Examples of the "optionally substituted $C_{3-7}$ cycloalkyl group", "optionally substituted $C_{6-14}$ aryl group", "optionally substituted $C_{7-16}$ aralkyl group", "optionally substituted heterocyclic group", "optionally substituted heterocyclyloxy group", "optionally substituted $C_{6-14}$ aryloxy group", "optionally substituted $C_{7-16}$ aralkyloxy group", "optionally substituted heterocyclylsulfonyloxy group", "optionally substituted heterocyclylthio group", "optionally substituted $C_{6-14}$ arylthio group" and "optionally substituted $C_{7-16}$ aralkylthio group" in the present specification include a "$C_{3-7}$ cycloalkyl group", "$C_{6-14}$ aryl group", "$C_{7-16}$ aralkyl group", "heterocyclic group", "heterocyclyloxy group", "$C_{6-14}$ aryloxy group", "$C_{7-16}$ aralkyloxy group", "heterocyclylsulfonyloxy group", "heterocyclylthio group", "$C_{6-14}$ arylthio group" and "$C_{7-16}$ aralkylthio group", each of which optionally has, at substitutable positions, 1 to 5 substituents selected from
(1) a halogen atom;
(2) a hydroxy group;
(3) an amino group;
(4) a nitro group;
(5) a cyano group;
(6) an optionally substituted $C_{1-6}$ alkyl group;
(7) an optionally substituted $C_{2-6}$ alkenyl group;
(8) an optionally substituted $C_{2-6}$ alkynyl group;
(9) a $C_{6-14}$ aryl group optionally substituted by 1 to 3 substituents selected from
(a) a halogen atom,
(b) a hydroxy group,
(c) an amino group,
(d) a nitro group, (e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(10) a $C_{6-14}$ aryloxy group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(11) a $C_{7-16}$ aralkyloxy group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(12) a heterocyclic group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(13) a mono- or di-$C_{1-6}$ alkyl-amino group;
(14) a mono- or di-$C_{6-14}$ aryl-amino group;
(15) a mono- or di-$C_{7-16}$ aralkyl-amino group;
(16) a mono- or di-($C_{1-6}$ alkoxy-carbonyl)-amino group;
(17) an N—$C_{1-6}$ alkyl-N—$C_{6-14}$ aryl-amino group;
(18) an N—$C_{1-6}$ alkyl-N—$C_{7-16}$ aralkyl-amino group;
(19) a $C_{3-7}$ cycloalkyl group;
(20) an optionally substituted $C_{1-6}$ alkoxy group;
(21) a $C_{1-6}$ alkylthio group optionally having 1 to 3 substituents selected from
(a) a hydroxy group,
(b) a carboxy group,
(c) a $C_{1-6}$ alkoxy group, and
(d) a $C_{1-6}$ alkoxy-carbonyl group;
(22) a $C_{1-6}$ alkylsulfinyl group optionally having 1 to 3 $C_{1-6}$ alkoxy groups;
(23) a $C_{1-6}$ alkylsulfonyl group optionally having 1 to 3 $C_{1-6}$ alkoxy groups;
(24) a $C_{3-7}$ cycloalkylsulfonyl group;
(25) an optionally esterified carboxy group;
(26) a carbamoyl group;
(27) a thiocarbamoyl group;
(28) a mono- or di-$C_{1-6}$ alkyl-carbamoyl group (the $C_{1-6}$ alkyl is optionally substituted by 1 to 3 substituents selected from a hydroxy group and $C_{1-6}$ alkoxy);
(29) a mono- or di-$C_{6-14}$ aryl-carbamoyl group;
(30) a mono- or di-5- to 7-membered heterocyclylcarbamoyl group;
(31) a mono- or di-$C_{3-7}$ cycloalkyl-carbamoyl group;
(32) an N—$C_{1-6}$ alkoxy-carbamoyl group;
(33) a sulfamoyl group;
(34) a mono- or di-$C_{1-6}$ alkyl-sulfamoyl group;
(35) a mono- or di-$C_{6-14}$ aryl-sulfamoyl group;
(36) a $C_{1-6}$ alkylsulfonyloxy group;
(37) a tri-$C_{1-6}$ alkyl-silyloxy group;
(38) a $C_{1-6}$ alkyl-carbonyl group;
(39) a heterocyclylcarbonyl group;

(40) a heterocyclyloxy group optionally substituted by 1 to 3 substituents selected from
(a) a halogen atom,
(b) a hydroxy group,
(c) an amino group,
(d) a nitro group,
(e) a cyano group,
(f) an optionally halogenated $C_{1-6}$ alkyl group,
(g) a mono- or di-$C_{1-6}$ alkyl-amino group,
(h) a $C_{6-14}$ aryl group,
(i) a mono- or di-$C_{6-14}$ aryl-amino group,
(j) a $C_{3-7}$ cycloalkyl group,
(k) a $C_{1-6}$ alkoxy group,
(l) a $C_{1-6}$ alkoxy-$C_{1-6}$ alkoxy group,
(m) a $C_{1-6}$ alkylthio group,
(n) a $C_{1-6}$ alkylsulfinyl group,
(o) a $C_{1-6}$ alkylsulfonyl group,
(p) an optionally esterified carboxy group,
(q) a carbamoyl group,
(r) a thiocarbamoyl group,
(s) a mono- or di-$C_{1-6}$ alkyl-carbamoyl group,
(t) a mono- or di-$C_{6-14}$ aryl-carbamoyl group,
(u) a sulfamoyl group,
(v) a mono- or di-$C_{1-6}$ alkyl-sulfamoyl group, and
(w) a mono- or di-$C_{6-14}$ aryl-sulfamoyl group;
(41) a $C_{1-4}$ alkylenedioxy group optionally substituted by 1 to 3 phenyl;
(42) a mono- or di-($C_{1-6}$ alkyl-carbonyl)-amino group;
(43) an N—$C_{1-6}$ alkyl-N—($C_{1-6}$ alkyl-carbonyl)-amino group;
(44) a formyl group;
(45) an oxo group;
and the like.

Unless otherwise specified, examples of the "optionally substituted amino group" and "optionally substituted carbamoyl group" in the present specification include an "amino group" and "carbamoyl group", each of which optionally has 1 or 2 substituents selected from
(1) an optionally substituted $C_{1-6}$ alkyl group;
(2) an optionally substituted $C_{2-6}$ alkenyl group;
(3) an optionally substituted $C_{2-6}$ alkynyl group;
(4) an optionally substituted $C_{3-7}$ cycloalkyl group;
(5) an optionally substituted $C_{6-14}$ aryl group;
(6) an optionally substituted $C_{1-6}$ alkoxy group;
(7) a $C_{1-6}$ alkyl-carbonyl group;
(8) a heterocyclylcarbonyl group;
(9) a $C_{6-14}$ aryl-carbonyl group;
(10) an optionally substituted heterocyclic group;
(11) a sulfamoyl group;
(12) a mono- or di-$C_{1-6}$ alkyl-sulfamoyl group;
(13) a mono- or di-$C_{6-14}$ aryl-sulfamoyl group; and the like.

When the "optionally substituted amino group" and "optionally substituted carbamoyl group" are an amino group and carbamoyl group, each of which has two substituents, these substituents optionally form, together with the adjacent nitrogen atom, a nitrogen-containing heterocycle.

Examples of the "nitrogen-containing heterocycle" include a 5- to 7-membered nitrogen-containing heterocycle containing, as a ring constituting atom besides carbon atom, at least one nitrogen atom, and optionally further containing 1 or 2 hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

Each symbol used in the formula (I) is explained in detail.

In the formula (I), $R^1$ is a 5- or 6-membered nitrogen-containing heterocyclic group represented by the formula:

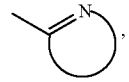

which is optionally substituted.

Examples of the aforementioned "5- or 6-membered nitrogen-containing heterocyclic group" include
(1) a 5- or 6-membered nitrogen-containing heterocyclic group containing 1 to 3 nitrogen atoms;
(2) a 5- or 6-membered nitrogen-containing heterocyclic group containing one nitrogen atom and one or more (preferably 1 or 2) hetero atoms selected from an oxygen atom and a sulfur atom; and
(3) a 5- or 6-membered nitrogen-containing heterocyclic group containing two nitrogen atoms and one hetero atom selected from an oxygen atom and a sulfur atom.

Of these, a 5- or 6-membered nitrogen-containing aromatic heterocyclic group is preferable, and 2-imidazolyl, 4-imidazolyl, 2-thiazolyl, 2-thiadiazolyl, 3-pyrazolyl, 2-pyridyl, 2-pyrazinyl and the like are particularly preferable.

The "5- or 6-membered nitrogen-containing heterocyclic group" optionally has a substitutable number (preferably 1 to 3) of substituent(s) at substitutable position(s).

Examples of the substituent include those similar to the substituent exemplified for the aforementioned "optionally substituted heterocyclic group".

Preferable specific examples of the substituent include
(a) a $C_{1-4}$ alkyl group (preferably methyl, ethyl, isopropyl, isobutyl, tert-butyl) optionally substituted by 1 to 3 substituents selected from
(a1) a hydroxy group,
(a2) a $C_{1-6}$ alkoxy-carbonyl group (preferably ethoxycarbonyl),
(a3) a heterocyclic group (preferably triazolyl, azetidinyl, pyrrolidinyl, imidazolidinyl, 1-oxidothiomorpholinyl, 1,1-dioxidothiomorpholinyl, piperidinyl, piperazinyl, morpholinyl, oxadiazolyl, dihydrooxadiazolyl, diazabicyclo[2.2.1]heptan-2-yl) optionally substituted by 1 to 3 substituents selected from a hydroxy group, a $C_{1-6}$ alkyl group (preferably methyl) optionally substituted by 1 to 3 $C_{6-14}$ aryl groups (preferably phenyl), a $C_{3-6}$ alkyl-carbonyl group (preferably acetyl), an oxo group and a halogen atom (preferably a fluorine atom),
(a4) a mono- or di-$C_{1-6}$ alkyl-amino group (the $C_{1-6}$ alkyl is optionally substituted by 1 to 3 substituents selected from a hydroxy group, a $C_{1-6}$ alkylthio group (preferably ethylthio) and a alkylsulfonyl group (preferably ethylsulfonyl)),
(a5) a nitrogen-containing heterocyclylamino group (preferably azabicyclo[2.2.2]octan-3-ylamino),
(a6) a tert-butyl-diphenylsilyloxy group,
(a7) a $C_{1-6}$ alkyl-carbonyloxy group (preferably acetyloxy) optionally substituted by 1 to 3 substituents selected from an amino group optionally mono- or di-substituted by $C_{1-6}$-alkoxy-carbonyl group(s) (preferably tert-butoxycarbonyl),
(a8) a cyano group,
(a9) a carboxy group, (a10) a heterocyclylcarbonyl group (preferably morpholinocarbonyl, azetidinylcarbonyl),
(a11) a carbamoyl group,
(a12) a mono- or di-$C_{1-6}$ alkyl-carbamoyl group,
(a13) a $C_{1-6}$ alkylsulfonyl group (preferably methylsulfonyl, ethylsulfonyl) optionally substituted by 1 to 3 hydroxy groups,
(a14) a $C_{1-6}$ alkoxy group (preferably methoxy, ethoxy) optionally substituted by 1 to 3 $C_{1-6}$ alkoxy groups (preferably methoxy),
(a15) a halogen atom (preferably a fluorine atom),
(a16) a $C_{3-7}$ cycloalkyl group (preferably cyclobutyl), and
(a17) a tert-butyl-dimethylsilyloxy group,
(b) a heterocyclic group (preferably dioxolanyl, tetrahydropyranyl) optionally substituted by 1 to 3 substituents selected from a hydroxy group and a $C_{1-6}$ alkyl group (preferably methyl),
(c) a halogen atom (preferably a fluorine atom, a chlorine atom, a bromine atom),
(d) a $C_{2-6}$ alkenyl group (preferably vinyl, 2-methyl-1-propenyl) optionally substituted by 1 to 3 $C_{1-6}$ alkoxy-carbonyl groups (preferably ethoxycarbonyl),
(e) a formyl group,
(f) a $C_{1-6}$ alkylthio group (preferably methylthio, ethylthio) optionally substituted by 1 to 3 substituents selected from
   (f1) a hydroxy group,
   (f2) a carboxy group,
   (f3) a $C_{1-6}$ alkoxy group, and
   (f4) a $C_{1-6}$ alkoxy-carbonyl group (preferably ethoxycarbonyl),
(g) a carboxy group,
(h) a $C_{1-6}$ alkoxy group (preferably methoxy, ethoxy, propoxy, isopropoxy, isobutyloxy) optionally substituted by 1 to 3 substituents selected from
   (h1) a $C_{6-14}$ aryl group (preferably phenyl),
   (h2) a $C_{3-7}$ cycloalkyl group (preferably cyclopropyl),
   (h3) a $C_{1-6}$ alkyl-carbonyl group (preferably acetyl), and
   (h4) a hydroxy group,
(i) a hydroxy group,
(j) a $C_{1-6}$ alkoxy-carbonyl group (preferably methoxycarbonyl),
(k) a mono- or di-$C_{3-7}$ cycloalkyl (preferably cyclopropyl)-carbamoyl group,
(l) a mono- or di-$C_{1-6}$ alkyl (preferably ethyl, isobutyl)-carbamoyl group (the $C_{1-6}$ alkyl is optionally substituted by 1 to 3 substituents selected from a hydroxy group and a $C_{1-6}$ alkoxy group (preferably ethoxy)),
(m) a heterocyclylcarbonyl group (preferably morpholinocarbonyl, azetidinylcarbonyl),
(n) a $C_{1-6}$ alkyl-carbonyl group (preferably acetyl),
(o) a carbamoyl group
and the like.

$R^1$ is preferably a 5- or 6-membered nitrogen-containing heterocyclic group represented by the formula:

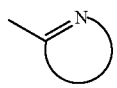

(preferably a 5- or 6-membered nitrogen-containing aromatic heterocyclic group, more preferably 2-imidazolyl, 4-imidazolyl, 2-thiazolyl, 2-thiadiazolyl, 3-pyrazolyl, 2-pyridyl, 2-pyrazinyl) optionally substituted by 1 to 3 substituents selected from (a) a $C_{1-4}$ alkyl group (preferably methyl, ethyl, isopropyl, isobutyl, tert-butyl) optionally substituted by 1 to 3 substituents selected from
   (a1) a hydroxy group,
   (a2) a $C_{1-6}$ alkoxy-carbonyl group (preferably ethoxycarbonyl),
   (a3) a heterocyclic group (preferably triazolyl, azetidinyl, pyrrolidinyl, imidazolidinyl, 1-oxidothiomorpholinyl, 1,1-dioxidothiomorpholinyl, piperidinyl, piperazinyl, morpholinyl, oxadiazolyl, dihydrooxadiazolyl, diazabicyclo[2.2.1]heptan-2-yl) optionally substituted by 1 to 3 substituents selected from a hydroxy group, a $C_{1-6}$ alkyl group (preferably methyl) optionally substituted by 1 to 3 $C_{6-14}$ aryl groups (preferably phenyl), a $C_{1-6}$ alkyl-carbonyl group (preferably acetyl), an oxo group and a halogen atom (preferably a fluorine atom),
   (a4) a mono- or di-$C_{1-6}$ alkyl-amino group (the $C_{1-6}$ alkyl is optionally substituted by 1 to 3 substituents selected from a hydroxy group, a $C_{1-6}$ alkylthio group (preferably ethylthio) and a $C_{1-6}$ alkylsulfonyl group (preferably ethylsulfonyl)),
   (a5) a nitrogen-containing heterocyclylamino group (preferably azabicyclo[2.2.2]octan-3-ylamino),
   (a6) a tert-butyl-diphenylsilyloxy group,
   (a7) a $C_{1-6}$ alkyl-carbonyloxy group (preferably acetyloxy) optionally substituted by 1 to 3 substituents selected from an amino group optionally mono- or di-substituted by $C_{1-6}$ alkoxy-carbonyl group(s) (preferably tert-butoxycarbonyl),
   (a8) a cyano group,
   (a9) a carboxy group,
   (a10) a heterocyclylcarbonyl group (preferably morpholinocarbonyl, azetidinylcarbonyl),
   (a11) a carbamoyl group,
   (a12) a mono- or di-$C_{1-6}$ alkyl-carbamoyl group,
   (a13) a $C_{1-6}$ alkylsulfonyl group (preferably methylsulfonyl, ethylsulfonyl) optionally substituted by 1 to 3 hydroxy groups,
   (a14) a $C_{1-6}$ alkoxy group (preferably methoxy, ethoxy) optionally substituted by 1 to 3 $C_{1-6}$ alkoxy groups (preferably methoxy),
   (a15) a halogen atom (preferably a fluorine atom),
   (a16) a $C_{3-7}$ cycloalkyl group (preferably cyclobutyl), and
   (a17) a tert-butyl-dimethylsilyloxy group,
(b) a heterocyclic group (preferably dioxolanyl, tetrahydropyranyl) optionally substituted by 1 to 3 substituents selected from a hydroxy group and a $C_{1-6}$ alkyl group (preferably methyl),
(c) a halogen atom (preferably a fluorine atom, a chlorine atom, a bromine atom),
(d) a $C_{2-6}$ alkenyl group (preferably vinyl, 2-methyl-1-propenyl) optionally substituted by 1 to 3 $C_{1-6}$ alkoxy-carbonyl groups (preferably ethoxycarbonyl),
(e) a formyl group,
(f) a $C_{1-6}$ alkylthio group (preferably methylthio, ethylthio) optionally substituted by 1 to 3 substituents selected from
   (f1) a hydroxy group,
   (f2) a carboxy group,
   (f3) a $C_{1-6}$ alkoxy group, and
   (f4) a $C_{1-6}$ alkoxy-carbonyl group (preferably ethoxycarbonyl),
(g) a carboxy group, (h) a $C_{1-6}$ alkoxy group (preferably methoxy, ethoxy, propoxy, isopropoxy, isobutyloxy) optionally substituted by 1 to 3 substituents selected from
   (h1) a $C_{6-14}$ aryl group (preferably phenyl),
   (h2) a $C_{3-7}$ cycloalkyl group (preferably cyclopropyl),
   (h3) a $C_{1-6}$ alkyl-carbonyl group (preferably acetyl), and
   (h4) a hydroxy group,
(i) a hydroxy group,
(j) a $C_{1-6}$ alkoxy-carbonyl group (preferably methoxycarbonyl),
(k) a mono- or di-$C_{3-7}$ cycloalkyl (preferably cyclopropyl)-carbamoyl group,
(l) a mono- or di-$C_{1-6}$ alkyl (preferably ethyl, isobutyl)-carbamoyl group (the $C_{1-6}$ alkyl is optionally substituted by 1 to 3 substituents selected from a hydroxy group and a $C_{1-6}$ alkoxy group (preferably ethoxy)),
(m) a heterocyclylcarbonyl group (preferably morpholinocarbonyl, azetidinylcarbonyl),
(n) a $C_{1-6}$ alkyl-carbonyl group (preferably acetyl), and
(o) a carbamoyl group.

$R^1$ is particularly preferably a 5- or 6-membered nitrogen-containing heterocyclic group represented by the formula:

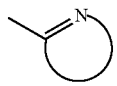

(preferably a 5- or 6-membered nitrogen-containing aromatic heterocyclic group, more preferably 2-thiazolyl, 2-pyridyl) optionally substituted by 1 to 3 $C_{1-4}$ alkyl groups (preferably methyl, isobutyl) optionally substituted by 1 to 3 hydroxy groups.

In the formula (I), $R^2$ is an optionally substituted alkyl group, an optionally substituted 4- to 7-membered cyclic group, —$OR^6$ wherein $R^6$ is an optionally substituted alkyl group or an optionally substituted 4- to 7-membered cyclic group, or an optionally substituted amino group.

In the formula (I), $R^3$ is a hydrogen atom or an optionally substituted alkyl group.

Or, $R^2$ and $R^3$
(i) form, together with the carbon atom they are bonded to, cyclopropane substituted by an optionally substituted 4- to 7-membered cyclic group, or
(ii) in combination form =N—$OR^7$ or =CH—$R^7$ wherein $R^7$ is an optionally substituted alkyl group or an optionally substituted 4- to 7-membered cyclic group.

The "optionally substituted alkyl group" for $R^2$ may be a straight chain or branched chain, and examples thereof include an optionally substituted $C_{1-6}$ alkyl group.

Preferable examples of the substituent that the "alkyl group" of the "optionally substituted alkyl group" for $R^2$ optionally has include an optionally substituted 4- to 7-membered cyclic group, and
(a) a $C_{4-7}$ cycloalkyl group (preferably cyclopentyl) optionally substituted by 1 to 3 substituents selected from
   (a1) a $C_{1-4}$ alkylenedioxy group (preferably ethylenedioxy) optionally substituted by 1 to 3 phenyl groups, and
   (a2) an oxo group,
(b) a 4- to 7-membered (preferably 5- or 6-membered) non-aromatic heterocyclic group (preferably tetrahydrofuranyl, tetrahydropyranyl)
and the like are more preferable.

Examples of the "4- to 7-membered cyclic group" of the "optionally substituted 4- to 7-membered cyclic group" for $R^2$ include a 4- to 7-membered homocyclic group and a 4- to 7-membered heterocyclic group. These rings may be saturated or unsaturated.

Examples of the aforementioned "4- to 7-membered homocyclic group" include a 4- to 7-membered alicyclic hydrocarbon group and phenyl.

Examples of the aforementioned "4- to 7-membered alicyclic hydrocarbon group" include
(1) cycloalkyl group (e.g., cyclobutyl, cyclopentyl, cyclohexyl, cycloheptyl);
(2) a $C_{4-7}$ cycloalkenyl group (e.g., cyclobutenyl, cyclopentenyl, cyclohexenyl, cycloheptenyl); and
(3) a $C_{5-7}$ cycloalkadienyl group (e.g., 2,4-cyclopentadien-1-yl, 2,4-cyclohexadien-1-yl, 2,5-cyclohexadien-1-yl).

Examples of the aforementioned "4- to 7-membered heterocyclic group" include a heterocyclic group containing one or more (preferably 1 to 4, more preferably 1 or 2) hetero atoms selected from an oxygen atom, a sulfur atom, a nitrogen atom and the like.

The "4- to 7-membered heterocyclic group" is preferably a 5- or 6-membered aromatic heterocyclic group or a 4- to 7-membered (preferably 5- or 6-membered) non-aromatic heterocyclic group (preferably tetrahydrofuranyl, tetrahydropyranyl).

The "4- to 7-membered cyclic group" of the "optionally substituted 4- to 7-membered cyclic group" optionally has a substitutable number (preferably 1 to 3) of substituent(s) at substitutable position(s).

Examples of the substituent include those similar to the substituent exemplified for the aforementioned "optionally substituted heterocyclic group". Of these, a $C_{1-4}$ alkylenedioxy group (preferably ethylenedioxy) optionally substituted by 1 to 3 phenyl groups, oxo group and the like are preferable.

The "optionally substituted alkyl group" for $R^6$ may be a straight chain or branched chain, and examples thereof include an optionally substituted $C_{1-6}$ alkyl group.

Examples of the "optionally substituted 4- to 7-membered cyclic group" for $R^6$ include those exemplified as the "optionally substituted 4- to 7-membered cyclic group" for $R^2$.

The "optionally substituted alkyl group" for $R^3$ may be a straight chain or branched chain, and examples thereof include an optionally substituted $C_{1-6}$ alkyl group.

The "cyclopropane substituted by an optionally substituted 4- to 7-membered cyclic group" formed by $R^2$ and $R^3$ together with the carbon atom they are bonded to can be represented by the following formula.

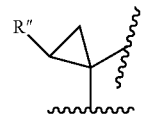

wherein R" is an optionally substituted 4- to 7-membered cyclic group.

Examples of the "optionally substituted 4- to 7-membered cyclic group" of the "cyclopropane substituted by an optionally substituted 4- to 7-membered cyclic group" formed by $R^2$ and $R^3$ together with the carbon atom they are bonded to include those exemplified as the "optionally substituted 4- to 7-membered cyclic group" for $R^2$.

The "cyclopropane" of the "cyclopropane substituted by an optionally substituted 4- to 7-membered cyclic group" optionally has, besides an optionally substituted 4- to 7-membered cyclic group, a substitutable number (preferably 1 to 3) substituent(s) at substitutable position(s).

Examples of the substituent include a halogen atom and an optionally substituted $C_{1-6}$ alkyl group.

Examples of the "optionally substituted alkyl group" for $R^7$ include an optionally substituted $C_{1-6}$ alkyl group.

Examples of the "optionally substituted 4- to 7-membered cyclic group" for $R^7$ include those exemplified as the "optionally substituted 4- to 7-membered cyclic group" for $R^2$.

$R^2$ is preferably an optionally substituted $C_{1-6}$ alkyl group, more preferably a $C_{1-6}$ alkyl group optionally substituted by an optionally substituted 4- to 7-membered cyclic group, more preferably a $C_{1-6}$ alkyl group (preferably methyl) optionally substituted by one substituent selected from (a) a $C_{4-7}$ cycloalkyl group (preferably cyclopentyl) optionally substituted by 1 to 3 substituents selected from (a1) a $C_{1-4}$ alkylenedioxy group (preferably ethylenedioxy) optionally substituted by 1 to 3 phenyl groups, and (a2) an oxo group, and (b) a 4- to 7-membered (preferably 5- or 6-membered) non-aromatic heterocyclic group (preferably tetrahydrofuranyl, tetrahydropyranyl).

$R^2$ is particularly preferably a $C_{1-6}$ alkyl group (preferably methyl) optionally substituted by a 4- to 7-membered (preferably 5- or 6-membered) non-aromatic heterocyclic group (preferably tetrahydropyranyl).

$R^3$ is preferably a hydrogen atom or a $C_{1-6}$ alkyl group (preferably methyl), more preferably a hydrogen atom.

In the formula (I), Cy is an optionally substituted 5-membered cyclic group, which is optionally condensed with an optionally substituted 5- to 7-membered ring.

Examples of the "5-membered cyclic group" of the "optionally substituted 5-membered cyclic group, which is optionally condensed with an optionally substituted 5- to 7-membered ring" for Cy include a 5-membered cyclic group (e.g., cyclopentyl, 2-cyclopenten-1-yl, 3-cyclopenten-1-yl, 2,4-cyclopentadien-1-yl, pyrrolyl, pyrazolyl, imidazolyl, triazolyl, tetrazolyl, thienyl, furyl, thiazolyl, thiadiazolyl, oxazolyl, oxadiazolyl, isoxazolyl, isothiazolyl), from among the "optionally substituted 4- to 7-membered cyclic groups" for $R^2$. Of these, a 5-membered aromatic heterocyclic group (e.g., pyrrolyl, pyrazolyl, imidazolyl, triazolyl, tetrazolyl, thienyl, furyl, thiazolyl, thiadiazolyl, oxazolyl, oxadiazolyl, isoxazolyl, isothiazolyl) is preferable.

The "5-membered cyclic group" is optionally condensed with an optionally substituted 5- to 7-membered ring. Examples of the "5- to 7-membered ring" of the "optionally substituted 5- to 7-membered ring" include a ring (e.g., thiophene, pyrrole, pyrazole, thiazole, benzene, pyridine) corresponding to the 5- to 7-membered cyclic group, from among the group exemplified as the "optionally substituted 4- to 7-membered cyclic groups" for $R^2$.

Preferable specific examples of the "5-membered cyclic group condensed with a 5- to 7-membered ring" of the "5-membered cyclic group condensed with an optionally substituted 5- to 7-membered ring" include pyrazolopyridyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl, benzisothiazolyl and the like.

The "5-membered cyclic group optionally condensed with a 5- to 7-membered ring" of the "optionally substituted 5-membered cyclic group, which is optionally condensed with an optionally substituted 5- to 7-membered ring" for Cy is preferable a 5-membered aromatic heterocyclic group optionally condensed with a 5- to 7-membered ring.

The "5-membered cyclic group" and the "5- to 7-membered ring" each optionally has a substitutable number (preferably 1 to 3) substituent(s) at substitutable position(s). Examples of the substituent include those similar to the substituent exemplified for the aforementioned "optionally substituted heterocyclic group".

Preferable specific examples of the substituent include (a) a $C_{1-6}$ alkylsulfonyl (preferably methylsulfonyl, ethylsulfonyl, propylsulfonyl) optionally substituted by 1 to 3 $C_{1-6}$ alkoxy groups (preferably methoxy), (b) a $C_{3-7}$ cycloalkylsulfonyl (preferably cyclopropylsulfonyl), (c) a $C_{1-6}$ alkoxy-carbonyl group (preferably tert-butoxycarbonyl), (d) a carboxy group, (e) a mono- or di-$C_{3-7}$ cycloalkyl (preferably cyclopropyl)-carbamoyl group, (f) a heterocyclylcarbonyl group (preferably azetidinylcarbonyl), (g) a carbamoyl group di-substituted by a $C_{1-6}$ alkyl group (preferably methyl) and a $C_{1-6}$ alkoxy group (preferably methoxy), (h) a halogen atom (preferably a fluorine atom, a chlorine atom), (i) a $C_{1-6}$ alkylthio group (preferably methylthio), (j) a $C_{1-6}$ alkyl group (preferably methyl), (k) a $C_{1-6}$ alkoxy group (preferably methoxy) and the like.

Cy is preferably a 5-membered aromatic heterocyclic group optionally condensed with an optionally substituted 5- to 7-membered ring (preferably pyrazolyl, imidazolyl, triazolyl, tetrazolyl, thienyl, furyl, thiazolyl, thiadiazolyl, oxazolyl, oxadiazolyl, isoxazolyl, isothiazolyl, pyrazolopyridyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl, benzisothiazolyl etc.) and optionally substituted, more preferably a 5-membered aromatic heterocyclic group optionally condensed with a 5- to 7-membered ring (preferably pyrazolyl, imidazolyl, triazolyl, tetrazolyl, thienyl, furyl, thiazolyl, thiadiazolyl, oxazolyl, oxadiazolyl, isoxazolyl, isothiazolyl, pyrazolopyridyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl, benzisothiazolyl etc.) and optionally substituted by 1 to 3 substituents selected from (a) a $C_{1-6}$ alkylsulfonyl (preferably methylsulfonyl, ethylsulfonyl, propylsulfonyl) optionally substituted by 1 to 3 alkoxy groups (preferably methoxy), (b) a $C_{3-7}$ cycloalkylsulfonyl (preferably cyclopropylsulfonyl), (c) a $C_{1-6}$ alkoxy-carbonyl group (preferably tert-butoxycarbonyl), (d) a carboxy group, (e) a mono- or di-$C_{3-7}$ cycloalkyl (preferably cyclopropyl)-carbamoyl group, (f) a heterocyclylcarbonyl group (preferably azetidinylcarbonyl), (g) a carbamoyl group di-substituted by a $C_{1-6}$ alkyl group (preferably methyl) and a $C_{1-6}$ alkoxy group (preferably methoxy), (h) a halogen atom (preferably a fluorine atom, a chlorine atom), (i) a $C_{1-6}$ alkylthio group (preferably methylthio),
(j) a $C_{1-6}$ alkyl group (preferably methyl), and
(k) a $C_{1-6}$ alkoxy group (preferably methoxy).

Cy is particularly preferably a 5-membered aromatic heterocyclic group optionally condensed with a 5- to 7-membered ring (preferably pyrazolyl, pyrazolopyridyl, indazolyl) and optionally substituted by 1 to 3 substituents selected from
(a) a $C_{1-6}$ alkylsulfonyl group (preferably methylsulfonyl),
(b) a $C_{3-7}$ cycloalkylsulfonyl group (preferably cyclopropylsulfonyl),
(c) a $C_{1-6}$ alkylthio group (preferably methylthio),
(d) a $C_{1-6}$ alkyl group (preferably methyl), and
(e) a $C_{1-6}$ alkoxy group (preferably methoxy).

In the formula (I), $X^1$ and $X^2$ are each independently an optionally substituted carbon atom, or a nitrogen atom.

Examples of the substituent that the "carbon atom" of the "optionally substituted carbon atom" for $X^1$ and $X^2$ optionally has include those similar to the substituent exemplified for the aforementioned "optionally substituted heterocyclic group".

Preferable examples of the substituent that the "carbon atom" of the "optionally substituted carbon atom" for $X^1$ optionally has include
(a) a $C_{1-6}$ alkoxy-carbonyl group (preferably ethoxycarbonyl),
(b) a carboxy group,
(c) a carbamoyl group,
(d) a mono- or di-$C_{1-6}$ alkyl-carbamoyl group,
(e) a cyano group,
(f) a mono- or di-($C_{1-6}$ alkoxy-carbonyl (preferably methoxycarbonyl))-amino group,
(g) a halogen atom (preferably a fluorine atom, a chlorine atom, an iodine atom)
and the like.

Preferable examples of the substituent that the "carbon atom" of the "optionally substituted carbon atom" for $X^2$ optionally has include
(a) a halogen atom (preferably a fluorine atom, a chlorine atom, a bromine atom),
(b) a $C_{1-4}$ alkyl group (preferably methyl) optionally substituted by 1 to 3 $C_{1-6}$ alkoxy-carbonyl groups (preferably ethoxycarbonyl)
and the like.

The following combination of $X^1$ and $X^2$ is preferable;
(1) $X^1$ is an optionally substituted carbon atom, and $X^2$ is an optionally substituted carbon atom
[preferably
$X^1$ is a carbon atom optionally substituted by one substituent selected from
(a) a $C_{1-6}$ alkoxy-carbonyl group (preferably ethoxycarbonyl),
(b) a carboxy group,
(c) a carbamoyl group,
(d) a mono- or di-$C_{1-6}$ alkyl-carbamoyl group,
(e) a cyano group,
(f) a mono- or di-($C_{1-6}$ alkoxy-carbonyl (preferably methoxycarbonyl))-amino group, and
(g) a halogen atom (preferably a fluorine atom, a chlorine atom, an iodine atom), and
$X^2$ is a carbon atom optionally substituted by one substituent selected from
(a) a halogen atom (preferably a fluorine atom, a chlorine atom, a bromine atom), and
(b) a $C_{1-4}$ alkyl group (preferably methyl) optionally substituted by 1 to 3 $C_{1-6}$ alkoxy-carbonyl groups (preferably ethoxycarbonyl)]; or (2) $X^1$ is a nitrogen atom, and $X^2$ is an optionally substituted carbon atom
[preferably
$X^1$ is a nitrogen atom, and
$X^2$ is a carbon atom optionally substituted by one substituent selected from
(a) a halogen atom (preferably a fluorine atom, a chlorine atom, a bromine atom), and
(b) a $C_{1-4}$ alkyl group (preferably methyl) optionally substituted by 1 to 3 $C_{1-6}$ alkoxy-carbonyl groups (preferably ethoxycarbonyl)].

Of these, $X^1$ and $X^2$ are preferably both optionally substituted carbon atoms, particularly preferably both CH.

Of compound (I), a compound wherein Cy is not 1H-pyrrol-2-yl is novel.

Preferable specific examples of the compound represented by the formula (I) include the following compounds.
(Compound A1)
Compound (I) wherein
$R^1$ is a 5- or 6-membered nitrogen-containing heterocyclic group represented by the formula:

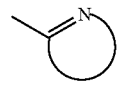

(preferably a 5- or 6-membered nitrogen-containing aromatic heterocyclic group, more preferably 2-imidazolyl, 4-imidazolyl, 2-thiazolyl, 2-thiadiazolyl, 3-pyrazolyl, 2-pyridyl, 2-pyrazinyl) optionally substituted by 1 to 3 substituents selected from
(a) a $C_{1-4}$ alkyl group (preferably methyl, ethyl, isopropyl, isobutyl, tert-butyl) optionally substituted by 1 to 3 substituents selected from
(a1) a hydroxy group,
(a2) a $C_{1-6}$ alkoxy-carbonyl group (preferably ethoxycarbonyl),
(a3) a heterocyclic group (preferably triazolyl, azetidinyl, pyrrolidinyl, imidazolidinyl, 1-oxidothiomorpholinyl, 1,1-dioxidothiomorpholinyl, piperidinyl, piperazinyl, morpholinyl, oxadiazolyl, dihydrooxadiazolyl, diazabicyclo[2.2.1]heptan-2-yl) optionally substituted by 1 to 3 substituents selected from a hydroxy group, a $C_{1-6}$ alkyl group (preferably methyl) optionally substituted by 1 to 3 $C_{6-14}$ aryl groups (preferably phenyl), a $C_{1-6}$ alkyl-carbonyl group (preferably acetyl), an oxo group and a halogen atom (preferably a fluorine atom),
(a4) a mono- or di-$C_{1-6}$ alkyl-amino group (the $C_{1-6}$ alkyl is optionally substituted by 1 to 3 substituents selected from a hydroxy group, a $C_{1-6}$ alkylthio group (preferably ethylthio) and a $C_{1-6}$ alkylsulfonyl group (preferably ethylsulfonyl)),
(a5) a nitrogen-containing heterocyclylamino group (preferably azabicyclo[2.2.2]octan-3-yl-amino),
(a6) a tert-butyl-diphenylsilyloxy group,
(a7) a $C_{1-6}$ alkyl-carbonyloxy group (preferably acetyloxy) optionally substituted by 1 to 3 substituents selected from an amino group optionally mono- or di-substituted by $C_{1-6}$ alkoxy-carbonyl group(s) (preferably tert-butoxycarbonyl),
(a8) a cyano group,
(a9) a carboxy group,
(a10) a heterocyclylcarbonyl group (preferably morpholinocarbonyl, azetidinylcarbonyl), (a11) a carbamoyl group,
(a12) a mono- or di-$C_{1-6}$ alkyl-carbamoyl group,
(a13) a $C_{1-6}$ alkylsulfonyl group (preferably methylsulfonyl, ethylsulfonyl) optionally substituted by 1 to 3 hydroxy groups,
(a14) a $C_{1-6}$ alkoxy group (preferably methoxy, ethoxy) optionally substituted by 1 to 3 $C_{1-6}$ alkoxy groups (preferably methoxy),
(a15) a halogen atom (preferably a fluorine atom),
(a16) a $C_{3-7}$ cycloalkyl group (preferably cyclobutyl), and
(a17) a tert-butyl-dimethylsilyloxy group,
(b) a heterocyclic group (preferably dioxolanyl, tetrahydropyranyl) optionally substituted by 1 to 3 substituents selected from a hydroxy group and a $C_{1-6}$ alkyl group (preferably methyl),
(c) a halogen atom (preferably a fluorine atom, a chlorine atom, a bromine atom),
(d) a $C_{2-6}$ alkenyl group (preferably vinyl, 2-methyl-1-propenyl) optionally substituted by 1 to 3 $C_{1-6}$ alkoxy-carbonyl groups (preferably ethoxycarbonyl),
(e) a formyl group,
(f) a $C_{1-6}$ alkylthio group (preferably methylthio, ethylthio) optionally substituted by 1 to 3 substituents selected from
(f1) a hydroxy group,
(f2) a carboxy group,
(f3) a $C_{1-6}$ alkoxy group, and
(f4) a $C_{1-6}$ alkoxy-carbonyl group (preferably ethoxycarbonyl),
(g) a carboxy group,
(h) a $C_{1-6}$ alkoxy group (preferably methoxy, ethoxy, propoxy, isopropoxy, isobutyloxy) optionally substituted by 1 to 3 substituents selected from
(h1) a $C_{6-14}$ aryl group (preferably phenyl),
(h2) a $C_{3-7}$ cycloalkyl group (preferably cyclopropyl),
(h3) a $C_{1-6}$ alkyl-carbonyl group (preferably acetyl), and
(h4) a hydroxy group,
(i) a hydroxy group,
(j) a $C_{1-6}$ alkoxy-carbonyl group (preferably methoxycarbonyl),
(k) a mono- or di-$C_{3-7}$ cycloalkyl (preferably cyclopropyl)-carbamoyl group,
(l) a mono- or di-$C_{1-6}$ alkyl (preferably ethyl, isobutyl)-carbamoyl group (the $C_{1-6}$ alkyl is optionally substituted by 1 to 3 substituents selected from a hydroxy group and a $C_{1-6}$ alkoxy group (preferably ethoxy)),
(m) a heterocyclylcarbonyl group (preferably morpholinocarbonyl, azetidinylcarbonyl),
(n) a $C_{1-6}$ alkyl-carbonyl group (preferably acetyl), and
(o) a carbamoyl group;
$R^2$ is a $C_{1-6}$ alkyl group (preferably methyl) optionally substituted by one substituent selected from
(a) a $C_{4-7}$ cycloalkyl group (preferably cyclopentyl) optionally substituted by 1 to 3 substituents selected from
(a1) a $C_{1-4}$ alkylenedioxy group (preferably ethylenedioxy) optionally substituted by 1 to 3 phenyl groups, and
(a2) an oxo group, and
(b) a 4- to 7-membered (preferably 5- or 6-membered) non-aromatic heterocyclic group (preferably tetrahydrofuranyl, tetrahydropyranyl);
$R^3$ is a hydrogen atom or a $C_{1-6}$ alkyl group (preferably methyl);
Cy is a 5-membered aromatic heterocyclic group optionally condensed with a 5- to 7-membered ring (preferably pyrazolyl, imidazolyl, triazolyl, tetrazolyl, thienyl, furyl, thiazolyl, thiadiazolyl, oxazolyl, oxadiazolyl, isoxazolyl, isothiazolyl, pyrazolopyridyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl, benzisothiazolyl etc.) and optionally substituted by 1 to 3 substituents selected from
(a) a $C_{1-6}$ alkylsulfonyl group (preferably methylsulfonyl, ethylsulfonyl, propylsulfonyl) optionally substituted by 1 to 3 $C_{1-6}$ alkoxy groups (preferably methoxy),
(b) a $C_{3-7}$ cycloalkylsulfonyl group (preferably cyclopropylsulfonyl),
(c) a $C_{1-6}$ alkoxy-carbonyl group (preferably tert-butoxycarbonyl),
(d) a carboxy group,
(e) a mono- or di-$C_{3-7}$ cycloalkyl (preferably cyclopropyl)-carbamoyl group,
(f) a heterocyclylcarbonyl group (preferably azetidinylcarbonyl),
(g) a carbamoyl group di-substituted by a $C_{1-6}$ alkyl group (preferably methyl) and a $C_{1-6}$ alkoxy group (preferably methoxy),
(h) a halogen atom (preferably a fluorine atom, a chlorine atom),
(i) a $C_{1-6}$ alkylthio group (preferably methylthio),
(j) a $C_{1-6}$ alkyl group (preferably methyl), and
(k) $C_{1-6}$ alkoxy group (preferably methoxy);
$X^1$ is
(1) a carbon atom optionally substituted by one substituent selected from
(a) a $C_{1-6}$ alkoxy-carbonyl group (preferably ethoxycarbonyl),
(b) a carboxy group,
(c) a carbamoyl group,
(d) a mono- or di-$C_{1-6}$ alkyl-carbamoyl group,
(e) a cyano group,
(f) a mono- or di-($C_{1-6}$ alkoxy-carbonyl (preferably methoxycarbonyl))-amino group, and
(g) a halogen atom (preferably a fluorine atom, a chlorine atom, an iodine atom), or
(2) a nitrogen atom; and
$X^2$ is a carbon atom optionally substituted by one substituent selected from
(a) a halogen atom (preferably a fluorine atom, a chlorine atom, a bromine atom), and
(b) a $C_{1-4}$ alkyl group (preferably methyl) optionally substituted by 1 to 3 $C_{1-6}$ alkoxy-carbonyl groups (preferably ethoxycarbonyl).
(Compound a2)
Compound (A1) wherein
$X^1$ is
(1) a carbon atom optionally substituted by one substituent selected from
(a) a $C_{1-6}$ alkoxy-carbonyl group (preferably ethoxycarbonyl),
(b) a carboxy group,
(c) a carbamoyl group,
(d) a mono- or di-$C_{1-6}$ alkyl-carbamoyl group,
(e) a cyano group,
(f) a mono- or di-($C_{1-6}$ alkoxy-carbonyl (preferably methoxycarbonyl))-amino group, and
(g) a halogen atom (preferably a fluorine atom, a chlorine atom, an iodine atom); and $X^2$ is a carbon atom optionally substituted by one substituent selected from,
(a) a halogen atom (preferably a fluorine atom, a chlorine atom, a bromine atom), and
(b) a $C_{1-4}$ alkyl group (preferably methyl) optionally substituted by 1 to 3 $C_{1-6}$ alkoxy-carbonyl groups (preferably ethoxycarbonyl).
(Compound A3)
Compound (A1) wherein
$X^1$ is a nitrogen atom; and
$X^2$ is a carbon atom optionally substituted by one substituent selected from,
(a) a halogen atom (preferably a fluorine atom, a chlorine atom, a bromine atom), and
(b) a $C_{1-4}$ alkyl group (preferably methyl) optionally substituted by 1 to 3 $C_{1-6}$ alkoxy-carbonyl groups (preferably ethoxycarbonyl).
(Compound A4)
Compound (I) wherein
$R^1$ is a 5- or 6-membered nitrogen-containing heterocyclic group represented by the formula:

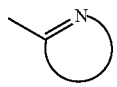

(preferably a 5- or 6-membered nitrogen-containing aromatic heterocyclic group, more preferably 2-thiazolyl, 2-pyridyl) optionally substituted by 1 to 3 $C_{1-4}$ alkyl groups (preferably methyl, isobutyl) optionally substituted by 1 to 3 hydroxy groups;
$R^2$ is a $C_{1-6}$ alkyl group (preferably methyl) optionally substituted by a 4- to 7-membered (preferably 5- or 6-membered) non-aromatic heterocyclic group (preferably tetrahydropyranyl);
$R^3$ is a hydrogen atom;
Cy is a 5-membered aromatic heterocyclic group optionally condensed with a 5- to 7-membered ring (preferably pyrazolyl, pyrazolopyridyl, indazolyl) and optionally substituted by 1 to 3 substituents selected from
(a) a $C_{1-6}$ alkylsulfonyl group (preferably methylsulfonyl),
(b) a $C_{3-7}$ cycloalkylsulfonyl group (preferably cyclopropylsulfonyl),
(c) a $C_{1-6}$ alkylthio group (preferably methylthio),
(d) a $C_{1-6}$ alkyl group (preferably methyl), and
(e) a $C_{1-6}$ alkoxy group (preferably methoxy);
$X^1$ is CH; and
$X^2$ is CH.

The salt of compound (I) is preferably a pharmacologically acceptable salt, and examples thereof include a salt with inorganic base, a salt with organic base, a salt with inorganic acid, a salt with organic acid, a salt with basic or acidic amino acid and the like.

Preferable examples of the salt with inorganic base include alkali metal salts such as sodium salt, potassium salt and the like; alkaline earth metal salts such as calcium salt, magnesium salt and the like; and aluminum salts; ammonium salts and the like.

Preferable examples of the salt with organic base include salts with trimethylamine, triethylamine, pyridine, picoline, ethanolamine, diethanolamine, triethanolamine, dicyclohexylamine, N,N-dibenzylethylenediamine and the like.

Preferable examples of the salt with inorganic acid include salt with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

A prodrug of the compound (I) means a compound which is converted to the compound (I) with a reaction due to an enzyme, an gastric acid, etc. under the physiological condition in the living body, that is, a compound which is converted to the compound (I) by enzymatic oxidation, reduction, hydrolysis and the like; a compound which is converted to the compound (I) by hydrolysis and the like due to gastric acid and the like. A prodrug of the compound (I) may be a compound obtained by subjecting an amino group in the compound (I) to an acylation, alkylation or phosphorylation (e.g., a compound obtained by subjecting an amino group in the compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in the compound (I) to an acylation, alkylation, phosphorylation or boration (e.g., a compound obtained by subjecting an hydroxy group in the compound (I) to an acetylation, palmitoylation, propanoylation, pivaloylation, succinylation, fumarylation, alanylation or dimethylaminomethylcarbonylation, etc.); a compound obtained by subjecting a carboxyl group in the compound (I) to an esterification or amidation (e.g., a compound obtained by subjecting a carboxyl group in the compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation etc.) and the like. These compounds can be produced from the compound (I) according to a method known per se.

A prodrug of the compound (I) may also be one which is converted into the compound (I) under a physiological condition, such as those described in *IYAKUHIN NO KAIHATSU (Development of Pharmaceuticals)*, Vol. 7, Design of Molecules, p. 163-198, Published by HIROKAWA SHOTEN (1990).

The compound (I) may be labeled with an isotope (e.g., $^3H$, $^{14}C$, $^{35}S$, $^{125}I$ etc.) and the like.

Deuterium-converted compound wherein $^1H$ has been converted to $^2H(D)$ are also encompassed in the compound (I).

Moreover, tautomer is present in a compound represented by the formula (I) and a salt thereof. Any of tautomers is encompassed in the present invention, and a compound represented by the formula (I) and a salt thereof may be a solvate, a hydrate, a non-solvate or a non-hydrate.

The compound (I) or a prodrug thereof (hereinafter sometimes to be abbreviated as the compound of the present invention) shows low toxicity and can be used as an agent for the prophylaxis or treatment of various diseases to be mentioned below for mammals (e.g., humans, mice, rats, rabbits, dogs, cats, bovines, horses, pigs, monkeys etc.) as they are or by admixing with a pharmacologically acceptable carrier and the like to give a pharmaceutical composition.

Here, various organic or inorganic carriers conventionally used as materials for pharmaceutical preparations are used as a pharmacologically acceptable carrier, which are added as excipient, lubricant, binder and disintegrant for solid preparations; or solvent, solubilizing agent, suspending agent, isotonicity agent, buffer and soothing agent for liquid preparations, and the like. Where necessary, an additive for pharmaceutical preparations such as preservative, antioxidant, colorant, sweetening agent and the like can be used.

Preferable examples of the excipient include lactose, sucrose, D-mannitol, D-sorbitol, starch, α-starch, dextrin, crystalline cellulose, low-substituted hydroxypropylcellulose, sodium carboxymethylcellulose, gum acacia, pullulan, light anhydrous silicic acid, synthetic aluminum silicate, magnesium aluminate metasilicate and the like.

Preferred examples of the lubricant include magnesium stearate, calcium stearate, talc, colloidal silica and the like.

Preferable examples of the binder include α-starch, saccharose, gelatin, gum acacia, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, calcium carboxymethylcellulose, sodium croscarmellose, sodium carboxymethylstarch, light anhydrous silicic acid, low-substituted hydroxypropylcellulose and the like.

Preferable examples of the solvent include water for injection, physiological brine, Ringer's solution, alcohol, propylene glycol, polyethylene glycol, sesame oil, corn oil, olive oil, cottonseed oil and the like.

Preferred examples of the solubilizing agent include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferred examples of the suspending agent include surfactants such as stearyltriethanolamine, sodium lauryl sulfate, lauryl aminopropionate, lecithin, benzalkonium chloride, benzethonium chloride, glyceryl monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, polyoxyethylene hydrogenated castor oil and the like.

Preferred examples of the isotonicity agent include sodium chloride, glycerol, D-mannitol, D-sorbitol, glucose and the like.

Preferred examples of the buffer include buffers such as phosphate, acetate, carbonate, citrate and the like.

Preferred examples of the soothing agent include benzyl alcohol and the like.

Preferred examples of the preservative include p-oxybenzoates, chlorobutanol, benzyl alcohol, phenethyl alcohol, dehydroacetic acid, sorbic acid and the like.

Preferred examples of the antioxidant include sulfite, ascorbate and the like.

Preferable examples of the colorant include water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment), natural pigments (e.g., beta carotene, chlorophil, ferric oxide red) and the like.

Preferable examples of the sweetening agent include saccharin sodium, dipotassium glycyrrhizinate, aspartame, stevia and the like.

The dosage form of the aforementioned pharmaceutical composition is, for example, an oral agent such as tablets (inclusive of sublingual tablets and orally disintegrable tablets), capsules (inclusive of soft capsules and microcapsules), granules, powders, troches, syrups, emulsions, suspensions and the like; a parenteral agent such as injections (e.g., subcutaneous injections, intravenous injections, intramuscular injections, intraperitoneal injections, drip infusions), external agents (e.g., transdermal preparations, ointments), suppositories (e.g., rectal suppositories, vaginal suppositories), pellets, nasal preparations, pulmonary preparations (inhalations), ophthalmic preparations and the like, and the like. These may be administered safely via an oral or parenteral (e.g., topical, rectal, intravenous administrations etc.) route.

These agents may be controlled-release preparations such as rapid-release preparations and sustained-release preparations (e.g., sustained-release microcapsules).

The pharmaceutical composition can be produced according to a method conventionally used in the field of pharmaceutical preparation, such as the method described in Japan Pharmacopoeia and the like. Concrete production methods of preparations are described in detail in the following.

While the content of the compound of the present invention in the pharmaceutical composition varies depending on the dosage form, dose of the compound of the present invention and the like, it is, for example, about 0.1 to 100 wt %.

The compound of the present invention has a superior GK activating action, and can be used as an agent for the prophylaxis or treatment of various diseases for mammals (e.g., human, bovine, horse, dog, cat, monkey, mouse, rat, specifically human). In addition, as the compound of the present invention has a selective GK activating action, it shows low toxicity (e.g., acute toxicity, chronic toxicity, cardiotoxicity, carcinogenic, genetic toxicity), which causes fewer side effects.

The compound of the present invention can be used as an agent for the prophylaxis or treatment of diabetes (e.g., type-1 diabetes, type-2 diabetes, gestational diabetes, obese diabetes etc.); an agent for the prophylaxis or treatment of hyperlipidemia (e.g., hypertriglyceridemia, hypercholesterolemia, hypo-HDL-emia, postprandial hyperlipidemia etc.); an agent for the prophylaxis or treatment of arteriosclerosis; an agent for the prophylaxis or treatment of impaired glucose tolerance (IGT); and an agent for preventing progression of impaired glucose tolerance into diabetes.

For diagnostic criteria of diabetes, Japan Diabetes Society reported new diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported new diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 100 mg/dl and less than 126 mg/dl is called IFG (Impaired Fasting Glucose). According to the report of WHO, among the IFG (Impaired Fasting Glucose), a condition showing a 75 g oral glucose tolerance test 2 h level (glucose concentration of intravenous plasma) of not less than 110 mg/dl and less than 126 mg/dl is called IFG (Impaired Fasting Glycaemia).

The compound of the present invention can also be used as an agent for the prophylaxis or treatment of diabetes, borderline type, impaired glucose tolerance, IFG (Impaired Fasting Glucose) and IFG (Impaired Fasting Glycaemia), as determined according to the above-mentioned new diagnostic criteria. Moreover, the compound of the present invention can prevent progress of borderline type, impaired glucose tolerance, IFG (Impaired Fasting Glucose) or IFG (Impaired Fasting Glycaemia) into diabetes.

The compound of the present invention can also be used as an agent for the prophylaxis or treatment of, for example, diabetic complications [e.g., neuropathy, nephropathy, retinopathy, cataract, macroangiopathy, osteopenia, hyperosmolar diabetic coma, infectious disease (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], obesity, osteoporosis, cachexia (e.g., cancerous cachexia, tuberculous cachexia, diabetic cachexia, blood disease cachexia, endocrine disease cachexia, infectious disease cachexia or cachexia due to acquired immunodeficiency syndrome), fatty liver, hypertension, polycystic ovary syndrome, kidney disease (e.g., diabetic nephropathy, glomerular nephritis, glomerulosclerosis, nephrotic syndrome, hypertensive nephrosclerosis, end stage kidney disease), muscular dystrophy, myocardial infarction, angina pectoris, cerebrovascular accident (e.g., cerebral infarction, cerebral apoplexy), abnormal sugar metabolism, abnormal lipid metabolism, insulin resistance syndrome, Syndrome X, metabolic syndrome (state concurrently associated with at least one of type 2 diabetes, impaired glucose tolerance and insulin resistance, and at least two from obesity, abnormal lipid metabolism, hypertension and trace albumin urine), Cushing's syndrome, hyperinsulinemia, hyperinsulinemia-induced sensory disorder, tumor (e.g., leukemia, breast cancer, prostate cancer, skin cancer), irritable bowel syndrome, acute or chronic diarrhea, inflammatory diseases (e.g., rheumatoid arthritis, spondylitis deformans, osteoarthritis, lumbago, gout, postoperative or traumatic inflammation, swelling, neuralgia, pharyngolaryngitis, cystitis, hepatitis (inclusive of non-alcoholic steatohepatitis), pneumonia, pancreatitis, inflammatory intestine disease, ulcerative colitis, stomach mucous membrane injury (including stomach mucous membrane injury caused by aspirin)), visceral fat syndrome and the like.

The compound of the present invention can also be used for improvement of insulin resistance, promotion or increase of insulin secretion, decrease of visceral fat, suppression of accumulation of visceral fat, improvement of sugar metabolism, improvement of lipid metabolism (suppression of oxidative LDL production, improvement of lipoprotein metabolism), improvement of coronary metabolism, prophylaxis or treatment of cardiovascular complication, prophylaxis or treatment of heart failure complication, lowering of blood remnant, prophylaxis or treatment of anovulation, prophylaxis or treatment of hirsutism, prophylaxis or treatment of hyperandrogenism, improvement of pancreatic (β cell) function, regeneration of pancreas (β cell), promotion of regeneration of pancreas (β cell) and the like.

The compound of the present invention can also be used for the secondary prevention and suppression of progression of various diseases mentioned above (e.g., cardiovascular event such as myocardial infarction etc.).

The compound of the present invention is particularly useful as an agent for the prophylaxis or treatment of type-2 diabetes, obese diabetes and the like.

While the dose of the compound of the present invention varies depending on the administration subject, administration route, target disease, condition and the like, the compound of the present invention is generally given in a single dose of about 0.01-100 mg/kg body weight, preferably 0.05-30 mg/kg body weight, more preferably 0.1-10 mg/kg body weight, in the case of, for example, oral administration to adult diabetic patients. This dose is desirably given 1 to 3 times a day.

The compound of the present invention can be used in combination with drugs such as a therapeutic agent for diabetes, a therapeutic agent for diabetic complications, a therapeutic agent for hyperlipidemia, an antihypertensive agent, an antiobestic agent, a diuretic, a chemotherapeutic agent, an immunotherapeutic agent, an antithrombotic agent, a therapeutic agent for osteoporosis, a antidementia agent, an erectile dysfunction improver, a therapeutic agent for pollakiuria or urinary incontinence, a therapeutic agent for dysuria and the like (hereinafter to be referred to as a combination drug). In this case, the timing of administration of the compound of the present invention and a combination drug is not limited. These may be simultaneously administered to an administration subject or administered in a staggered manner. Moreover, the compound of the present invention and a combination drug may be administered as two kinds of preparations each containing an active ingredient, or may be administered as a single preparation containing both active ingredients.

The dose of the combination drug can be determined as appropriate based on the dose clinically employed. The proportion of the compound of the present invention and the combination drug can be appropriately determined depending on the administration subject, administration route, target disease, condition, combination and the like. When, for example, the administration subject is human, the combination drug is used in an amount of 0.01-100 parts by weight per 1 part by weight of the compound of the present invention.

Examples of the therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Reglixane (JTT-501), Netoglitazone (MCC-555), DRF-2593, Edaglitazone (BM-13.1258), KRP-297, R-119702, Rivoglitazone (CS-011), FK-614, compound described in WO99/58510 (e.g., (E)-4-[4-(5-methyl-2-phenyl-4-oxazolylmethoxy)benzyloxyimino]-4-phenylbutyric acid), compound described in WO01/38325, Tesaglitazar (AZ-242), Ragaglitazar (N,N-622), Muraglitazar (BMS-298585), ONO-5816, LM-4156, MBX-102, Naveglitazar (LY-519818), MX-6054, LY-510929, Balaglitazone (N,N-2344), T-131 or a salt thereof, THR-0921), PPARγ agonists, PPARγ antagonists, PPARγ/α dual agonists, α-glucosidase inhibitors (e.g., voglibose, acarbose, miglitol, emiglitate), biguanides (e.g., phenformin, metformin, buformin or a salt thereof (e.g., hydrochloride, fumarate, succinate)), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, senaglinide, nateglinide, mitiglinide or a calcium salt hydrate thereof], GPR40 agonists, GLP-1 receptor agonists [e.g., GLP-1, GLP-1MR agent, N,N-2211, AC-2993 (exendin-4), BIM-51077, Aib(8,35)hGLP-1(7,37)NH$_2$, CJC-1131], amylin agonists (e.g., pramlintide), phosphotyrosine phosphatase inhibitors (e.g., sodium vanadate), dipeptidyl peptidase IV inhibitors (e.g., Alogliptin or a salt thereof (preferably benzoate), NVP-DPP-278, PT-100, P32/98, Vidagliptin(LAF-237), P93/01, TS-021, MK-431, Saxagliptin (BMS-477118)), P3 agonists (e.g., AJ-9677), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), 11β-HSD1 inhibitors (e.g., BVT-3498), adiponectin or an agonist thereof, IKK inhibitors (e.g., AS-2868), leptin resistance improving drugs, somatostatin receptor agonists (e.g., compound described in WO01/25228, WO03/42204, WO98/44921, WO98/45285, WO99/22735) and the like.

Examples of the therapeutic agents for diabetic complications include aldose reductase inhibitors (e.g., Tolrestat, Epalrestat, Zenarestat, Zopolrestat, Minalrestat, Fidarestat, CT-112, ranirestat (AS-3201)), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole)), stimulators (e.g., Y-128), PKC inhibitors (e.g., ruboxistaurin mesylate), AGE inhibitors (e.g., ALT-946, pimagedine, N-phenacylthiazolium bromide (ALT-766), ALT-711, EXO-226, Pyridorin, Pyridoxamine), active oxygen scavengers (e.g., thioctic acid), cerebral vasodilators (e.g., tiapuride, mexiletine), somatostatin receptor agonists (81M23190), apoptosis signal regulating kinase-1 (ASK-1) inhibitors and the like.

Examples of the therapeutic agents for hyperlipidemia include HMG-CoA reductase inhibitors (e.g., pravastatin, simvastatin, lovastatin, atorvastatin, fluvastatin, pitavastatin, rosuvastatin and salts thereof (e.g., sodium salt, calcium salt)), squalene synthase inhibitors (e.g., compound described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), ACAT inhibitors (e.g., Avasimibe, Eflucimibe), anion exchange resins (e.g., colestyramine), probucol, nicotinic acid drugs (e.g., nicomol, niceritrol), ethyl icosapentate, phytosterols (e.g., soysterol, γ-oryzanol) and the like.

Examples of the antihypertensive agents include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobesity agents include antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compound described in WO01/82925 and WO01/87834); neuropeptide Y antagonists (e.g., CP-422935); cannabinoid receptor antagonists (e.g., SR-141716, SR-147778); ghrelin antagonists), pancreatic lipase inhibitors (e.g., orlistat, ATL-962), β3 agonists (e.g., AJ-9677), peptide anorexiants (e.g., leptin, CNTF (Ciliary Neurotropic Factor)), cholecystokinin agonists (e.g., lintitript, FPL-15849), anorexigenic agents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil and derivatives thereof), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antithrombotic agents include heparin (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, risedronate disodium, pamidronate disodium, alendronate sodium hydrate, incadronate disodium and the like.

Examples of the antidementia agents include tacrine, donepezil, rivastigmine, galanthamine and the like.

Examples of the erectile dysfunction improvers include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

The combination drug is preferably insulin preparation, insulin sensitizer, α-glucosidase inhibitor, biguanide, insulin secretagogue (preferably sulfonylurea) and the like.

Two or more kinds of the above-mentioned combination drugs may be used in an appropriate combination.

When the compound of the present invention is used in combination with a combination drug, the amount thereof can be reduced within a safe range in consideration of counteraction of these agents. Particularly, the dose of an insulin sensitizer, an insulin secretagogue (preferably a sulfonylurea) and a biguanide can be reduced as compared with the normal dose. Therefore, an adverse effect which may be caused by these agents can be prevented safely. In addition, the dose of the therapeutic agent for diabetic complications, therapeutic agent for hyperlipidemia and antihypertensive agent can be reduced whereby an adverse effect which may be caused by these agents can be prevented effectively.

Compound (I) can be produced, for example, according to the method shown in the following Reaction Schemes or a method analogous thereto.

Of the compound represented by the formula (I), the pyrrole derivative can be produced, for example, according to the method shown in the following Reaction Scheme 2.

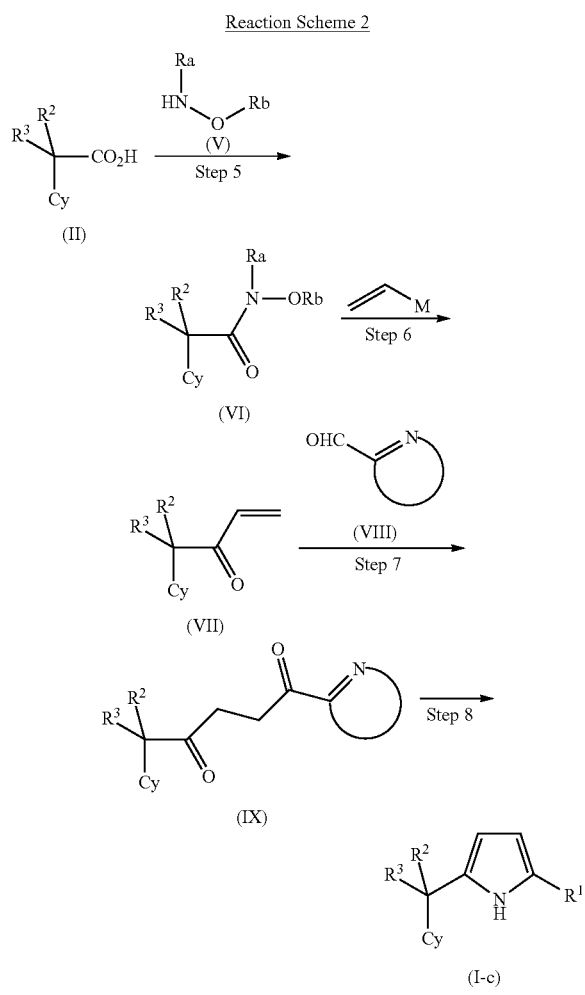

wherein Ra and Rb are each an optionally substituted alkyl group, M is a metal atom or a halogenated metal, and the other symbols are as defined above.

In this scheme, compound (II) is reacted with hydroxylamine compound (V) or a salt thereof to produce compound (VI), compound (VI) is reacted with an alkenyl metal reagent to produce enone compound (VII), compound (VII) is reacted with aldehyde compound (VIII) to produce diketone compound (IX), and compound (IX) is subjected to a ring-closing reaction to produce compound (I-c).

Compound (II) can be synthesized, for example, according to the known method described in WO00/58293, WO2006/016178 or the like.

Compound (V) can be synthesized according to a known method.

Compound (VIII) can be synthesized according to a known method.

Step 5

In this step, compound (VI) is produced by reacting compound (II) or a reactive derivative of the carboxy group or a salt thereof with hydroxylamine compound (V) or a salt thereof.

Examples of the reactive derivative of the carboxy group of compound (II) include 1) an acid chloride;
2) an acid azide;
3) a mixed anhydride with an acid (e.g., substituted phosphoric acid such as dialkyl phosphate, phenyl phosphate, diphenyl phosphate, dibenzyl phosphate, halogenated phosphoric acid and the like; dialkyl phosphonate; sulfurous acid; thiosulfuric acid; sulfuric acid; sulfonic acids such as methanesulfonic acid and the like; aliphatic carboxylic acids such as formic acid, acetic acid, propionic acid, butyric acid, isobutyric acid, pivalic acid, pentanoic acid, isopentanoic acid, trichloroacetic acid and the like; aromatic carboxylic acids such as benzoic acid and the like);
4) a symmetric anhydride;
5) an activated amide with imidazole, 4-substituted imidazole, dimethylpyrazole, triazole or tetrazole;
6) an activated ester such as cyanomethyl ester, methoxymethyl ester, dimethyliminomethyl ester, vinyl ester, propargyl ester, p-nitrophenyl ester, trichlorophenyl ester, pentachlorophenyl ester, mesylphenyl ester, phenylazophenyl ester, phenyl thioester, p-nitrophenyl ester, p-cresyl thioester, carboxymethyl thioester, pyranyl ester, pyridyl ester, piperidyl ester, 8-quinolyl thioester and the like;
7) an ester with a N-hydroxy compound (e.g., N,N-dimethylhydroxyamine, 1-hydroxy-2-(1H)-pyridone, N-hydroxysuccinimide, N-hydroxyphthalimide, 1-hydroxy-1H-benzotriazole);

and the like. These reactive derivatives are appropriately determined according to the kind of compound (II) to be used.

Preferable salt of the reactive derivative of compound (II) include salts with a base, such as alkali metal salts (e.g., sodium salt, potassium salt and the like), alkaline earth metal salts (e.g., calcium salt, magnesium salt and the like), ammonium salts, salts with an organic base (e.g., trimethylamine salt, triethylamine salt, pyridine salt, picoline salt, dicyclohexylamine salt, N,N-dibenzylethylenediamine salt and the like) and the like.

This reaction is preferably carried out without solvent or in a solvent inert to the reaction. The solvent is not particularly limited as long as the reaction proceeds, and examples thereof include alcohols such as methanol, ethanol, propanol, isopropanol, butanol, tert-butanol and the like; ethers such as dioxane, tetrahydrofuran, diethyl ether, tert-butyl methyl ether, diisopropyl ether, ethylene glycol-dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide; water and the like. These solvents may be used in a mixture of two or more kinds thereof at an appropriate ratio.

In this reaction, when compound (II) is used in the form of a free acid or a salt thereof, the reaction is preferably carried out in the presence of a conventional condensing agent such as a carbodiimide (e.g., N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide and the like); N,N'-carbonylbis(2-methylimidazole); a trialkyl phosphate; a polyphosphate (e.g., ethyl polyphosphate, isopropyl polyphosphate and the like); phosphorus oxychloride; diphenylphosphorylazide; thionyl chloride; oxalyl chloride; a to lower alkyl haloformate (e.g., ethyl chloroformate, isopropyl chloroformate and the like); triphenylphosphine; 1-[bis(dimethylamino)methylene]-1H-1,2,3-triazolo(4,5-b)pyridinium 3-oxide hexafluorophosphate (HATU); N-hydroxybenzotriazole; 1-(p-chlorobenzenesulfonyloxy)-6-chloro-1H-benzotriazole; Vilsmeier-reagent (prepared by the reaction of N,N'-dimethylformamide and thionyl chloride, phosgene, chloroformic acid trichloromethyl, phosphorus oxychloride or the like), and the like.

This reaction may be carried out in the presence of a base if desired. Examples of the base include alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate and the like; alkali metal hydrogen carbonates such as sodium hydrogen carbonate, potassium hydrogen carbonate and the like; alkali metal $C_{1-6}$ alkoxides such as sodium methoxide, sodium ethoxide, potassium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithium diisopropylamide and the like, and the like.

The amount of compound (V) to be used is generally 1 to 10 mol, preferably 1 to 3 mol, per 1 mol of compound (II). The amount of the base to be used is generally 1 to 10 mol, preferably 1 to 3 mol, per 1 mol of compound (II).

The reaction temperature is generally −30° C. to 100° C. The reaction time is generally 0.5 to 20 hr.

When an mixed anhydride is used as the reactive derivative of compound (II), the reaction may be carried out by reacting compound (II) with a chlorocarbonate (e.g., methyl chlorocarbonate, ethyl chlorocarbonate, isobutyl chlorocarbonate) in the presence of a base (e.g., triethylamine, N-methylmorpholine, N,N-dimethylaniline, sodium hydrogen carbonate, sodium carbonate, potassium carbonate), and then by reacting the resulting compound with compound (V).

This reaction is preferably carried out without solvent or in a solvent inert to the reaction. The solvent is not particularly limited as long as the reaction proceeds, and examples thereof include ethers such as dioxane, tetrahydrofuran, diethyl ether, tert-butyl methyl ether, diisopropyl ether, ethylene glycol-dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane; hexamethylphosphoramide and the like. These solvents may be used in a mixture of two or more kinds thereof at an appropriate ratio.

The amount of the chlorocarbonate to be used is generally 1 to 10 mol, preferably 1 to 3 mol, per 1 mol of compound (II).

The reaction temperature is generally −30° C. to 100° C. The reaction time is generally 0.5 to 20 hr.

Step 6

In this step, enone compound (VII) is produce by reacting compound (VI) obtained in Step 5 with an alkenyl metal reagent.

Preferable examples of the alkenyl metal reagent include organic lithiums such as vinyllithium, 1-propenyllithium and the like; Grignard reagents such as vinylmagnesium bromide, vinylmagnesium chloride, 1-propenylmagnesium bromide and the like.

This reaction is advantageously carried out in a solvent inert to the reaction. The solvent is not particularly limited as long as the reaction proceeds, and preferable examples thereof include ethers such as diethyl ether, diisopropyl ether, diphenyl ether, tetrahydrofuran, 1,4-dioxane, 1,2-dimethoxyethane and the like; hydrocarbons such as cyclohexane, hexane, benzene, toluene and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; sulfoxides such as dimethyl sulfoxide and the like, a mixed solvent thereof and the like.

While the reaction time varies depending on the kind and amount of the reagent and solvent to be used, it is generally 10 min to 100 hr, preferably 30 min to 50 hr. The reaction temperature is generally −70 to 100° C., preferably 0 to 80° C.

The amount of the alkenyl metal reagent to be used is about 1 to about 5 mol, preferably about 1 to about 3 mol, per 1 mol of compound (VI).

Step 7

In this step, diketone compound (IX) is produced by reacting enone compound (VII) obtained in Step 6 with aldehyde compound (VIII) in the presence of a thiazolium salt and a base.

Preferable examples of the thiazolium salt include 3-benzyl-5-(2-hydroxyethyl)-4-methyl-1,3-thiazol-3-ium chloride, 3-ethyl-5-(2-hydroxyethyl)-4-methyl-1,3-thiazol-3-ium bromide and the like.

Examples of the base include organic bases such as trimethylamine, triethylamine, diethylisopropylamine and the like, and inorganic bases such as calcium carbonate, cesium carbonate, sodium hydroxide and the like.

This reaction is advantageously carried out without solvent or in a solvent inert to the reaction. The solvent is not particularly limited as long as the reaction proceeds, and preferable examples thereof include alcohols such as methyl alcohol, ethyl alcohol, tert-butyl alcohol and the like; is ethers such as diethyl ether, diisopropyl ether, diphenyl ether, tetrahydrofuran, 1,4-dioxane, 1,2-dimethoxyethane and the like; hydrocarbons such as hexane, benzene, toluene and the like; amides such as N,N-dimethylformamide, N,N-dimethylacetamide, hexamethylphosphoric triamide and the like; halogenated hydrocarbons such as dichloromethane, chloroform, carbon tetrachloride, 1,2-dichloroethane and the like; sulfoxides such as dimethyl sulfoxide and the like, a mixed solvent thereof and the like.

While the reaction time varies depending on the kind and amount of the reagent and solvent to be used, it is generally 10 min to 100 hr, preferably 30 min to 50 hr. The reaction temperature is generally 0 to 200° C., preferably 50 to 100° C.

The amount of aldehyde compound (VIII) to be used is about 1 to about 5 mol, preferably about 1 to about 3 mol, per 1 mol of compound (VII).

The amount of the thiazolium salt and base to be used is about 0.01 to about 10 mol, preferably about 0.1 to about 3 mol, per 1 mol of compound (VII), respectively.

Step 8

In this step, pyrrole compound (I-c) is produced by subjecting diketone compound (IX) obtained in Step 7 to a ring-closing reaction in the presence of ammonia or an ammonium salt.

Preferable examples of the ammonium salt include ammonium salts with inorganic acid such as ammonium sulfate, ammonium carbonate and the like, ammonium salts with organic acid such as ammonium formate, ammonium acetate and the like.

This reaction is advantageously carried out without solvent or in a solvent inert to the reaction. The solvent is not particularly limited as long as the reaction proceeds, and preferable examples thereof include alcohols such as methanol, ethanol, 1-propanol, 2-propanol, tert-butyl alcohol and the like; halogenated hydrocarbons such as dichloromethane, chloroform, 1,2-dichloroethane and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoric triamide and the like; organic acids such as formic acid, acetic acid, propanoic acid, trifluoroacetic acid, methanesulfonic acid and the like, a mixed solvent thereof and the like.

While the reaction time varies depending on the kind and amount of the reagent and solvent to be used, it is generally 10 min to 100 hr, preferably 30 min to 50 hr. The reaction temperature is generally −20 to 150° C., preferably 0 to 100° C.

The amount of the ammonia or ammonium salt to be used is about 1 to about 10 mol, preferably about 1 to about 3 mol, per 1 mol of compound (IX).

Of the compound represented by the formula (I), the imidazole derivative can also be produced, for example, according to the method shown in the following Reaction Scheme 4.

Reaction Scheme 4

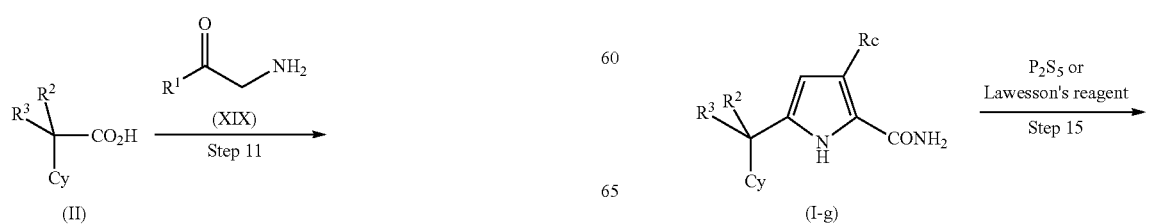

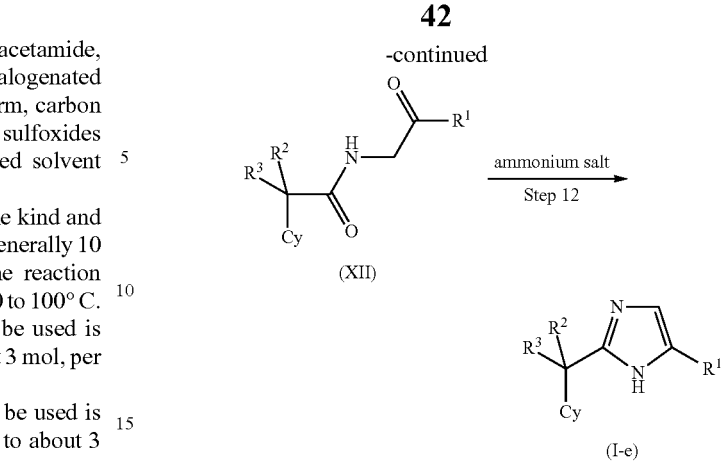

wherein each symbol is as defined above.

Step 11

Compound (XII) can be produced by reacting compound (II) or a reactive derivative of the carboxy group or a salt thereof with amine compound (XIX) or a salt thereof, according to the method of Step 1 of Reaction Scheme 2.

Compound (XIX) can be synthesized according to a known method.

Step 12

Compound (I-e) can be produced by subjecting compound (XII) to a ring-closing reaction, according to the method of Step 4 of Reaction Scheme 2.

Compound (XV), which is compound (I) wherein $R^1$ is an optionally substituted thiazolyl group, can also be produced according to the following method.

Reaction Scheme 5

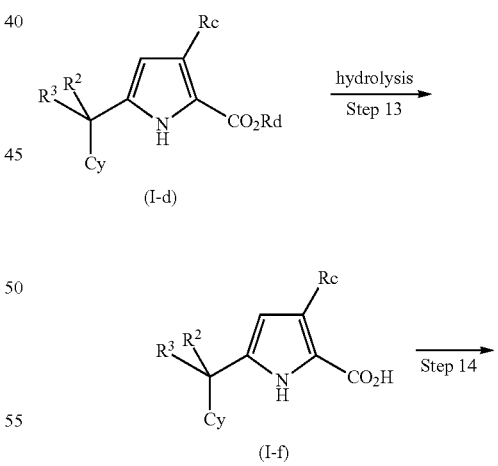

-continued (XIII)

(XV)

wherein E is a leaving group, Rc is a hydrogen atom, an optionally substituted alkyl group, an optionally substituted cyclic group, or an optionally substituted carboxy group, Rd is an optionally substituted alkyl group, Re is a hydrogen atom, an optionally substituted alkyl group, an optionally substituted cyclic group, or an optionally substituted carboxy group, and the other symbols are as defined above.

Examples of the "leaving group" for E include a halogen atom; an optionally halogenated $C_{1-6}$ alkylsulfonyloxy group (e.g., methanesulfonyloxy, ethanesulfonyloxy, trichloromethanesulfonyloxy, trifluoromethanesulfonyloxy); a $C_{6-10}$ arylsulfonyloxy group optionally having 1 to 3 substituents selected from a $C_{1-6}$ alkyl group, a $C_{1-6}$ alkoxy group and a nitro group (e.g., phenylsulfonyloxy, m-nitrophenylsulfonyloxy, p-toluenesulfonyloxy); a $C_{1-6}$ alkoxysulfonyloxy group; a $C_{6-10}$ aryloxysulfonyloxy group and the like.

Examples of the "optionally substituted alkyl group" for Rc, Rd or Re include an optionally substituted $C_{1-6}$ alkyl group.

Examples of the "optionally substituted cyclic group" for Rc or Re include an optionally substituted $C_{3-7}$ cycloalkyl group, an optionally substituted $C_{6-14}$ aryl group, an optionally substituted heterocyclic group and the like.

Examples of the "optionally substituted carboxy group" for Rc or Re include an optionally esterified carboxy group and the like.

Step 13

Compound (I-f) can be produced by subjecting compound (I-d) to hydrolysis. The hydrolysis is carried out using an acid or a base according to a conventional method.

Examples of the acid include mineral acids such as hydrochloric acid, sulfuric acid and the like; Lewis acids such as boron trichloride, boron tribromide and the like; organic acids such as trifluoroacetic acid, p-toluenesulfonic acid and the like, and the like. The Lewis acid can be used together with a thiol or a sulfide.

Examples of the base include alkali metal hydroxides such as lithium hydroxide, sodium hydroxide, potassium hydroxide, barium hydroxide and the like; alkali metal carbonates such as sodium carbonate, potassium carbonate and the like; alkali metal $C_{1-6}$ alkoxides such as sodium methoxide, sodium ethoxide, potassium tert-butoxide and the like; organic bases such as triethylamine, imidazole, formamidine and the like, and the like.

The amount of the acid or base to be used is generally about 0.5 to 10 mol, preferably about 0.5 to 6 mol, per 1 mol of compound (I-d).

The hydrolysis is carried out without a solvent or in a solvent inert to the reaction. While the solvent is not particularly limited as long as the reaction proceeds, examples of the solvent include alcohols such as methanol, ethanol, propanol and the like; aromatic hydrocarbons such as benzene, toluene and the like; saturated hydrocarbons such as cyclohexane, hexane and the like; organic acids such as formic acid, acetic acid and the like; ethers such as tetrahydrofuran, 1,4-dioxane, 1,2-dimethoxyethane and the like; amides such as N,N-dimethylformamide, N,N-dimethylacetamide and the like; halogenated hydrocarbons such as dichloromethane, chloroform, carbon tetrachloride, 1,2-dichloroethane and the like; nitriles such as acetonitrile, propionitrile and the like; ketones such as acetone, methyl ethyl ketone and the like; sulfoxides such as dimethyl sulfoxide and the like; water and the like can. These solvents may be used in a mixture at an appropriate ratio.

The reaction time is generally 10 min to 60 hr, preferably 10 min to 12 hr. The reaction temperature is generally −10 to 200° C., preferably 0 to 120° C.

Step 14

Compound (I-g) can be produced by reacting compound (I-f) or a reactive derivative of the carboxy group or a salt thereof with ammonia or 1-hydroxybenztriazole-ammonia complex, according to the reaction of Step 1 of Reaction Scheme 2.

Step 15

Compound (XIII) can be produced by reacting compound (I-g) with diphosphorus pentasulfide or the Lawesson's reagent.

This reaction is carried out without a solvent or in a solvent inert to the reaction. While the solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; nitrogen-containing aromatic compounds such as pyridine, quinoline and the like, and the like. These solvents may be used in a mixture at an appropriate ratio.

The amount of the diphosphorus pentasulfide or Lawesson's reagent to be used is generally 0.5 to 10 mol, preferably 0.5 to 3 mol, per 1 mol of compound (I-g).

The reaction temperature is generally −30° C. to 100° C. The reaction time is generally 0.5 to 20 hr.

Step 16

Compound (XV) can be produced by reacting compound (XIII) with compound (XIV).

Compound (XIV) can be synthesized according to a known method.

This reaction is carried out in the presence of an acid catalyst or a base if desired.

Examples of the acid catalyst include mineral acids such as hydrochloric acid, sulfuric acid and the like; Lewis acids such as boron trihalides (e.g., boron trichloride, boron trifluoride), titanium tetrahalides (e.g., titanium tetrachloride, titanium tetrabromide), halogenated aluminums (e.g., aluminum chloride, aluminum bromide) and the like; organic acids such as acetic acid, formic acid, trifluoroacetic acid and the like, and the like.

Examples of the base include organic bases such as triethylamine, pyridine, 4-dimethylaminopyridine, diisopropylethylamine and the like; inorganic bases such as sodium hydroxide, potassium hydroxide, sodium carbonate, potassium carbonate and the like, and the like.

This reaction is carried out without a solvent or in a solvent inert to the reaction. While the solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; alcohols such as methanol, ethanol, propanol and the like; aromatic hydrocarbons such as benzene, toluene and the like; saturated hydrocarbons such as cyclohexane, hexane and the like; amides such as N,N-dimethylformamide, N,N-dimethylacetamide, hexamethylphosphoramide and the like, and the like. These solvents may be used in a mixture at an appropriate ratio.

The amount of compound (XIV) and the acid catalyst to be used is generally 1 to 10 mol, preferably 1 to 3 mol, per 1 mol of compound (XIII), respectively.

While the reaction time varies depending on the kind and amount of compound (XIII), compound (XIV) and the acid catalyst to be used, it is generally about 1 hr to about 100 hr, preferably about 1 hr to about 50 hr. The reaction temperature is generally about −20 to about 120° C., preferably about 0 to about 80° C.

The amount of compound (XIV) and the base to be used is generally 1 to 10 mol, preferably 1 to 3 mol, per 1 mol of compound (XIII), respectively.

While the reaction time varies depending on the kind and amount of compound (XIII), compound (XIV) and the base to be used, it is generally about 1 hr to about 100 hr, preferably about 1 hr to about 50 hr. The reaction temperature is is generally about −20 to about 120° C., preferably about 0 to about 80° C.

Compound (XVII), which is compound (I) wherein $R^1$ is an optionally substituted 1,3,4-thiadiazolyl group, can also be produced according to the following method.

tuted carboxy group" for Rf include those exemplified as the "optionally substituted alkyl group", "optionally substituted cyclic group" and "optionally substituted carboxy group" for Rc.

Step 17

Compound (I-h) can be produced by reacting compound (I-f) or a reactive derivative of the carboxy group or a salt thereof with compound (XVI) or a salt thereof, according to the reaction of Step 1 of Reaction Scheme 2.

Compound (XVI) can be synthesized according to a known method.

Step 18

Compound (XVII) can be produced by reacting compound (I-h) with diphosphorus pentasulfide or the Lawesson's reagent. This reaction is carried out without a solvent or in a solvent inert to the reaction. While the solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; nitrogen-containing aromatic compounds such as pyridine, quinoline and the like, and the like. These solvents may be used in a mixture of two or more kinds thereof at an appropriate ratio.

The amount of the diphosphorus pentasulfide or Lawesson's reagent to be used is generally 0.5 to 10 mol, preferably 0.5 to 3 mol, per 1 mol of compound (I-h).

The reaction temperature is generally −30° C. to 100° C.

The reaction time is generally 0.5-20 hr.

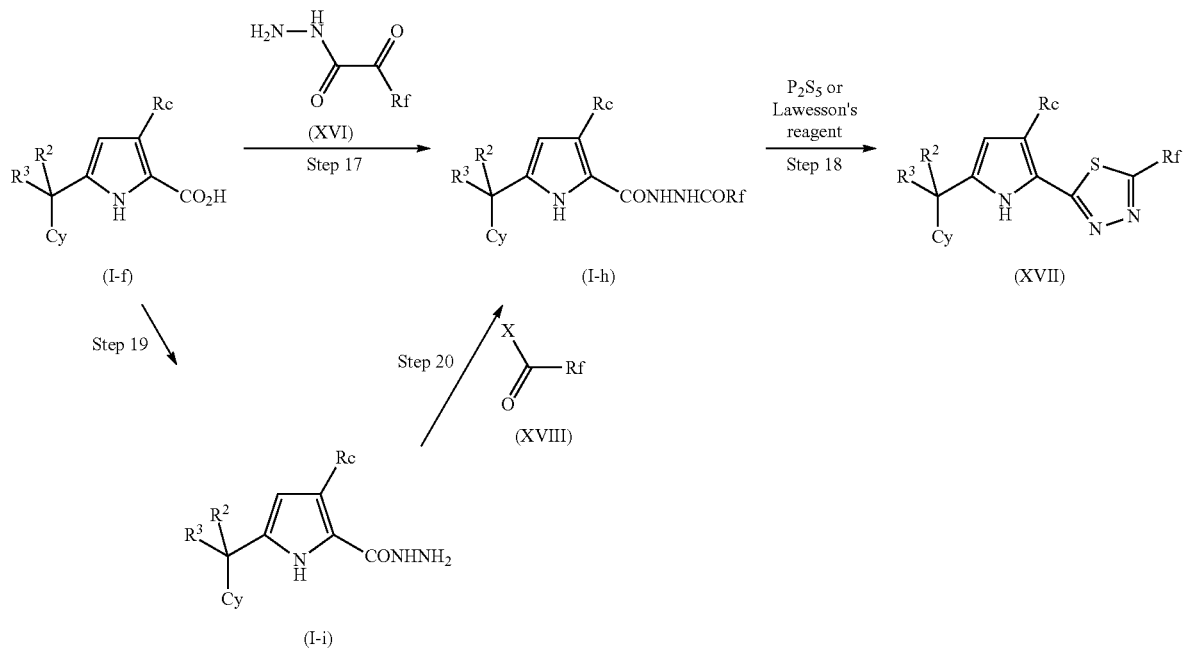

Reaction Scheme 6 wherein X is a halogen atom, Rf is a hydrogen atom, an optionally substituted alkyl group, an optionally substituted cyclic group, or an optionally substituted carboxy group, and the other symbols are as defined above.

Examples of the "optionally substituted alkyl group", "optionally substituted cyclic group" and "optionally substi- Step 19

Compound (I-i) can be produced by reacting compound (I-f) or a reactive derivative of the carboxy group or a salt thereof with hydrazine or a salt thereof, according to the reaction of Step 1 of Reaction Scheme 2.

Step 20

Compound (I-h) can also be produced by reacting compound (I-i) with compound (XVIII), according to the reaction of Step 1 of Reaction Scheme 2.

Compound (XVIII) can be synthesized according to a known method.

Compound (I) can be produced according to the method shown in the following Reaction Scheme 7.

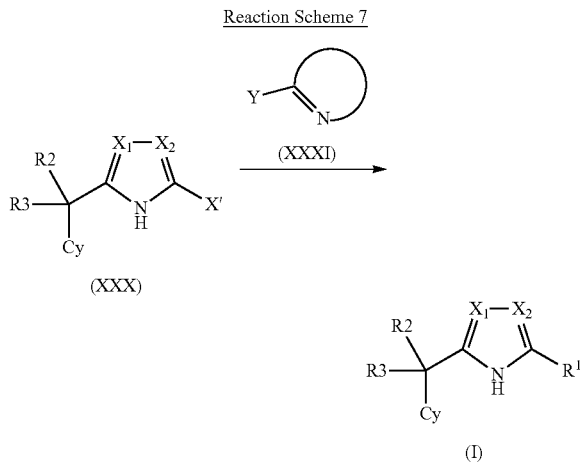

wherein X' is a leaving group; Y is a metal (e.g., potassium, sodium, lithium, magnesium, copper, mercury, zinc, thallium, boron, tin or the like (the metal is optionally alkylated, hydroxidized, alkoxylated or formed into a complex)); and the other symbols are as defined above.

Examples of the "leaving group" for X' include those exemplified as the "leaving group" for E. Preferable specific examples of X' include iodine, bromine, a trifluoromethanesulfonyloxy group, a phenylsulfonyloxy group, a m-nitrophenylsulfonyloxy group, a p-toluenesulfonyloxy group and the like.

In this scheme, compound (I) is produced by reacting compound (XXX) with compound (XXXI) in the presence of a base.

Examples of the base include alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogen carbonates such as sodium hydrogen carbonate, potassium hydrogen carbonate and the like; alkali metal phosphates such as tripotassium phosphate, trisodium phosphate and the like; alkali metal alkoxides having 1 to 6 carbon atoms such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2] octane, 1,8-diazabicyclo[5.4.0]-7-undecene and the like; organic lithiums such as methyllithium, n-butyllithium, sec-butyllithium, tert-butyllithium and the like; lithium amides such as lithium diisopropylamide and the like, and the like.

The reaction of compound (XXX) with compound (XXXI) is advantageously carried out in a solvent inert to the reaction.

While the solvent is not particularly limited as long as the reaction proceeds, and examples thereof include alcohols such as methanol, ethanol, propanol, isopropanol, butanol, tert-butanol and the like; ethers such as dioxane, tetrahydrofuran, diethyl ether, tert-butyl methyl ether, diisopropyl ether, ethylene glycol-dimethyl ether and the like; esters such as ethyl formate, ethyl acetate, n-butyl acetate and the like; halogenated hydrocarbons such as dichloromethane, chloroform, carbon tetrachloride, trichloroethylene and the like; hydrocarbons such as n-hexane, benzene, toluene and the like; amides such as formamide, N,N-dimethylformamide, N,N-dimethylacetamide and the like; nitriles such as acetonitrile, propionitrile and the like; sulfoxides such as dimethylsulfoxide and the like; sulfolane, hexamethylphosphoramide, water, a mixture of two or more kinds thereof, and the like.

This reaction can be generally promoted using a metal catalyst.

Examples of the metal catalyst include metal complexes having various ligands.

Examples of the metal complex include palladium compounds [e.g., palladium(II) acetate, tetrakis(triphenylphosphine)palladium(0), bis(triphenylphosphine)palladium(II) chloride, dichlorobis(triethylphosphine)palladium(0), tris(dibenzylideneacetone)dipalladium-2,2'-bis(diphenylphosphino)-1,1'-binaphthyl, a complex of palladium acetate (II) and 1,1'-bis(diphenylphosphino)ferrocene, and the like]; nickel compounds [e.g., tetrakis(triphenylphosphine)nickel (o), bis(triethylphosphine)nickel (II) chloride, bis(triphenylphosphine)nickel (II) chloride and the like]; rhodium compounds [e.g., tris(triphenylphosphine)rhodium (III) chloride and the like]; cobalt compounds; copper compounds [e.g., copper oxide, copper(II) chloride and the like]; platinum compounds and the like. Of these, palladium compounds, nickel compounds and copper compounds are preferable.

The amount of the metal catalyst to be used is generally about 0.000001 to 5 mol, preferably about 0.0001 to 1 mol, per 1 mol of compound (XXX).

When the metal catalyst unstable to oxygen is used, this reaction is preferably carried out under an inactive gas (e.g., argon, nitrogen) stream.

The amount of compound (XXXI) to be used is generally about 0.8 to 0 mol, preferably about 0.9 to 2 mol, per 1 mol of compound (XXX). The amount of the base to be used is about 1 to about 20 mol, preferably about 1 to about 5 mol, per 1 mol of compound (XXX).

The reaction temperature is generally about −10° C. to about 250° C., preferably about 0° C. to about 150° C.

While the reaction time varies depending on the kind of compound (XXX), compound (XXXI), the metal catalyst, base and solvent; the reaction temperature and the like, it is generally about 1 min to about 200 hr, preferably about 5 min to about 100 hr.

Compound (XXX) and compound (XXXI) can be synthesized according to a method known per se.

Compound (I) can also be produced according to the method shown in the following Reaction Scheme 8.

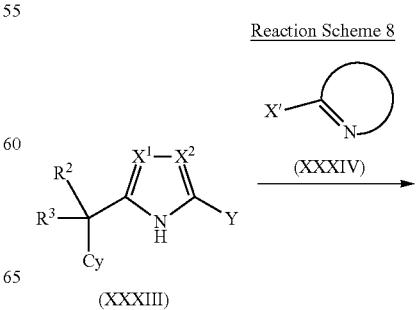

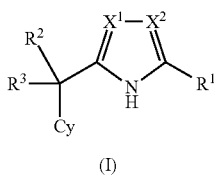

(I)

wherein each symbol is as defined above.

Compound (I) can be produced by reacting compound (XXXIII) with compound (XXXIV) in the presence of a base. This reaction can be carried out in the same manner as in the above-mentioned Reaction Scheme 7.

Compound (XXXIII) and compound (XXXIV) can be synthesized according to a method known per se.

Of compound (II), the compound wherein the nitrogen atom of Cy and the carbon atom of the side chain of the carboxylic acid are form a covalent bond, can also be produced according the method shown in the following Reaction Scheme 9.

Reaction Scheme 9

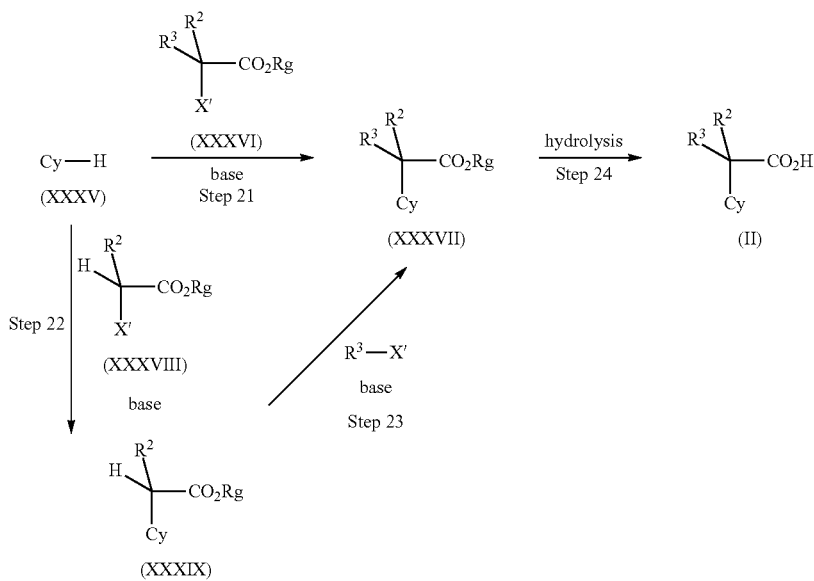

wherein Rg is a $C_{1-6}$ alkyl group, and the other symbols are as defined above.

Step 21

Compound (XXXVII) can be produced by reacting compound (XXXV) with compound (XXXVI) in the presence of a base.

Step 22

Compound (XXXIX) can be produced by reacting compound (XXXV) with compound (XXXVIII) in the presence of a base.

Examples of the base used in Step 21 and Step 22 include alkali metal hydrides such as sodium hydride, potassium hydride and the like; alkali metal hydroxides such as lithium hydroxide, sodium hydroxide, potassium hydroxide and the like; alkaline earth metal hydroxides such as magnesium hydroxide, calcium hydroxide and the like; alkali metal carbonates such as sodium carbonate, potassium carbonate, cesium carbonate and the like; alkali metal hydrogen carbonates such as sodium hydrogen carbonate, potassium hydrogen carbonate and the like; alkali metal phosphates such as tripotassium phosphate, trisodium phosphate and the like; alkali metal alkoxides having 1 to 6 carbon atoms such as sodium methoxide, sodium ethoxide, sodium tert-butoxide and the like; organic bases such as trimethylamine, triethylamine, diisopropylethylamine, pyridine, picoline, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene and the like; organic lithiums such as methyllithium, n-butyllithium, sec-butyllithium, tert-butyllithium and the like; lithium amides such as lithium diisopropylamide and the like, and the like.

The reaction of Step 21 or Step 22 is carried out without solvent or in a solvent inert to the reaction. While the solvent is not particularly limited as long as the reaction proceeds, and examples thereof include alcohols such as methanol, ethanol, propanol, isopropanol, butanol, tert-butanol and the like; ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; halogenated hydrocarbons such as dichloromethane, chloroform, carbon tetrachloride, trichloroethylene and the like; amides such as N,N-dimethylformamide, N,N-dimethylacetamide, hexamethylphosphoramide and the like; nitriles such as acetonitrile, propionitrile and the like; sulfoxides such as dimethylsulfoxide and the like, and the like. These solvents may be used in a mixture of two or more kinds thereof at an appropriate ratio.

The amount of compound (XXXVI) or compound (XXXVIII) and the base to be used is generally 1 to 10 mol, preferably 1 to 3 mol; per 1 mol of compound (XXXV), respectively.

While the reaction time varies depending on the kind or amount of compound (XXXV), compound (XXXVI), compound (XXXVIII) and the base, it is generally about 1 hr to about 100 hr, preferably about 1 hr to about 50 hr. The reaction temperature is generally about −20 to about 120° C., preferably about 0 to about 80° C.

Step 23

Compound (XXXVII) can also be produced by reacting compound (XXXIX) with compound ($R^3$—X') in the presence of a base.

Examples of the base include alkali metal hydrides such as sodium hydride, potassium hydride and the like; alkali metal alkoxides having 1 to 6 carbon atoms such as sodium methoxide, sodium ethoxide, sodium tert-butoxide and the like; organic lithiums such as methyllithium, n-butyllithium, sec-butyllithium, tert-butyllithium and the like; lithium amides such as lithium diisopropylamide and the like, and the like.

This reaction is carried out in an inert solvent. The solvent is not particularly limited as long as the reaction proceeds, and examples thereof include ethers such as diethyl ether, diisopropyl ether, diphenyl ether, tetrahydrofuran, 1,4-dioxane, 1,2-dimethoxyethane and the like; aromatic hydrocarbons such as benzene, toluene and the like; saturated hydrocarbons such as cyclohexane, hexane and the like; N,N,N',N'-tetramethylethylenediamine and the like; 1,3-dimethyl-3,4,5,6-tetrahydro-2(1H)-pyrimidinone and the like; hexamethylphosphoramide and the like. These solvents may be used in a mixture of two or more kinds thereof at an appropriate ratio.

The amount of compound ($R^3$—X') and the base to be used is generally 1 to 10 mol, preferably 1 to 3 mol, per 1 mol of compound (XXXIX), respectively.

While the reaction time varies depending on the kind or amount of compound (XXXIX), compound ($R^3$—X') and base, it is generally about 1 hr to about 100 hr, preferably about 1 hr to about 50 hr. The reaction temperature is generally about −70 to about 120° C., preferably about −70 to about 50° C.

Step 24

Compound (II) can be synthesized from compound (XXXVII) according to hydrolysis known per se.

In the above-mentioned reaction resultant product and compound (I), the functional group in a molecule can also be converted to the object functional group by combining chemical reactions known per se. Examples of such chemical reaction include oxidation reaction, reduction reaction, alkylation reaction, hydrolysis reaction, amination reaction, amidation reaction, esterification reaction, aryl-coupling reaction, deprotection reaction and the like.

In each of the above-mentioned reactions, when the starting compound has an amino group, a carboxyl group, a hydroxy group, a carbonyl group or a mercapto group as a substituent, a protecting group generally used in peptide chemistry and the like may be introduced into these groups. By removing the protecting group as necessary after the reaction, the objective compound can be obtained.

Examples of the amino-protecting group include a formyl group, a $C_{1-6}$ alkyl-carbonyl group (e.g., acetyl, propionyl), a $C_{1-6}$ alkoxy-carbonyl group (e.g., methoxycarbonyl, ethoxycarbonyl, tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-10}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the hydroxyl-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

Examples of the carbonyl-protecting group include a cyclic acetal (e.g., 1,3-dioxane), a non-cyclic acetal (e.g., di-$C_{1-6}$ alkylacetal) and the like.

Examples of the mercapto-protecting group include a $C_{1-6}$ alkyl group, a phenyl group, a trityl group, a $C_{7-10}$ aralkyl group (e.g., benzyl), a $C_{1-6}$ alkyl-carbonyl group, a benzoyl group, a $C_{7-10}$ aralkyl-carbonyl group (e.g., benzylcarbonyl), a $C_{1-6}$ alkoxy-carbonyl group; a $C_{6-14}$ aryloxy-carbonyl group (e.g., phenyloxycarbonyl), a $C_{7-14}$ aralkyloxy-carbonyl group (e.g., benzyloxycarbonyl, 9-fluorenylmethoxycarbonyl), a 2-tetrahydropyranyl'group, a $C_{1-6}$ alkylamino-carbonyl group (e.g., methylaminocarbonyl, ethylaminocarbonyl) and the like. These groups are optionally substituted by 1 to 3 substituents selected from a halogen atom, a $C_{1-6}$ alkyl group, a $C_{1-6}$ alkoxy group and a nitro group.

The compound of the present invention obtained according to the above-mentioned production method can be isolated and purified by a known means, for example, concentration, concentrated under reduced pressure, solvent extraction, crystallization, recrystallization, phase transfer, chromatography and the like. In addition, various starting compounds used in each of the above-mentioned production methods can be isolated and purified by a known means such as those mentioned above and the like. Alternatively, the starting compounds may be directly used in the form of a reaction mixture without isolation as the starting materials of the next step.

For the production of the compound of the present invention, when the starting compound can form a salt, the compound may also be used in the form of a salt. Examples of the salt include those similar to the salts of the aforementioned compound of the present invention.

When the compound of the present invention contains an optical isomer, a stereoisomer, a positional isomer or a rotational isomer, these are encompassed in the compound of the present invention, and obtained as a single product according to a synthesis method and separation method known per se. For example, an optical isomer and an optical isomer resolved from this compound are also encompassed in the compound of the present invention.

The compound of the present invention may be in the form of a crystal.

The crystal of the compound of the present invention (hereinafter sometimes to be abbreviated as the crystal of the present invention) can be produced by crystallization of the compound of the present invention according to a crystallization method known per se.

In the present specification, the melting point refers to that measured using, for example, micromelting point measuring apparatus (Yanako, MP-500D or Buchi, B-545) or DSC (differential scanning calorimetry) device (SEIKO, EXSTAR6000) and the like.

In general, melting points vary depending on measurement apparatuses, measurement conditions and the like. The crystal in the present specification may show a different melting point described in the present specification, as long as it is within general error range.

The crystal of the present invention is superior in physicochemical properties (e.g., melting point, solubility, stability and the like) and biological properties (e.g., pharmacokinetics (absorption, distribution, metabolism, excretion), efficacy expression and the like), and is extremely useful as a pharmaceutical agent.

EXAMPLE

The present invention is explained in detail in the following by referring to the following Reference Examples, Examples, Experimental Examples and Formulation Examples, which are not to be construed as limitative. In addition, the present invention may be modified without departing from the scope of invention.

The term "room temperature" in the following Reference Examples and Examples indicates the range of generally from about 10° C. to about 35° C. As for "%", the yield is in mol/mol %, the solvent used for chromatography is in % by volume and other "%" is in % by weight. OH proton, NH proton etc. on proton NMR spectrum that could not be confirmed due to broad peak are not included in the data.

The other symbols used herein mean the following:
s: singlet
d: doublet
t: triplet
q: quartet
m: multiplet
br: broad
J: coupling constant
Hz: Hertz
CDCl$_3$: deuterated chloroform
DMSO-d$_6$: dimethyl sulfoxide-d$_6$
$^1$H-NMR: proton nuclear magnetic resonance
TFA: trifluoroacetic acid
MgSO$_4$: magnesium sulfate In the following Reference Examples and Examples, mass spectrum (MS) and nuclear magnetic resonance spectrum (NMR) were measured under the following conditions.

MS measurement tool: Agilent Technologies 1200 series, Waters ZMD, Waters ZQ2000 or Micromass Platform II.

Ionization method: Electron Spray Ionization (ESI), Atmospheric Pressure Chemical Ionization (APCI). Unless otherwise specified, ESI was employed.

NMR measurement tool: Varian Inc. Varian Gemini 200 (200 MHz), Varian Gemini 300 (300 MHz), Bruker BioSpin Corp. AVANCE 300.

In the following Reference Examples and Examples, the purification by preparative HPLC is performed according to the following conditions.

Preparative HPLC tool: Gilson, Inc. high throughput purification system
Column: ANC Combiprep ODS-A S-5 µm, 20×50 mm
Solvent: SOLUTION A; 0.1% trifluoroacetic acid-containing water,
SOLUTION B; 0.1% trifluoroacetic acid-containing acetonitrile
Gradient Cycle: 0.00 min (SOLUTION A/SOLUTION B=90/10), 1.20 min (SOLUTION A/SOLUTION B=90/10), 4.75 min (SOLUTION A/SOLUTION B=0/100), 7.30 min (SOLUTION A/SOLUTION B=0/100), 7.40 min (SOLUTION A/SOLUTION B=90/10), 7.50 min (SOLUTION A/SOLUTION B=90/10).

Flow Rate: 25 ml/min, Detection Method: UV 220 nm

Reference Example 1A

Construction of Glucokinase (GK) Expression Vector

A plasmid DNA used for expression of a protein (GST-hLGK1) having GST (Glutathione S-transferase) added to the amino terminal of human liver type GK in *Escherichia coli* was prepared as follows.

First, PCR was performed using human liver cDNA (clonetech Marathon Ready cDNA) as a template and two kinds of synthetic DNAs (5'-CAGCTCTCCATCCAAG-CAGCCGTTGCT-3'(SEQ ID NO: 1) and 5'-GGCGGC-CTGGGTCCTGACAAG-3'(SEQ ID NO: 2)), and the obtained DNA fragment was cloned using TOPO TA Cloning Kit (Invitrogen). PCR was performed using the obtained plasmid DNA as a template and synthetic DNA (5'-GGATCCAT-GCCCAGACCAAGATCCCAACTCCCA-CAACCCAACTCCCAGGTAGAGCAGATCCT GGCAGAG-3'(SEQ ID NO: 3)) having a BamHI site added to immediately before the initiation codon and synthetic DNA (5'-GAATTCCTGGCCCAGCATACAGGC-3' (SEQ ID NO: 4)) having an EcoRI site added to immediately after the stop codon. The obtained DNA fragment was subcloned into pGEX6P-2 (Amersham Biosciences) digested with BamHI and EcoRI to give a plasmid (pGEX6P-2/hLGK1) for human liver GK expression.

Reference Example 2A

Expression and Purification of GST-hLGK1

BL21 strain (Stratagene) transformed with pGEX6P-2/hLGK1 obtained in Reference Example 1A was cultured with shaking in a 200 ml Erlenmeyer flask containing LB medium (50 ml) containing 100 µg/ml ampicillin at 37° C. for 14 hr. The cultured broth (25 ml) was diluted with LB medium (225 ml) containing 100 µg/ml ampicillin, and cultured with shaking in a 1 L Erlenmeyer flask at 37° C. for 1 hr. The Erlenmeyer flask after culture was cooled on ice, 100 mM Isopropyl-Thio-β-D-Galactopyranoside (IPTG) (125 µL) was added (final concentration 50 µM), and the cells were cultured at 17° C. for 20 hr. The cultures broth was centrifuged, and the obtained cells were disrupted by ultrasonication, and the object protein (GST-hLGK1) was purified from the supernatant using Glutathione Sepharose 4B (Amersham Biosciences).

Reference Example 1

1-methyl-5-(methylsulfanyl)-1H-pyrazole-carbaldehyde

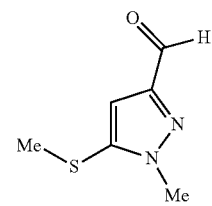

To a mixture of 5-(methylsulfanyl)-1H-pyrazole-3-carbaldehyde (10.0 g), potassium carbonate (9.70 g) and N,N'-dimethylformamide (60 mL) was slowly added methyl iodide (6.6 mL) at 0° C., and the mixture was stirred overnight at room temperature. To the reaction mixture was added water, and the mixture was extracted with ethyl acetate. The ethyl acetate layer was washed with saturated brine, dried (MgSO$_4$), and concentrated. The obtained residue was subjected to silica gel column chromatography to give the title compound (6.38 g, yield 58%) as yellow crystals from the fraction eluted with ethyl acetate-hexane (1:5, volume ratio). melting point 47-48° C. MS: 157 (MH$^+$).

Reference Example 2 methyl [1-methyl-5-(methylsulfanyl)-1H-pyrazol-3-yl]acetate

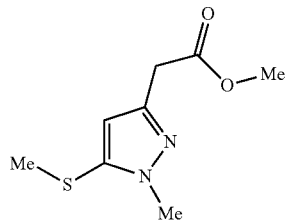 [SMILES: COC(=O)Cc1cc(SC)n(C)n1]

A mixture of 1-methyl-5-(methylsulfanyl)-1H-pyrazole-3-carbaldehyde (6.38 g), (methylsulfanyl)(methylsulfinyl)methane (10.1 g), benzyltrimethylammonium hydroxide (1.7 mL) and tetrahydrofuran (60 mL) was stirred at 60° C. for 2 hr. The reaction mixture was concentrated, and the residue was subjected to silica gel column chromatography to give a yellow oil (14.95 g) from the fraction eluted with ethyl acetate. To the obtained oil (14.95 g) was added 10% hydrogen chloride-methanol solution (200 mL), and the mixture was stirred overnight with heating under reflux. The reaction mixture was neutralized with saturated aqueous sodium hydrogen carbonate, and the mixture was extracted with ethyl acetate. The ethyl acetate layer was washed with saturated brine, dried (MgSO$_4$), and concentrated. The obtained residue was subjected to silica gel column chromatography to give the title compound (4.68 g, yield 57%) as a yellow oil from the fraction eluted with ethyl acetate-hexane (2:1, volume ratio). MS: 201 (MH$^+$).

Reference Example 3 methyl 2-[1-methyl-5-(methylsulfanyl)-1H-pyrazol-3-yl]-3-(tetrahydro-2H-pyran-4-yl)propanoate

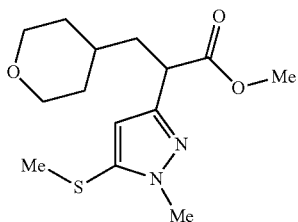 [SMILES: COC(=O)C(CC1CCOCC1)c1cc(SC)n(C)n1]

To a solution of diisopropylamine (4.0 mL) in tetrahydrofuran (60 mL) was slowly added 1.6M hexane solution (16.1 ml) of n-butyllithium at −70° C. under a nitrogen atmosphere. The reaction mixture was stirred at −70° C. for 15 min, and a solution of methyl [1-methyl-5-(methylsulfanyl)-1H-pyrazol-3-yl]acetate (4.68 g) in tetrahydrofuran (5 mL) was slowly added thereto. The reaction mixture was stirred at −70° C. for 15 min, and 4-(iodomethyl)tetrahydro-2H-pyran (5.80 g) was added thereto. The mixture was stirred overnight at room temperature. To the reaction mixture was added 10% aqueous citric acid solution, and the mixture was extracted with ethyl acetate. The ethyl acetate layer was washed with saturated brine, dried (MgSO$_4$), and concentrated. The obtained residue was subjected to silica gel column chromatography to give the title compound (2.57 g, yield 37%) as a pale-yellow oil from the fraction eluted with ethyl acetate-hexane (1:1, volume ratio). MS: 299 (MH$^+$).

Reference Example 4

2-[1-methyl-5-(methylsulfanyl)-1H-pyrazol-3-yl]-3-(tetrahydro-2H-pyran-4-yl)propanoic acid

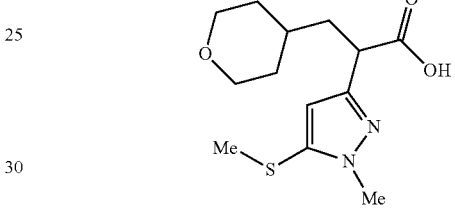

A mixture of methyl 2-[1-methyl-5-(methylsulfanyl)-1H-pyrazol-3-yl]-3-(tetrahydro-2H-pyran-4-yl)propanoate (2.52 g), 2N aqueous sodium hydroxide solution (6.3 ml), tetrahydrofuran (6 mL) and methanol (6 mL) was stirred at 50° C. for 3 hr. To the reaction mixture was added 1N hydrochloric acid (13 mL), and the mixture was extracted with ethyl acetate. The ethyl acetate layer was washed with saturated brine, dried (MgSO$_4$), and concentrated. The obtained residue was subjected to silica gel column chromatography to give the title compound (2.47 g, quantitatively) as a colorless oil from the fraction eluted with ethyl acetate. MS: 285 (MH$^+$).

Reference Example 5

N-methoxy-N-methyl-2-[1-methyl-5-(methylsulfanyl)-1H-pyrazol-3-yl]-3-(tetrahydro-2H-pyran-4-yl)propanamide

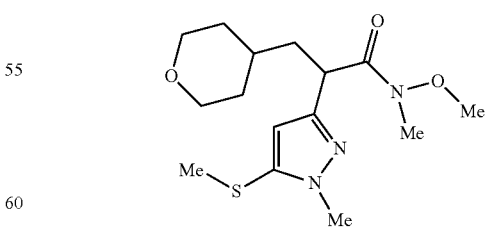

To a mixture of 2-[1-methyl-5-(methylsulfanyl)-1H-pyrazol-3-yl]-3-(tetrahydro-2H-pyran-4-yl)propanoic acid (1.09 g), N-methoxymethanamine hydrochloride (0.75 g), 1H-1,2,3-benzotriazol-1-ol (0.70 g), triethylamine (1.1 mL) and N,N-dimethylformamide (10 mL) was added N-[3-(dimethylamino)propyl]-N'-ethylcarbodiimide hydrochloride (0.88 g) at 0° C., and the mixture was stirred overnight at room temperature. To the reaction mixture was added 10% aqueous citric acid solution, and the mixture was extracted with ethyl acetate. The ethyl acetate layer was washed successively with saturated brine, saturated aqueous sodium hydrogen carbonate and saturated brine, dried ($MgSO_1$), and concentrated. The obtained residue was subjected to silica gel column chromatography to give the title compound (0.80 g, yield 63%) as a colorless oil from the fraction eluted with ethyl acetate-hexane (4:1, volume ratio). MS: 328 ($MH^+$).

Reference Example 6

4-[1-methyl-5-(methylsulfanyl)-1H-pyrazol-3-yl]-5-(tetrahydro-2H-pyran-4-yl)pent-1-en-3-one

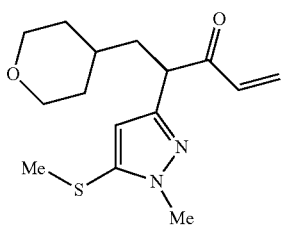 [SMILES: C=CC(=O)C(CC1CCOCC1)c1cc(SC)n(C)n1]

To a solution of N-methoxy-N-methyl-2-[1-methyl-5-(methylsulfanyl)-1H-pyrazol-3-yl]-3-(tetrahydro-2H-pyran-4-yl)propanamide (0.80 g) in tetrahydrofuran (30 mL) was slowly added vinylmagnesium bromide (1.0M tetrahydrofuran solution: 7.3 ml) at room temperature under a nitrogen atmosphere, and the mixture was stirred for 30 min. The reaction mixture was poured into an ice-cooled 1N hydrochloric acid, and the mixture was extracted with ethyl acetate. The ethyl acetate layer was washed with saturated brine, dried ($MgSO_4$), and concentrated. The obtained residue was subjected to silica gel column chromatography to give the title compound (0.60 g, yield 83%) as a colorless oil from the fraction eluted with ethyl acetate-hexane (4:1, volume ratio). MS: 295 ($MH^+$).

Reference Example 7

5-[1-methyl-5-(methylsulfanyl)-1H-pyrazol-3-yl]-6-(tetrahydro-2H-pyran-4-yl)-1-{5-[(tetrahydro-2H-pyran-2-yloxy)methyl]-1,3-thiazol-2-yl}hexane-1,4-dione

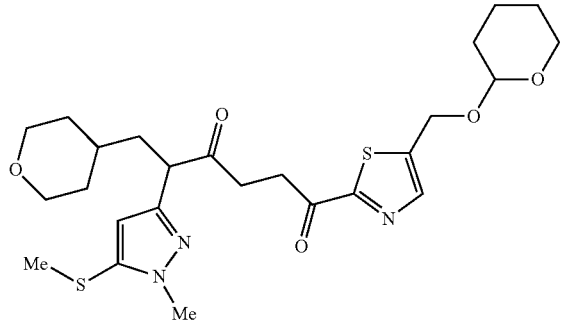 [SMILES: CSc1cc(C(CC2CCOCC2)C(=O)CCC(=O)c2ncc(COC3CCCCO3)s2)nn1C]

A mixture of 4-[1-methyl-5-(methylsulfanyl)-1H-pyrazol-3-yl]-5-(tetrahydro-2H-pyran-4-yl)pent-1-en-3-one (0.60 g), 5-[(tetrahydro-2H-pyran-2-yloxy)methyl]-1,3-thiazole-2-carbaldehyde (0.48 g), 3-benzyl-5-(2-hydroxyethyl)-4-methyl-1,3-thiazol-3-ium chloride (54 mg), triethylamine (0.11 mL), tetrahydrofuran (6 mL) and ethanol (6 ml) was stirred with heating under reflux for 2 hr. The reaction mixture was concentrated, and the residue was subjected to basic silica gel column chromatography to give the title compound (0.65 g, yield 60%) as a yellow oil from the fraction eluted with ethyl acetate-hexane (1:1, volume ratio). MS: 522 ($MH^+$).

Reference Example 8

3-(tetrahydro-2H-pyran-4-yl)alanine ethyl ester

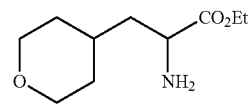 [SMILES: CCOC(=O)C(N)CC1CCOCC1]

To a solution of potassium tert-butoxide (25.7 g) in tetrahydrofuran (800 mL) was added N-(diphenylmethylidene)glycine ethyl ester (45.20 g) over 20 min at 0 to 8° C. The reaction mixture was stirred at 0° C. for 30 min, and 4-(iodomethyl) tetrahydro-2H-pyran (42.0 g) was added thereto. The reaction mixture was stirred overnight at room temperature, and the precipitate solid was filtrated. The filtrate was concentrated, the obtained residue was dissolved in ethanol (200 mL), and 2M hydrochloric acid (200 mL) was added thereto. The reaction mixture was stirred overnight at room temperature, and concentrated. The residue was diluted with water, and the mixture was washed with ethyl acetate (×4). The aqueous layer was adjusted to pH 11 with 8M aqueous sodium hydroxide solution, and the mixture was extracted with ethyl acetate. The ethyl acetate layer was washed with saturated brine, dried ($MgSO_4$), and concentrated to give the title compound (23.00 g, yield 67%) as a yellow oil.

$^1$H NMR (300 MHz, $CDCl_3$) δ1.22-1.80 (10 H, m), 3.32-3.44 (2 H, m), 3.47 (1 H, dd, J=5.3, 8.9 Hz), 3.90-4.00 (2 H, m), 4.17 (2 H, q, J=7.1 Hz).

Reference Example 9

1:1 mixture of ethyl 2-bromo-3-(tetrahydro-2H-pyran-4-yl)propanoate and ethyl 3-(tetrahydro-2H-pyran-4-yl)-2-propenoate

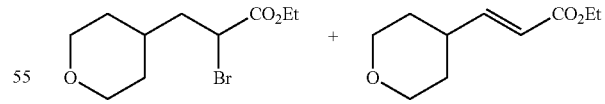

To a mixture of 3-(tetrahydro-2H-pyran-4-yl)alanine ethyl ester (23.00 g), potassium bromide (50.2 g) and 1M aqueous hydrogen bromide solution (200 mL) was added a solution of sodium nitrite (10.2 g) in water (10 mL) over 20 min at −5 to 5° C. The reaction mixture was stirred overnight at room temperature, and the mixture was extracted with ethyl acetate. The ethyl acetate layer was washed successively with saturated aqueous sodium hydrogen carbonate and saturated brine, dried ($MgSO_4$), and concentrated. The residue was subjected to silica gel column chromatography to give the title mixture (9.87 g) as a yellow oil from the fraction eluted with ethyl acetate-hexane (1:4, volume ratio).

$^1$H NMR (300 MHz, CDCl$_3$) δ1.24-1.78 (9 H, 9 H*, m), 1.94-2.10 (1 H, m), 2.30 to 2.64 (1 H*, m), 3.32-3.49 (2 H, 2 H*, m), 3.90-4.03 (2 H, 2 H*, m), 4.14-4.32 (3 H, 2 H*, m), 5.79 (1 H*, dd, J=1.2, 15.9 Hz), 6.89 (1 H*, dd, J=8.8, 15.9 Hz). * means the proton peak of the latter compound.

Reference Example 10 ethyl 2-(4-bromo-1H-indazol-1-yl)-3-(tetrahydro-2H-pyran-4-yl)propanoate

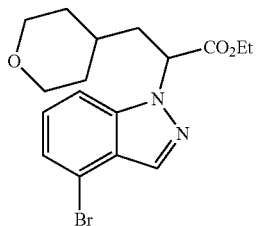 [SMILES: CCOC(=O)C(CC1CCOCC1)n1ncc2c(Br)cccc21]

A mixture of 4-bromo-1H-indazole (3.00 g), a 1:1 mixture (6.73 g) of ethyl 2-bromo-3-(tetrahydro-2H-pyran-4-yl)propanoate and ethyl 3-(tetrahydro-2H-pyran-4-yl)-2-propenoate, potassium carbonate (2.1 g) and N,N-dimethylformamide (20 mL) was stirred overnight at room temperature. To the reaction mixture was added water, and the mixture was extracted with ethyl acetate. The ethyl acetate layer was washed with saturated brine, dried (MgSO$_4$), and concentrated. The residue was subjected to silica gel column chromatography to give the title compound (3.10 g) as a yellow oil from the fraction eluted with ethyl acetate-hexane (1:4, volume ratio). MS: 383 (MH$^+$).

Reference Example 11

2-[4-(cyclopropylsulfonyl)-1H-indazol-1-yl]-N-methoxy-N-methyl-3-(tetrahydro-2H-pyran-4-yl)propanamide

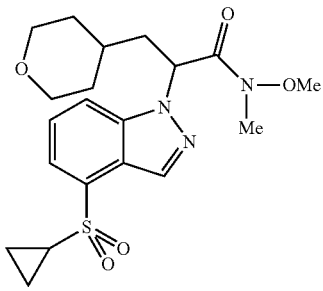 [SMILES: CON(C)C(=O)C(CC1CCOCC1)n1ncc2c(S(=O)(=O)C3CC3)cccc21]

A mixture of ethyl 2-(4-bromo-1H-indazol-1-yl)-3-(tetrahydro-2H-pyran-4-yl)propanoate (3.10 g), copper(I) iodide (0.46 g), N,N'-dimethylethylenediamine (0.26 mL), potassium carbonate (3.37 g), sodium cyclopropanesulfinate (3.1 g) and dimethyl sulfoxide (30 mL) was stirred overnight at 100° C. To the reaction mixture was added 10% aqueous citric acid solution, and the mixture was extracted with ethyl acetate. The ethyl acetate layer was washed with saturated brine, dried (MgSO$_4$), and concentrated. To a mixture of the obtained residue, tetrahydrofuran (10 mL) and methanol (10 ml) was added 2M aqueous sodium hydroxide solution (8.0 mL), and the mixture was stirred at 50° C. for 4 hr. To the reaction mixture was added 10% aqueous citric acid solution, and the mixture was extracted with ethyl acetate. The ethyl acetate layer was washed with saturated brine, dried (MgSO$_4$), and concentrated. To a mixture of the obtained residue, N,O-dimethylhydroxylamine hydrochloride (1.60 g), triethylamine (2.3 mL), 1H-1,2,3-benzotriazol-1-ol (1.84 g) and N,N-dimethylformamide (25 mL) was added N-[3-(dimethylamino)propyl]-N'-ethylcarbodiimide hydrochloride (0.88 g), and the mixture was stirred overnight at room temperature. To the reaction mixture was added 10% aqueous citric acid solution, and the mixture was extracted with ethyl acetate. The ethyl acetate layer was washed successively with saturated brine, saturated aqueous sodium hydrogen carbonate and saturated brine, dried (MgSO$_4$), and concentrated. The obtained residue was subjected to silica gel column chromatography to give the title compound (2.30 g, yield 67%) as a yellow oil from the fraction eluted with ethyl acetate. MS: 422 (MH$^+$).

Reference Example 12

4-[4-(cyclopropylsulfonyl)-1H-indazol-1-yl]-5-(tetrahydro-2H-pyran-4-yl)pent-1-en-3-one

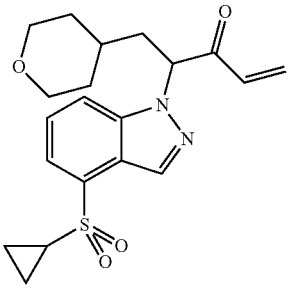 [SMILES: C=CC(=O)C(CC1CCOCC1)n1ncc2c(S(=O)(=O)C3CC3)cccc21]

To a solution of 2-[4-(cyclopropylsulfonyl)-1H-indazol-1-yl]-N-methoxy-N-methyl-3-(tetrahydro-2H-pyran-4-yl)propanamide (2.30 g) in tetrahydrofuran (20 ml) was slowly added vinylmagnesium bromide (1.0M tetrahydrofuran solution: 16.4 mL) at 0° C., and the mixture was stirred at 0° C. for 20 min. The reaction mixture was poured into an ice-cooled 1M hydrochloric acid, and the mixture was extracted with ethyl acetate. The ethyl acetate layer was washed with saturated brine, dried (MgSO$_4$), and concentrated. The residue was subjected to silica gel column chromatography to give the title compound (1.80 g, yield 84%) as a colorless oil from the fraction eluted with ethyl acetate-hexane (3:1, volume ratio). MS: 389 (MH$^+$).

Reference Example 13

5-[4-(cyclopropylsulfonyl)-1H-indazol-1-yl]-1-[5-(1,2-dihydroxy-2-methylpropyl)pyridin-2-yl]-6-(tetrahydro-2H-pyran-4-yl)hexane-1,4-dione

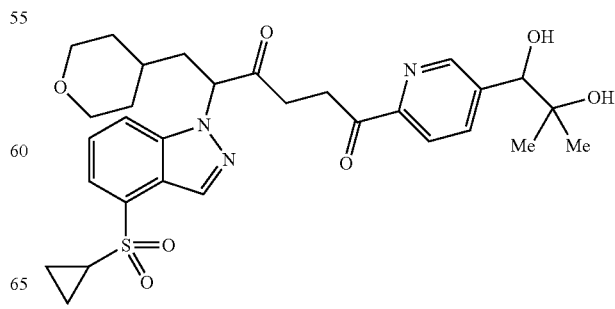

A mixture of 4-[4-(cyclopropylsulfonyl)-1H-indazol-1-yl]-5-(tetrahydro-2H-pyran-4-yl)pent-1-en-3-one (1.80 g), 5-(1,2-dihydroxy-2-methylpropyl)pyridine-2-carbaldehyde (0.99 g), 3-benzyl-5-(2-hydroxyethyl)-4-methyl-1,3-thiazol-3-ium chloride (0.12 g), triethylamine (0.26 ml), tetrahydrofuran (10 mL) and ethanol (10 mL) was stirred with heating under reflux for 2 hr. The reaction mixture was concentrated, and the residue was subjected to basic silica gel column chromatography to give the title compound (1.90 g, yield 71%) as a yellow amorphous solid from the fraction eluted with ethyl acetate. MS: 584 (MH$^+$).

Reference Example 14

4-bromo-5-methoxy-1H-indazole

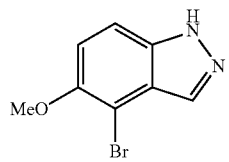 [SMILES: COc1ccc2[nH]ncc2c1Br]

To a solution of 3-bromo-4-methoxy-2-methylaniline (19.06 g) in acetonitrile (250 mL) was slowly added acetic anhydride (18.9 mL), and the mixture was stirred at room temperature for 1 hr. To the reaction mixture were added potassium acetate (2.60 g) and pentyl nitrite (22.3 g), and the mixture was heated under reflux for 8 hr. The reaction mixture was concentrated, and to the residue was added 6M hydrochloric acid (200 mL), and the mixture was heated under reflux overnight. The reaction mixture was neutralized with 8M sodium hydroxide, and the mixture was extracted with ethyl acetate. The ethyl acetate layer was washed with saturated brine, dried (MgSO$_4$), and concentrated. The residue was dissolved in tetrahydrofuran, and the solution was treated with activated carbon. The activated carbon was filtered off, the filtrate was concentrated, and the obtained residue was crystallized from diisopropyl ether. The crystals were collected by filtration, washed with diisopropyl ether, and dried to give the title compound (10.42 g, yield 52%) as yellow crystals. melting point 178-180° C. MS: 229 (MH$^+$).

Reference Example 15 ethyl (4-bromo-5-methoxy-1H-indazol-1-yl)acetate

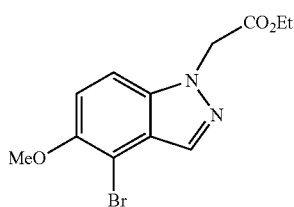 [SMILES: CCOC(=O)Cn1ncc2c(Br)c(OC)ccc21]

A mixture of 4-bromo-5-methoxy-1H-indazole (8.57 g), ethyl bromoacetate (7.56 g), potassium carbonate (6.26 g) and N,N-dimethylformamide (30 mL) was stirred overnight at room temperature. To the reaction mixture was added water, and the mixture was extracted with ethyl acetate. The ethyl acetate layer was washed with saturated brine, dried (MgSO$_4$), and concentrated. The residue was subjected to silica gel column chromatography to give the title compound (4.65 g, yield 39%) as colorless crystals from the fraction eluted with ethyl acetate-hexane (1:3, volume ratio). melting point 106-107° C. MS: 315 (MH$^+$).

Reference Example 16 ethyl 2-(4-bromo-5-methoxy-1H-indazol-1-yl)-3-(tetrahydro-2H-pyran-4H-yl)propanoate

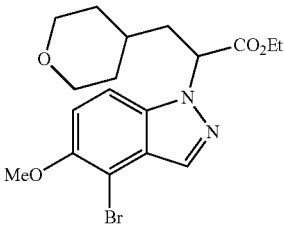 [SMILES: CCOC(=O)C(CC1CCOCC1)n1ncc2c(Br)c(OC)ccc21]

To a solution of diisopropylamine (1.35 g) in a mixed to solvent of tetrahydrofuran (30 mL) and 1,3-dimethyl-3,4,5,6-tetrahydropyrimidin-2(1H)-one (15 mL) was slowly added 1.6M hexane solution (16.1 mL) of n-butyllithium at –70° C. under a nitrogen atmosphere. The reaction mixture was stirred at –70° C. for 15 min, and a solution of ethyl (4-bromo-5-methoxy-1H-indazol-1-yl)acetate (3.65 g) in tetrahydrofuran (5 mL) was slowly added thereto. The reaction mixture was stirred at –70° C. for 20 min, 4-(iodomethyl)tetrahydro-2H-pyran (2.80 g) was added thereto, and the mixture was stirred overnight at room temperature. To the reaction mixture was added 10% aqueous citric acid solution, and the mixture was extracted with ethyl acetate. The ethyl acetate layer was washed with saturated brine, dried (MgSO$_4$), and concentrated. The obtained residue was subjected to silica gel column chromatography to give the title compound (1.36 g, yield 28%) as pale-yellow crystals from the fraction eluted with ethyl acetate-hexane (2:3, volume ratio). melting point 76-77° C. MS: 413 (MH$^+$).

Reference Example 17 ethyl 2-[4-(cyclopropylsulfonyl)-5-methoxy-1H-indazol-1-yl]-3-(tetrahydro-2H-pyran-4-yl)propanoate

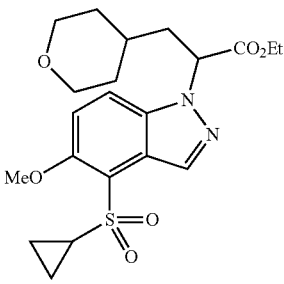 [SMILES: CCOC(=O)C(CC1CCOCC1)n1ncc2c(S(=O)(=O)C3CC3)c(OC)ccc21]

A mixture of ethyl 2-(4-bromo-5-methoxy-1H-indazol-1-yl)-3-(tetrahydro-2H-pyran-4H-yl)propanoate (1.36 g), copper (I) iodide (0.32 g), N,N'-dimethylethylenediamine (0.36 mL), sodium cyclopropanesulfinate (0.64 g) and dimethyl sulfoxide (6 mL) was stirred at 140° C. for 2 hr. To the reaction mixture was added 10% aqueous citric acid solution, and the mixture was extracted with ethyl acetate. The ethyl acetate layer was washed with saturated brine, dried (MgSO$_4$), and concentrated. The obtained residue was subjected to silica gel column chromatography to give the title compound (0.50 g, yield 33%) as a yellow oil from the fraction eluted with ethyl acetate-hexane (9:1, volume ratio). MS: 437 (MH$^+$).

Reference Example 18

2-[4-(cyclopropylsulfonyl)-5-methoxy-1H-indazol-1-yl]-N-methoxy-N-methyl-3-(tetrahydro-2H-pyran-4-yl)propanamide

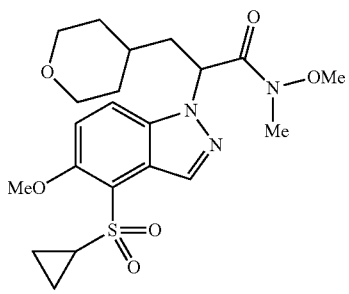 [SMILES: COc1ccc2c(cnn2C(CC2CCOCC2)C(=O)N(C)OC)c1S(=O)(=O)C1CC1]

To a solution of ethyl 2-[4-(cyclopropylsulfonyl)-5-methoxy-1H-indazol-1-yl]-3-(tetrahydro-2H-pyran-4-yl)propanoate (0.50 g) in a mixed solvent of tetrahydrofuran (4 mL) and methanol (2 ml) was added 2M aqueous sodium hydroxide solution (1.0 mL), and the mixture was stirred overnight at room temperature. To the reaction mixture was added 10% aqueous citric acid solution, and the mixture was extracted with ethyl acetate. The ethyl acetate layer was washed with saturated brine, dried ($MgSO_4$), and concentrated.

To a mixture of the obtained residue, N,O-dimethylhydroxylamine hydrochloride (0.21 g), triethylamine (0.31 mL), 1H-1,2,3-benzotriazol-1-ol (0.26 g) and N,N-dimethylformamide (10 mL) was added N-[3-(dimethylamino)propyl]-N'-ethylcarbodiimide hydrochloride (0.32 g), and the mixture was stirred at room temperature for 6 hr. To the reaction mixture was added 10% aqueous citric acid solution, and the mixture was extracted with ethyl acetate. The ethyl acetate layer was washed successively with saturated brine, saturated aqueous sodium hydrogen carbonate and saturated brine, dried ($MgSO_4$), and concentrated. The obtained residue was subjected to silica gel column chromatography to give the title compound (0.51 g, quantitatively) as a colorless oil from the fraction eluted with ethyl acetate. MS: 452 ($MH^+$).

Reference Example 19

5-[4-(cyclopropylsulfonyl)-5-methoxy-1H-indazol-1-yl]-1-[5-(1,2-dihydroxy-2-methylpropyl)pyridin-2-yl]-6-(tetrahydro-2H-pyran-4-yl)hexane-1,4-dione

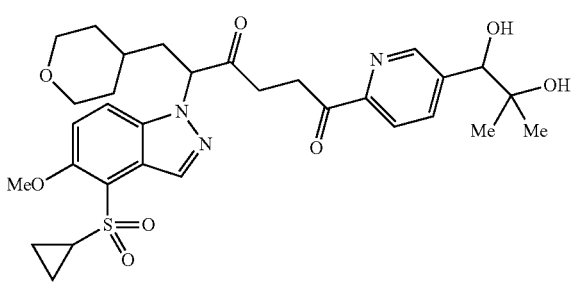 [SMILES: COc1ccc2c(cnn2C(CC2CCOCC2)C(=O)CCC(=O)c2ccc(C(O)C(C)(C)O)cn2)c1S(=O)(=O)C1CC1]

To a solution of 2-[4-(cyclopropylsulfonyl)-5-methoxy-1H-indazol-1-yl]-N-methoxy-N-methyl-3-(tetrahydro-2H-pyran-4-yl)propanamide (0.50 g) in tetrahydrofuran (5 mL) was slowly added vinylmagnesium bromide (1.0M tetrahydrofuran solution: 3.3 mL) at 0° C., and the mixture was stirred at 0° C. for 20 min. The reaction mixture was poured into an ice-cooled 1M hydrochloric acid, and the mixture was extracted with ethyl acetate. The ethyl acetate layer was washed with saturated brine, dried ($MgSO_4$), and concentrated. A mixture of the obtained residue, 5-(1,2-dihydroxy-2-methylpropyl)pyridine-2-carbaldehyde (0.24 g), 3-benzyl-5-(2-hydroxyethyl)-4-methyl-1,3-thiazol-3-ium chloride (30 mg), triethylamine (0.06 mL), tetrahydrofuran (6 mL) and ethanol (4 mL) was stirred with heating under reflux for 4 hr. The reaction mixture was concentrated, and the residue was subjected to basic silica gel column chromatography to give the title compound (0.21 g, yield 31%) as a yellow oil from the fraction eluted with tetrahydrofuran-hexane (3:1, volume ratio). MS: 614 ($MH^+$).

Reference Example 20

4-(cyclopropylsulfonyl)-1H-pyrazolo[3,4-b]pyridine

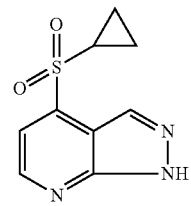

To a solution of 4-iodo-1H-pyrazolo[3,4-b]pyridine (5.2 g) in dimethyl sulfoxide (70 mL) were added N,N'-dimethylethylenediamine (114 μL), copper (I) iodide (202 mg), sodium cyclopropanesulfinate (8.16 g) and potassium carbonate (5.06 g) at room temperature under argon atmosphere, and the mixture was stirred at 100° C. for 16 hr. The reaction mixture was filtered, water was added to the filtrate, and the mixture was extracted with ethyl acetate. The ethyl acetate layer was washed with saturated brine, dried ($MgSO_4$), and concentrated. The obtained residue was subjected to silica gel column chromatography to give the title compound (0.42 g, yield 9%) as yellow crystals from the fraction eluted with ethyl acetate-hexane (1:1, volume ratio). MS: 224 ($MH^+$).

Reference Example 21 ethyl 2-(4-iodo-1H-pyrazolo[3,4-b]pyridin-1-yl)-3-(tetrahydro-2H-pyran-4-yl)propanoate

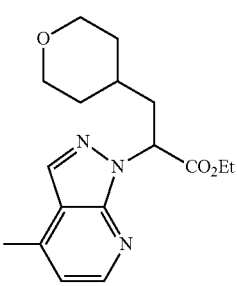

A mixture of 4-iodo-1H-pyrazolo[3,4-b]pyridine (1.72 g), a 1:1 mixture (3.1 g) of ethyl 2-bromo-3-(tetrahydro-2H-pyran-4-yl)propanoate and ethyl 3-(tetrahydro-2H-pyran-4-yl)-2-propenoate, potassium carbonate (1.0 g) and N,N-dimethylformamide (15 mL) was stirred overnight at room temperature. To the reaction mixture was added aqueous citric acid solution, and the mixture was extracted with ethyl acetate. The ethyl acetate layer was washed with water and saturated brine, dried (MgSO$_4$), and concentrated. The residue was subjected to silica gel column chromatography to give the title compound (1.6 g, yield 53%) as a colorless oil from the fraction eluted with ethyl acetate-hexane (35:75, volume ratio). MS: 430 (MH$^+$).

Reference Example 22

N-methoxy-2-(4-methoxy-1H-pyrazolo[3,4-b]pyridin-1-yl)-N-methyl-3-(tetrahydro-2H-pyran-4-yl)propanamide

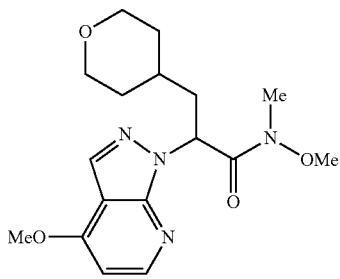 [SMILES: COc1ccnc2c1cnn2C(CC1CCOCC1)C(=O)N(C)OC]

A mixture of ethyl 2-(4-iodo-1H-pyrazolo[3,4-b]pyridin-1-yl)-3-(tetrahydro-2H-pyran-4-yl)propanoate (1.69 g), sodium cyclopropanesulfinate (1.5 g), copper (I) iodide (0.22 g), N,N'-dimethylethylenediamine (0.13 mL), potassium carbonate (1.6 g) and dimethyl sulfoxide (25 mL) was stirred overnight at 100° C. To the reaction mixture was added aqueous citric acid solution, and the mixture was extracted with ethyl acetate. The ethyl acetate layer was washed with saturated brine, dried (MgSO$_4$), and concentrated. The obtained residue was dissolved in a mixed solvent of tetrahydrofuran (10 mL) and methanol (10 mL). To this solution was added an aqueous solution of potassium hydroxide (0.65 g) in water (5 mL), and the mixture was stirred overnight at room temperature. To the reaction mixture was added aqueous citric acid solution, and the mixture was extracted with ethyl acetate. The ethyl acetate layer was washed with saturated brine, dried (MgSO$_4$), and concentrated. A mixture of the obtained residue, N,O-dimethylhydroxylamine hydrochloride (0.38 g), triethylamine (0.54 mL) and N,N-dimethylformamide (20 mL) was ice-cooled, 1H-1,2,3-benzotriazol-1-ol (0.45 g) and N-[3-(dimethylamino)propyl]-N'-ethylcarbodiimide hydrochloride (0.64 g) were added thereto, and the mixture was stirred overnight under ice-cooling to at room temperature. To the reaction mixture was added aqueous sodium hydrogen carbonate solution, and the mixture was extracted with ethyl acetate. The ethyl acetate layer was washed successively with aqueous sodium hydrogen carbonate solution and saturated brine, dried (MgSO$_4$), and concentrated. The obtained residue was subjected to silica gel column chromatography to give the title compound (0.37 g, yield 27%) as a colorless oil from the fraction eluted with ethyl acetate-hexane (65:35, volume ratio). MS: 349 (MH$^+$).

Reference Example 23

4-(4-methoxy-1H-pyrazolo[3,4-b]pyridin-1-yl)-5-(tetrahydro-2H-pyran-4-yl)pent-1-en-3-one

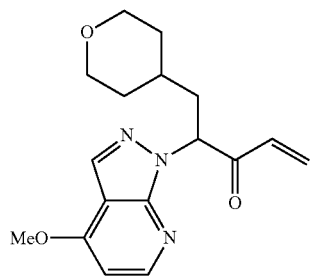 [SMILES: C=CC(=O)C(CC1CCOCC1)n1ncc2c(OC)ccnc21]

To a solution of N-methoxy-2-(4-methoxy-1H-pyrazolo[3,4-b]pyridin-1-yl)-N-methyl-3-(tetrahydro-2H-pyran-4-yl)propanamide (0.37 g) in dry tetrahydrofuran (15 mL) was slowly added vinylmagnesium bromide (1.0M tetrahydrofuran solution: 7.8 mL) at 0° C., and the mixture was stirred at 0° C. for 1 hr. To the reaction mixture was added again vinylmagnesium bromide (1.0M tetrahydrofuran solution: 2.6 mL) at 0° C., and the mixture was stirred for 1 hr under ice-cooling. The reaction solution was poured into an ice-cooled 6M hydrochloric acid, and the mixture was extracted with ethyl acetate. The ethyl acetate layer was washed with saturated brine, dried (MgSO$_4$), and concentrated. The residue was subjected to silica gel column chromatography to give the title compound (0.178 g, yield 53%) as a pale-pink oil from the fraction eluted with ethyl acetate-hexane (6:4, volume ratio). MS: 316 (MH$^+$).

Reference Example 24

1-[5-(1,2-dihydroxy-2-methylpropyl)pyridin-2-yl]-5-(4-methoxy-1H-pyrazolo[3,4-b]pyridin-1-yl)-6-(tetrahydro-2H-pyran-4-yl)hexane-1,4-dione

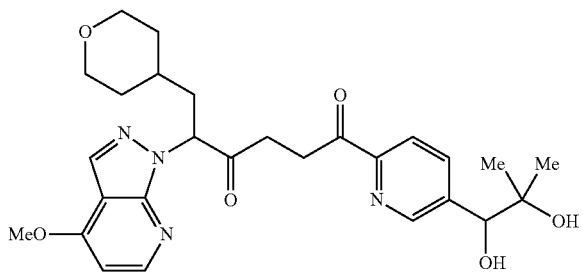 [SMILES: COc1ccnc2c1cnn2C(CC1CCOCC1)C(=O)CCC(=O)c1ccc(C(O)C(C)(C)O)cn1]

A mixture of 4-(4-methoxy-1H-pyrazolo[3,4-b]pyridin-1-yl)-5-(tetrahydro-2H-pyran-4-yl)pent-1-en-3-one (178 mg), 5-(1,2-dihydroxy-2-methylpropyl)pyridine-2-carbaldehyde (132 mg), 3-benzyl-5-(2-hydroxyethyl)-4-methyl-1,3-thiazol-3-ium chloride (18 mg), triethylamine (30 µL), tetrahydrofuran (5 mL) and ethanol (5 mL) was heated under reflux for 3 hr under argon stream. The reaction solution was poured into ice water, and the mixture was extracted with ethyl acetate. The ethyl acetate layer was washed with saturated brine, dried (MgSO$_4$), and concentrated. The residue was subjected to silica gel column chromatography to give the title compound (268 mg, yield 93%) as a pale-yellow oil from the fraction eluted with ethyl acetate. MS: 511 (MH$^+$).

Reference Example 25

2-bromo-5-(2-methylprop-1-en-1-yl)pyridine

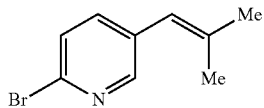

To a solution of (1-methylethyl)(triphenyl)phosphonium iodide (72.2 g) in N,N-dimethylformamide (200 mL) was added a solution of tert-butoxy potassium (20.1 g) in N,N-dimethylformamide (100 mL) under ice-cooling, and the mixture was stirred at 0° C. for 30 min. To the reaction solution was added dropwise a solution of 6-bromopyridine-3-carbaldehyde (20.8 g) in N,N-dimethylformamide (200 mL) at 0° C. The reaction solution was allowed to warm to room temperature, and stirred at room temperature for 16 hr. To the reaction mixture was added saturated aqueous ammonium chloride solution, and the mixture was extracted with diethyl ether. The extract was washed successively with water and saturated brine, dried over anhydrous sodium sulfate, and concentrated under reduced pressure. The residue was purified by silica gel column chromatography (ethyl acetate:hexane=1:99-40:60, volume ratio) to give the title compound (16.2, yield 68%) as a colorless oil.

$^1$H NMR (CDCl$_3$) δ1.84 (3 H, d, J=1.3 Hz), 1.92 (3 H, d, J=1.3 Hz), 6.14 (1 H, s), 7.34-7.45 (2 H, m), 8.22 (1 H, d, J=2.3 Hz).

Reference Example 26

5-(2-methylprop-1-en-1-yl)pyridine-2-carbaldehyde

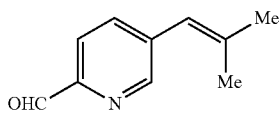 [SMILES: CC(C)=Cc1ccc(C=O)nc1]

Under a nitrogen atmosphere, 2.0M tetrahydrofuran solution (11.2 mL) of butylmagnesium chloride was diluted with tetrahydrofuran (200 mL). The solution was cooled to −10° C., 1.6M hexane solution (28.1 mL) of n-butyllithium was added dropwise thereto, and the mixture was stirred at −10° C. for 10 min. To the reaction solution was added dropwise a solution (50 mL) of 2-bromo-5-(2-methylprop-1-en-1-yl)pyridine (11.9 g) in tetrahydrofuran, and the mixture was stirred at −10° C. for 30 min. To the reaction solution was added N,N-dimethylformamide (8.65 mL), and the mixture was stirred at −10° C. for 3 hr. To the reaction mixture was added saturated aqueous ammonium chloride solution, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=1:99-10:90, volume ratio) to give the title compound (7.47 g, yield 83%) as a pale-yellow oil.

$^1$H NMR (CDCl$_3$) δ1.93 (3 H, s), 1.99 (3 H, s), 6.29 (1 H, s), 7.71 (1 H, d, J=8.0 Hz), 7.93 (1 H, d, J=8.0 Hz), 8.65 (1 H, s), 10.06 (1 H, s).

Reference Example 27

5-(1,2-dihydroxy-2-methylpropyl)pyridine-2-carbaldehyde

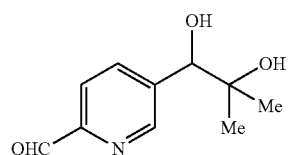 [SMILES: CC(C)(O)C(O)c1ccc(C=O)nc1]

To a solution of 5-(2-methylprop-1-en-1-yl)pyridine-2-carbaldehyde (9.40 g) in a mixed solvent of dimethyl sulfoxide (230 ml) and water (1.89 mL) was added N-bromosuccinic imide (18.7 g) at 0° C. The reaction solution was allowed to warm to room temperature, and stirred at room temperature for 1 hr. To the reaction mixture was added saturated aqueous sodium hydrogen carbonate solution, and the mixture was extracted with ethyl acetate. The extract was washed successively with water and saturated brine, dried over anhydrous sodium sulfate, and concentrated under reduced pressure. To a solution of the residue in tetrahydrofuran (200 ml) was added 4.5M aqueous sulfuric acid solution, and the mixture was stirred at room temperature for 3 hr. The reaction mixture was neutralized with aqueous sodium hydroxide solution and saturated aqueous sodium hydrogen carbonate solution, and the mixture was extracted with ethyl acetate. The extract was washed successively with water and saturated brine, dried over anhydrous sodium sulfate, and concentrated under reduced pressure. The residue was purified by silica gel column chromatography (ethyl acetate:hexane=20:80 to 100:0, volume ratio) to give the title compound (9.00 g, yield 79%) as a pale-yellow oil. MS: 196 (MH$^+$).

Example 1

[2-(5-{1-[1-methyl-5-(methylsulfanyl)-1H-pyrazol-3-yl]-2-(tetrahydro-2H-pyran-4-yl)ethyl}-1H-pyrrol-2-yl)-1,3-thiazol-5-yl]methanol

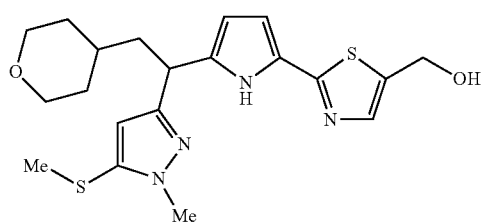 [SMILES: CSc1cc(C(CC2CCOCC2)c2ccc(-c3ncc(CO)s3)[nH]2)nn1C]

A mixture of 5-[1-methyl-5-(methylsulfanyl)-1H-pyrazol-3-yl]-6-(tetrahydro-2H-pyran-4-yl)-1-{5-[(tetrahydro-2H-pyran-2-yloxy)methyl]-1,3-thiazol-2-yl}hexane-1,4-dione (0.65 g), ammonium acetate (0.46 g) and acetic acid (6 mL) was stirred at 100° C. for 1 hr. The reaction mixture was neutralized with 8N aqueous sodium hydroxide solution, and the mixture was extracted with ethyl acetate. The ethyl acetate layer was washed with saturated brine, dried (MgSO$_4$), and concentrated. The residue was subjected to basic silica gel column chromatography to give the title compound (0.40 g, yield 80%) as a yellow amorphous solid from the fraction eluted with tetrahydrofuran-hexane (3:1, volume ratio). MS: 419 (MH+).

¹H NMR (300 MHz, CDCl₃) δ1.20-1.92 (7 H, m), 2.36 (3 H, s), 2.62 (1 H, brs), 3.22-3.32 (2 H, m), 3.80-3.93 (5 H, m), 4.01 (1 H, t, J=8.0 Hz), 4.81 (2 H, s), 6.00 (1 H, s), 6.04 (1 H, t, J=3.2 Hz), 6.57 (1 H, t, J=3.2 Hz), 7.44 (1 H, s), 9.58 (1 H, brs).

Example 2

[2-(5-{1-[1-methyl-5-(methylsulfonyl)-1H-pyrazol-3-yl]-2-(tetrahydro-2H-pyran-4-yl)ethyl}-1H-pyrrol-2-yl)-1,3-thiazol-5-yl]methanol

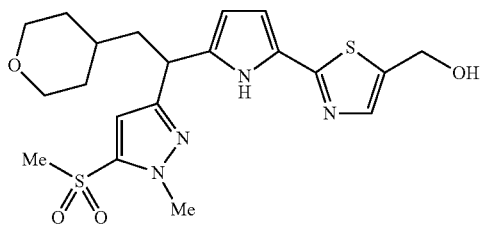 [SMILES: Cn1nc(C(CC2CCOCC2)c2ccc(-c3ncc(CO)s3)[nH]2)cc1S(C)(=O)=O]

A mixture of [2-(5-{1-[1-methyl-5-(methylsulfanyl)-1H-pyrazol-3-yl]-2-(tetrahydro-2H-pyran-4-yl)ethyl}-1H-pyrrol-2-yl)-1,3-thiazol-5-yl]methanol (0.40 g), oxone (registered trade mark) (0.89 g), water (6 mL), tetrahydrofuran (6 mL) and methanol (6 mL) was stirred at room temperature for 1 hr. To the reaction mixture was added saturated aqueous sodium hydrogen carbonate, and the mixture was extracted with ethyl acetate. The ethyl acetate layer was washed with saturated brine, dried (MgSO₄), and concentrated. The residue was subjected to basic silica gel column chromatography to give the title compound (0.30 g, yield 70%) as a colorless amorphous solid from the fraction eluted with tetrahydrofuran-hexane (3:1, volume ratio). MS: 451 (MH+).

¹H NMR (300 MHz, CDCl₃) δ1.20-1.66 (5 H, m), 1.88-1.96 (2H, m), 2.33 (1 H, brt, J=5.3 Hz), 3.13 (3 H, s), 3.23-3.34 (2 H, m), 3.86-3.95 (2 H, m), 4.11 (3 H, s), 4.13 (1 H, t, J=7.8 Hz), 4.82 (2 H, d, J=5.3 Hz), 6.05 (1 H, t, J=3.3 Hz), 6.57 (1 H, dd, J=2.4, 3.3 Hz), 7.45 (1 H, s), 9.48 (1 H, brs).

Example 3

1-(6-{5-[1-(4-methoxy-1H-pyrazolo[3,4-b]pyridin-1-yl)-2-(tetrahydro-2H-pyran-4-yl)ethyl]-1H-pyrrol-2-yl}pyridin-3-yl)-2-methylpropane-1,2-diol

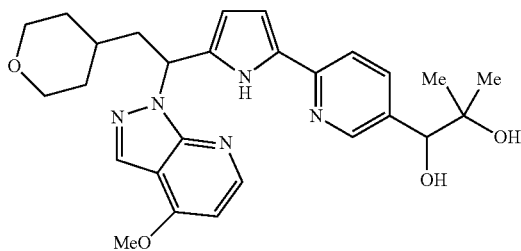 [SMILES: COc1ccnc2c1cnn2C(CC1CCOCC1)c1ccc(-c2ccc(C(O)C(C)(C)O)cn2)[nH]1]

A mixture of 1-[5-(1,2-dihydroxy-2-methylpropyl)pyridin-2-yl]-5-(4-methoxy-1H-pyrazolo[3,4-b]pyridin-1-yl)-6-(tetrahydro-2H-pyran-4-yl)hexane-1,4-dione (265 mg), ammonium acetate (200 mg), acetic acid (0.20 mL) and ethanol (10 mL) was stirred at room temperature for 6 hr. The reaction solution was poured into aqueous sodium hydrogen carbonate solution, and the mixture was extracted with ethyl acetate. The ethyl acetate layer was washed with saturated brine, dried (MgSO₄), and concentrated. The residue was subjected to silica gel column chromatography to give the title compound (178 mg, yield 58%) as a colorless amorphous solid from the fraction eluted with ethyl acetate. MS: 492 (MH+).

¹H NMR (300 MHz, CDCl₃) δ1.09 (3H, s), 1.20-1.90 (8H, m), 2.18-2.30 (1H, m), 2.50-2.66 (1H, m), 3.10-3.27 (2H, m), 3.86 (2H, d, J=11.4 Hz), 3.99 (3H, s), 4.50 (1H, s), 6.22 (1H, dd, J=6.6, 9.6 Hz), 6.29 (1H, t, J=3.0 Hz), 6.46 (1H, d, J=5.4 Hz), 6.56% (1H, t, J=3.0 Hz), 7.41 (1H, d, J=8.1 Hz), 7.60-7.67 (1H, M), 8.05 (1H, s), 8.33-8.40 (2H, m), 10.56 (1H, brs).

Example 4

1-[6-(5-{1-[4-(cyclopropylsulfonyl)-1H-indazol-1-yl]-2-(tetrahydro-2H-pyran-4-yl)ethyl}-1H-pyrrol-2-yl)pyridin-3-yl]-2-methylpropane-1,2-diol

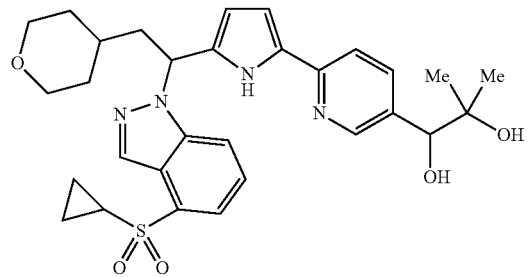 [SMILES: CC(C)(O)C(O)c1ccc(-c2ccc(C(CC3CCOCC3)n3ncc4c(S(=O)(=O)C5CC5)cccc43)[nH]2)nc1]

A mixture of 5-[4-(cyclopropylsulfonyl)-1H-indazol-1-yl]-1-[5-(1,2-dihydroxy-2-methylpropyl)pyridin-2-yl]-6-(tetrahydro-2H-pyran-4-yl)hexane-1,4-dione (0.50 g), ammonium acetate (0.35 g), acetic acid (0.50 mL) and ethanol (10 mL) was stirred at room temperature for 13 hr. The reaction solution was poured into aqueous sodium hydrogen carbonate solution, and the mixture was extracted with ethyl acetate.

The ethyl acetate layer was washed with saturated brine, dried (MgSO₄), and concentrated. The residue was subjected to silica gel column chromatography to give the title compound (0.155 g, yield 32%) as a colorless amorphous solid from the fraction eluted with ethyl acetate-hexane (95:5, volume ratio). MS: 565 (MH+).

¹H NMR (300 MHz, CDCl₃) δ0.96-1.76 (14H, m), 2.22-2.35 (2H, m), 2.50-2.63 (2H, m), 3.05 (1H, brs), 3.22 (2H, q, J=7.8 Hz), 3.88 (2H, d, J=8.4 Hz), 4.89 (1H, s), 5.88 (1H, t, J=4.8 Hz), 6.27-6.30 (1H, m), 6.57-6.61 (1H, m), 7.40-7.70 (5H, m), 8.33 (1H, s), 8.47 (1H, s), 9.93 (1H, brs).

Example 5

1-[6-(5-{1-[4-(cyclopropylsulfonyl)-5-methoxy-1H-indazol-1-yl]-2-(tetrahydro-2H-pyran-4-yl)ethyl}-1H-pyrrol-2-yl)pyridin-3-yl]-2-methylpropane-1,2-diol

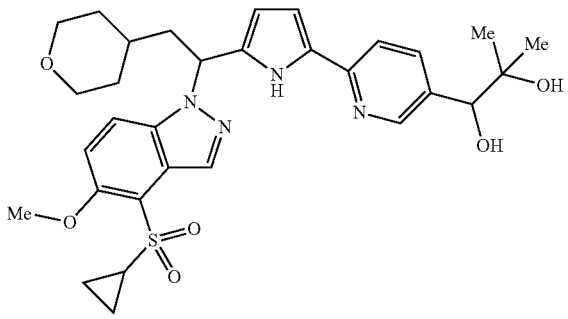 [SMILES: COc1ccc2c(cnn2C(CC2CCOCC2)c2ccc(-c3ccc(C(O)C(C)(C)O)cn3)[nH]2)c1S(=O)(=O)C1CC1]

A mixture of 5-[4-(cyclopropylsulfonyl)-5-methoxy-1H-indazol-1-yl]-1-[5-(1,2-dihydroxy-2-methylpropyl)pyridin-2-yl]-6-(tetrahydro-2H-pyran-4-yl)hexane-1,4-dione (0.37 g), ammonium acetate (0.23 g), acetic acid (0.34 mL) and ethanol (10 mL) was stirred at room temperature for 15 hr. To the reaction mixture was added saturated aqueous sodium hydrogen carbonate solution, and the mixture was extracted with ethyl acetate. The ethyl acetate layer was washed with saturated brine, dried (MgSO$_4$), and concentrated. The residue was subjected to silica gel column chromatography, and eluted from hexane-ethyl acetate (1:1-0:1, volume ratio) to give the title compound (60 mg, yield 17%) as a colorless amorphous solid. MS: 595 (MH$^+$).

$^1$H NMR (300 MHz, CDCl$_3$) δ0.87-1.03 (2 H, m), 1.06 (3 H, s), 1.15-1.56 (10 H, m), 1.60-1.84 (2 H, m), 2.14-2.33 (1 H, m), 2.40-2.60 (1 H, m), 2.95-3.41 (3 H, m), 3.80-3.93 (2 H, m), 3.95-4.03 (3 H, m), 4.46 (1 H, s), 5.80 (1 H, t, J=6.82 Hz), 6.26 (1 H, d, J=2.27 Hz), 6.58 (1 H, brs), 7.09-7.18 (1 H, m), 7.44 (1 H, d, J=8.33 Hz), 7.56 (1 H, t, J=8.33 Hz), 7.66 (1 H, d, J=8.33 Hz), 8.24-8.34 (1 H, m), 8.55 (1 H, s), 10.03 (1 H, brs).

Experimental Example 1

Measurement of GK Activation Value

GK enzyme reactions were performed in 50 mmol/L HEPES pH7.4, 200 mmol/L KCl, 5 mmol/L MgCl$_2$, 2 mmol/L DTT, containing 50 μmol/L 2'-(or-3')-O—(N-methylanthraniloyl)adenosine 5'-triphosphate (Mant-ATP) (Jena Bioscience GmbH), 5 mmol/L D-glucose, 5% DMSO and 6 μg/mL GST-hLGK1 obtained in Reference Example 2A in a total volume 50 μL. The reactions were performed in 384 well black plates (Nalge Nunc International K.K.). Prior to the reaction, the enzyme and test compound were incubated for 10 min at 37° C., and 25 mM D-glucose solution (10 μL) was added to start the reaction. The final concentration of the test compound is 10 μmol/L. After the incubation for 60 min at 37° C., the reaction was quenched by adding 25 μL of a quenching solution (containing 200 mM HEPES (pH 7.4), 20 mM MgCl$_2$, 200 mM EDTA, 0.03% Triton-X 100, 0.3% Coating 3 reagent (Caliper Life Sciences, Inc.)).

Mant-ATP (substrate, 2'-(or-3')-O—(N-methylanthraniloyl)adenosine 5'-triphosphate) and Mant-ADP (reaction resultant product) were separated from each well after the reaction by a microchip type capillary electrophoresis apparatus 250 HTS (Caliper Life Sciences, Inc.). The reaction rate [(reaction resultant product peak height)/(reaction resultant product peak height+substrate peak height)×100(%)] was calculated from the ratio of the substrate peak height and reaction resultant product peak height obtained by fluorescence detection (excitation wavelength 355 nm, measurement wavelength 460 nm) and used as the index of GK activity.

As a control group, the reaction rate was calculated in the same manner as above without the test compounds.

The percentage obtained by dividing the reaction rate of the well added with the test compound (test compound addition group) by the reaction rate of the control group was taken as the GK activity value (Emax) of the test compound. The results are shown in Table 1.

TABLE 1

| Example No. | Emax (%) |
|---|---|
| 2 | 138 |
| 3 | 124 |
| 4 | 161 |
| 5 | 162 |

As is clear from Table 1, the compound of the present invention has a superior glucokinase activation action.

Formulation Example 1

Production of Capsule

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablet

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The total amount of 1), 2) and 3), and 30 g of 4) are kneaded with water, vacuum dried and sized. The sieved powder is mixed with 14 g of 4) and 1 g of 5), and the mixture is punched by a tableting machine. In this way, 1000 tablets containing 30 mg of the compound of Example 1 per tablet are obtained.

Industrial Applicability

The glucokinase activator of the present invention has a superior activity, and therefore the activator is useful as a pharmaceutical agent such as an agent for the prophylaxis or treatment of diabetes, obesity and the like, and the like.

This application is based on patent application Nos. 107181/2008 and 275892/2008 filed in Japan, the contents of which are hereby incorporated by reference.

The invention claimed is:

1. A compound represented by the formula (I):

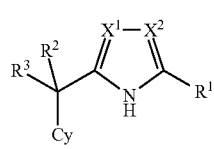

wherein

R¹ is a 6-membered nitrogen-containing heterocyclic group represented by the formula:

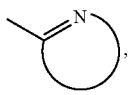

which is optionally substituted;

R² is an optionally substituted alkyl group;

R³ is a hydrogen atom;

Cy is an optionally substituted 5-membered cyclic group, which is optionally condensed with an optionally substituted 6-membered ring; and X¹ and X² are each independently an optionally substituted carbon atom, provided that Cy is not 1H-pyrrol-2-yl, or a salt thereof.

2. The compound or salt of claim 1, wherein Cy is pyrazolyl, pyrazolopyridyl, imidazolyl, triazolyl, tetrazolyl, thienyl, furyl, thiazolyl, thiadiazolyl, oxazolyl, oxadiazolyl, isoxazolyl, isothiazolyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl or benzisothiazolyl, each of which is optionally substituted.

3. The compound or salt of claim 1, wherein R¹ is a 6-membered nitrogen-containing aromatic heterocyclic group represented by the formula:

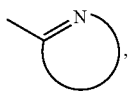

which is optionally substituted.

4. The compound or salt of claim 1, wherein

Cy is pyrazolyl, pyrazolopyridyl, imidazolyl, triazolyl, tetrazolyl, thienyl, furyl, thiazolyl, thiadiazolyl, oxazolyl, oxadiazolyl, isoxazolyl, isothiazolyl, indazolyl, indazolinyl, indolyl, indolinyl, benzimidazolyl, benzotriazolyl, benzothienyl, benzofuryl, benzothiazolyl, benzothiadiazolyl, benzoxazolyl, benzoxadiazolyl, benzisoxazolyl or benzisothiazolyl, each of which is optionally substituted, R¹ is a 6-membered nitrogen-containing aromatic heterocyclic group represented by the formula:

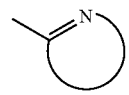

which is optionally substituted,

R² is an optionally substituted $C_{1-6}$ alkyl group,

R³ is a hydrogen atom, and

X¹ and X² are both optionally substituted carbon atoms.

5. [2-(5-{1-[1-Methyl-5-(methylsulfanyl)-1H-pyrazol-3-yl]-2-(tetrahydro-2H-pyran-4-yl)ethyl}-1H-pyrrol-2-yl)-1,3-thiazol-5-yl]methanol or a salt thereof.

6. [2-(5-{1-[1-Methyl-5-(methylsulfonyl)-1H-pyrazol-3-yl]-2-(tetrahydro-2H-pyran-4-yl)ethyl}-1H-pyrrol-2-yl)-1,3-thiazol-5-yl]methanol or a salt thereof.

7. 1-(6-{5-[1-(4-Methoxy-1H-pyrazolo[3,4-b]pyridin-1-yl)-2-(tetrahydro-2H-pyran-4-yl)ethyl]-1H-pyrrol-2-yl}pyridin-3-yl)-2-methylpropane-1,2-diol or a salt thereof.

8. 1-[6-(5-{1-[4-(Cyclopropylsulfonyl)-1H-indazol-1-yl]-2-(tetrahydro-2H-pyran-4-yl)ethyl}-1H-pyrrol-2-yl)pyridin-3-yl]-2-methylpropane-1,2-diol or a salt thereof.

9. 1-[6-(5-{1-[4-(Cyclopropylsulfonyl)-5-methoxy-1H-indazol-1-yl]-2-(tetrahydro-2H-pyran-4-yl)ethyl}-1H-pyrrol-2-yl)pyridin-3-yl]-2-methylpropane-1,2-diol or a salt thereof.

10. A pharmaceutical agent comprising a compound represented by the formula (I):

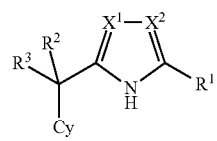

wherein

R¹ is a 6-membered nitrogen-containing heterocyclic group represented by the formula:

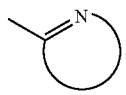

which is optionally substituted;

R² is an optionally substituted alkyl group;

R³ is a hydrogen atom;

Cy is an optionally substituted 5-membered cyclic group, which is optionally condensed with an optionally substituted 6-membered ring; and X¹ and X² are each independently an optionally substituted carbon atom, or a salt thereof, and a pharmacologically acceptable carrier.

11. A method for the treatment of Type II diabetes in a mammal, which comprises administering an effective amount of the compound or salt of claim 1 to the mammal.

12. A pharmaceutical composition comprising the compound or salt according to claim 1 and a pharmacologically acceptable carrier.

* * * * *

UNITED STATES PATENT AND TRADEMARK OFFICE
CERTIFICATE OF CORRECTION

PATENT NO. : 8,349,886 B2
APPLICATION NO. : 12/937820
DATED : January 8, 2013
INVENTOR(S) : Tsuneo Yasuma It is certified that error appears in the above-identified patent and that said Letters Patent is hereby corrected as shown below:

In the Claims:

Claim 9, in column 76, lines 25-28:

"1-[6-(5-{1-[4-(Cyclopropylsulfonyl)-5-methoxy- 1H-indazol-1-yl]-2-(tetrahydro-2H-pyran-4-yl)ethyl}-1H-pyrrol-2-yl)pyridin-3-yl]-2-methylpropane-1,2-diol or asalt thereof.",
should read
--1-[6-(5-{1-[4-(Cyclopropylsulfonyl)-5-methoxy-1H-indazol-1-yl]-2-(tetrahydro-2H-pyran-4-yl)ethyl}-1H-pyrrol-2-yl)pyridin-3-yl]-2-methylpropane-1,2-diol or ~~asalt~~ a salt thereof.--.

Claim 10, in column 76, lines 29 and 30:

"A pharmaceutical agent comprising a compound represented by the formula (I):", should read
--A pharmaceutical ~~agent~~ composition comprising a compound represented by the formula (I):--.

Signed and Sealed this
Thirtieth Day of April, 2013

Teresa Stanek Rea
*Acting Director of the United States Patent and Trademark Office*